(12) United States Patent
Nieminen et al.

(10) Patent No.: US 11,446,013 B2
(45) Date of Patent: Sep. 20, 2022

(54) METHOD AND APPARATUS FOR EXTRACTING AND DELIVERY OF ENTITIES

(71) Applicant: Swan Cytologics, Inc., Toronto (CA)

(72) Inventors: Heikki J. Nieminen, Helsinki (FI); Kenneth P. H. Pritzker, Toronto (CA); Eetu Lampsijärvi, Helsinki (FI); Edward Haeggström, Helsinki (FI)

(73) Assignee: Swan Cytologics, Inc., Toronto (CA)

( * ) Notice: Subject to any disclaimer, the term of this patent is extended or adjusted under 35 U.S.C. 154(b) by 304 days.

(21) Appl. No.: 16/312,844

(22) PCT Filed: Jun. 30, 2017

(86) PCT No.: PCT/CA2017/050803
§ 371 (c)(1),
(2) Date: Dec. 21, 2018

(87) PCT Pub. No.: WO2018/000102
PCT Pub. Date: Jan. 4, 2018

(65) Prior Publication Data
US 2019/0321013 A1 Oct. 24, 2019

Related U.S. Application Data

(60) Provisional application No. 62/357,485, filed on Jul. 1, 2016.

(51) Int. Cl.
*A61B 10/02* (2006.01)
*A61B 10/00* (2006.01)
(Continued)

(52) U.S. Cl.
CPC ...... *A61B 10/0283* (2013.01); *A61B 10/0096* (2013.01); *A61B 17/320068* (2013.01);
(Continued)

(58) Field of Classification Search
CPC ........ A61B 10/0283; A61B 17/320068; A61B 2017/32007
See application file for complete search history.

(56) References Cited

U.S. PATENT DOCUMENTS 3,792,701 A 2/1974 Kloz et al.
4,750,488 A 6/1988 Wuchinich et al.
(Continued)

FOREIGN PATENT DOCUMENTS

CA 3028252 A1 1/2018
CN 101646396 A 2/2010
(Continued)

OTHER PUBLICATIONS

International Search Report and Written Opinion dated Oct. 2, 2017 in corresponding International Patent Application No. PCT/CA2017/050803 (8 pages).
(Continued)

*Primary Examiner* — Kevin C Sirmons
*Assistant Examiner* — Leah J Swanson
(74) *Attorney, Agent, or Firm* — Bereskin & Parr LLP/S.E.N.C.R.L., s.r.l.; Tony Orsi

(57) ABSTRACT

Various embodiments are described herein for a device for using acoustic or mechanical energy to perform an action at a target site of an object. The device comprises a conduit having an aperture disposed at the target site, a displacement signal source for generating a mechanical displacement signal, a coupling assembly having for coupling the displacement signal source to the conduit, a pressure controller coupled to the proximal end of the conduit to vary an amount of pressure in the conduit when obtaining a first entity from or delivering a second entity to the target site, and a control unit for controlling the displacement signal source to gen-
(Continued)

erate the mechanical displacement signal based on a desired acoustic or mechanical wave mode.

58 Claims, 21 Drawing Sheets

(51) Int. Cl.
    *A61B 17/32* (2006.01)
    *A61B 17/34* (2006.01)
    *A61B 17/00* (2006.01)

(52) U.S. Cl.
    CPC ...... *A61B 17/34* (2013.01); *A61B 2010/0208* (2013.01); *A61B 2017/00022* (2013.01); *A61B 2017/00146* (2013.01); *A61B 2017/32007* (2017.08); *A61B 2562/0247* (2013.01)

(56) References Cited

U.S. PATENT DOCUMENTS

| | | | |
|---|---|---|---|
| 5,702,360 A | 12/1997 | Dieras et al. | |
| 5,746,713 A | 5/1998 | Hood et al. | |
| 5,902,279 A * | 5/1999 | Powles | A61B 10/0283 604/239 |
| 6,032,561 A | 3/2000 | Lonn et al. | |
| 6,251,110 B1 | 6/2001 | Wampler | |
| 6,702,761 B1 | 3/2004 | Damadian et al. | |
| 6,723,110 B2 | 4/2004 | Timm et al. | |
| 8,287,483 B2 | 10/2012 | Mitragotri et al. | |
| 8,324,570 B2 | 12/2012 | Wiseman et al. | |
| 8,845,537 B2 | 9/2014 | Tanaka et al. | |
| 8,852,104 B2 | 10/2014 | Oralkan et al. | |
| 8,858,439 B2 | 10/2014 | Tanaka et al. | |
| 9,943,675 B1 * | 4/2018 | Keilman | A61M 37/0092 |
| 2005/0021065 A1 * | 1/2005 | Yamada | A61B 17/320068 606/169 |
| 2009/0306694 A1 * | 12/2009 | Babaev | A61B 17/3203 606/169 |
| 2010/0004558 A1 | 1/2010 | Frankhouser et al. | |
| 2010/0100139 A1 | 4/2010 | Young | |
| 2010/0135717 A1 | 6/2010 | Thoms | |
| 2011/0015631 A1 | 1/2011 | Wiener et al. | |
| 2011/0160620 A1 * | 6/2011 | Gill | A61B 8/4444 601/2 |
| 2012/0203257 A1 | 8/2012 | Stulen et al. | |
| 2012/0209303 A1 * | 8/2012 | Frankhouser | A61B 90/06 606/169 |
| 2013/0046230 A1 | 2/2013 | Lewis, Jr. et al. | |
| 2013/0131705 A1 * | 5/2013 | Akagane | A61N 7/00 606/169 |
| 2014/0058361 A1 * | 2/2014 | Gordon | A61M 1/0031 604/542 |
| 2014/0148832 A1 | 5/2014 | Walton et al. | |
| 2015/0105791 A1 * | 4/2015 | Truckai | A61B 17/32002 606/115 |
| 2015/0257778 A1 * | 9/2015 | Harrington | A61B 17/22012 606/169 |
| 2015/0283334 A1 * | 10/2015 | Marx | A61M 5/3287 604/112 |
| 2015/0337289 A1 | 11/2015 | Kimmel et al. | |
| 2015/0374348 A1 | 12/2015 | Hingston | |

FOREIGN PATENT DOCUMENTS

| | | |
|---|---|---|
| CN | 102917656 A | 2/2013 |
| CN | 103327920 A | 9/2013 |
| CN | 109982649 A | 7/2019 |
| CN | 104902942 A | 9/2019 |
| DE | 2065681 A1 | 3/1975 |
| JP | 2010-523182 A | 7/2010 |
| JP | 2019528807 A | 10/2019 |
| WO | 90/01971 A1 | 3/1990 |
| WO | 98/00194 A2 | 1/1998 |
| WO | 2006/046029 A2 | 5/2006 |
| WO | 2008/108817 A1 | 9/2008 |
| WO | 2011/033277 A2 | 3/2011 |
| WO | 2012/078447 A2 | 6/2012 |
| WO | 2014/140556 A1 | 9/2014 |
| WO | 2018/000102 A1 | 1/2018 |

OTHER PUBLICATIONS

Krebs et al., "Large-core biopsy guns: comparison for yield of breast tissue", Radiology, Aug. 1996, 200(2): 365-368 (abstract—1 page).
"FDA discourages use of laparoscopic power morcellation for removal of uterus or uterine fibroids", FDA News Release, Apr. 17, 2014 (2 pages).
Vanderlaan, "Fine-Needle Aspiration and Core Needle Biopsy: An Update on 2 Common Minimally Invasive Tissue Sampling Modalities", Cancer Cytopathology, Dec. 2016 (Epub May 16, 2016), 124(12): 862-870.
Kuang et al., "Modelling and characterisation of a ultrasound-actuated needle for improved visibility in ultrasound-guided regional anaesthesia and tissue biopsy", Ultrasonics, Jul. 2016 (Epub Mar. 3, 2016), 69: 38-46.
Mozo et al., "Review of ultrasonic irrigation in endodontics: increasing action of irrigating solutions", Med Oral Patol Oral Cir Bucal., May 1, 2012, 17(3): e512-6.
Extended European Search Report dated Aug. 12, 2020 in EP Patent Application No. 17818791.0 (12 pages).
Dhan et al., Chapter 2—"Basics of Ultrasound Imaging", in Narouze (ed ), "Atlas of Ultrasound-Guided Procedures in Interventional Pain Management", Springer Science+Business Media, LLC, New York, 2011, pp. 13-19.
Carovac et al., "Application of Ultrasound in Medicine", AIM, Sep. 3, 2011, 19(3): 168-171.
Office Action dated Mar. 29, 2021 issued in JP Patent Application No. 2018-567905 (10 pages including English translation).
First Official Action and Search Report dated May 24, 2021 in CN Patent Application No. 201780053953.6 (61 pages including English translations—pp. 16-36 (machine translation from Global Dossier) and pp. 37-61 (translation from CN agent)).
Examination Report dated Jun. 24, 2021 in IN Patent Application No. 201927003699 (6 pages).
Seco et al., Chapter 1, "Modelling the Generation and Propagation of Ultrasonic Signals in Cylindrical Waveguides", in Santos Junior ed., "Ultrasonic Waves", IntechOpen, Mar. 7, 2012, pp. 1-28.
"Waveguide", Wikimedia Foundation, Inc., May 6, 2016 <http://web.archive.org/web/20160617065011/https://en.wikipedia.org/wiki/Waveguide> (5 pages).
"Waveguide (acoustics)", Wikimedia Foundation, Inc., Oct. 27, 2014 <https://web.archive.org/web/20150511231346/https://en.wikipedia.org/wiki/Waveguide_(acoustics)> (2 pages).

* cited by examiner

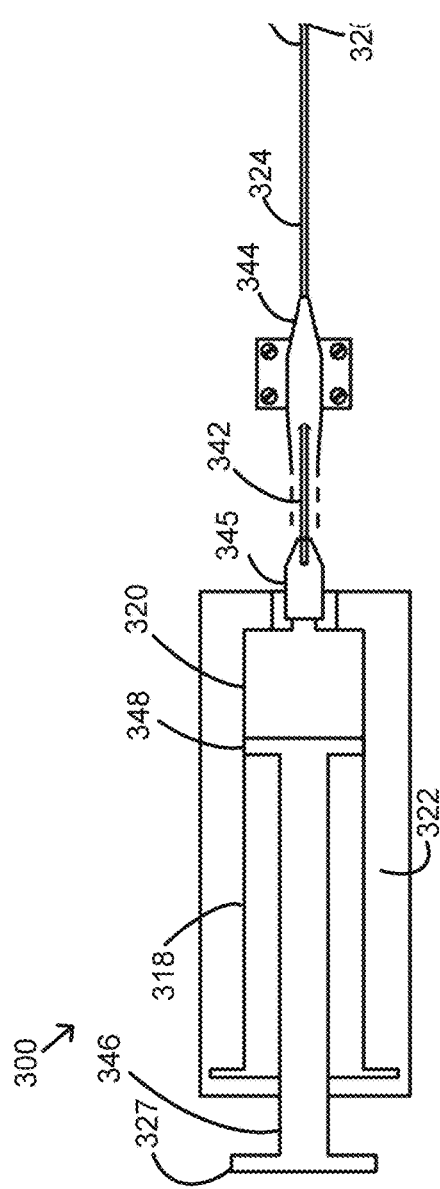
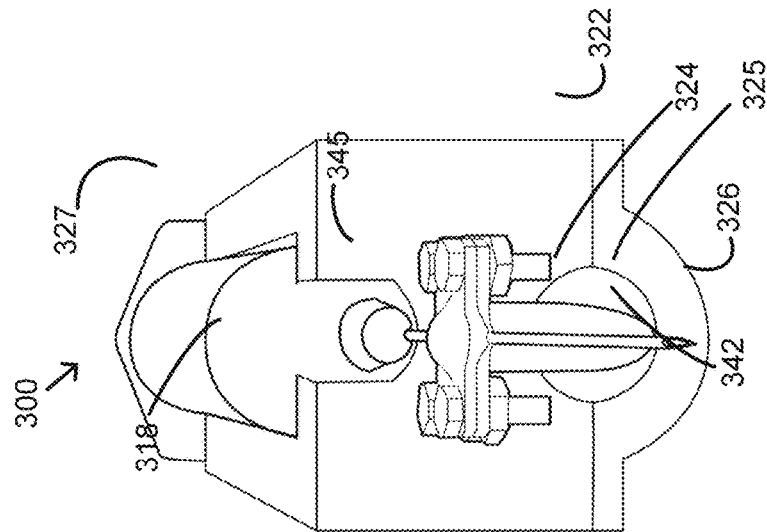
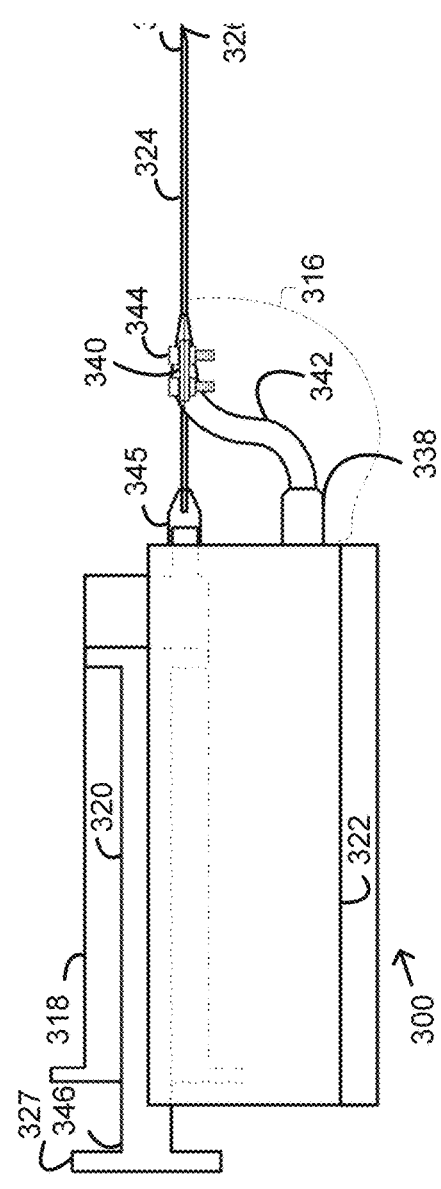
FIG. 3A
FIG. 3B
FIG. 3C

FIG. 10A
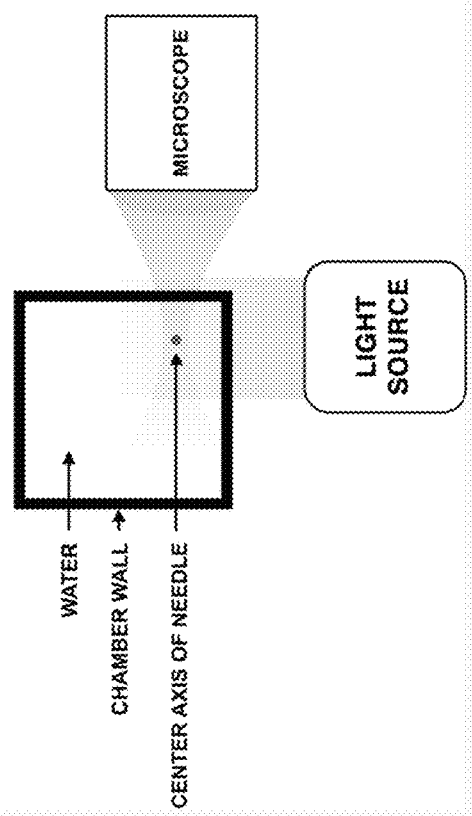
FIG. 10B
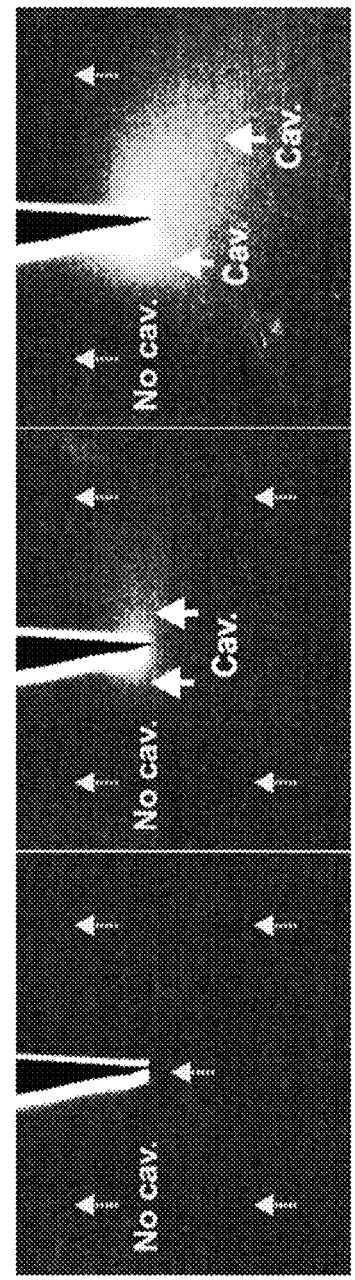
FIG. 10C
FIG. 10D
FIG. 10E
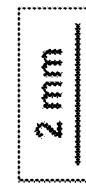

METHOD AND APPARATUS FOR EXTRACTING AND DELIVERY OF ENTITIES

CROSS-REFERENCE TO RELATED APPLICATION

This application is a 35 USC § 371 national stage entry of International Patent Application No. PCT/CA2017/050803, filed Jun. 30, 2017, which claims the benefit of U.S. Provisional Patent Application No. 62/357,485, filed Jul. 1, 2016, entitled "METHOD AND APPARATUS FOR EXTRACTING AND DELIVERY OF ENTITIES"; the contents of each of which are hereby incorporated herein in their entirety by reference.

FIELD

Various embodiments are described herein for an apparatus and method that may be used to extract entities from a subject in some cases, manipulate the samples in other cases and/or in still other cases to deliver entities to the subject.

BACKGROUND

Fine-Needle Aspiration (FNA) is a technique that is used to extract cells from potentially pathologic tissues such as breast cancer tumors for in vitro diagnostics. FNA employs a conventional needle, which may be a hypodermic needle in some cases, and a syringe as follows: (i) the needle (attached to the syringe) is inserted into the target tissue (e.g. tumor), (ii) the syringe piston is pulled to induce suction (low pressure) and (iii) the needle is translated or moved to detach cells from the tissue. Due to suction the detached cells are captured inside the needle. The major advantage of FNA is that it can be conducted in a general physician's office.

A problem with FNA is its user-dependency since the needle needs to be inserted into the target tissue and the syringe attached to the needle needs to be translated and rotated by hand while maintaining vacuum. This causes high intra-user and inter-user variability in the yield of obtained potentially pathological cells as well as limited capability to maintain the structure of the extracted tissue.

Another problem with FNA is that the potentially pathological cells may not be extracted even if they exist in the target tissue; this applies especially to sarcomas, breast cancer, thyroid cancer, prostate cancer, tumors, and other lesions if there is a high collagenous connective tissue component.

These problems with FNA can lead to inconclusive or biased diagnosis or repeat FNA. Generally speaking, failure to obtain samples relevant to the pathologist can be limiting to achieve diagnosis or other clinical relevant information, both to the clinician and the patient undergoing the FNA procedure as well as increasing the hazard and costs if a subsequent biopsy is required.

An alternative to using FNA is core needle biopsy (CNB), which is a technique that is conducted in a surgical setting. CNB can extract from the target, e.g. a tumor, a tissue sample that is greater in volume than that obtained with FNA. Therefore, the probability of acquiring potentially pathological cells is greater than with FNA. The CNB technique is more proficient than FNA in maintaining the tissue structure.

However, there are issues with CNB: (i) the procedure is costly compared to FNA, (ii) CNB cannot be conducted at the general practitioner's office (it usually requires a treatment room or an operation theatre); (iii) CNB can subject the patient to bleeding and other adverse effects less likely to occur with FNA because of CNB's greater instrument diameter inside the target; and (iv) CNB has a failure to obtain a sample rate similar to FNA.

A third approach is to apply hammering to extract bone samples. This can be very painful to the patient. A fourth approach exploits suction of bone marrow from a patient. This approach can also induce significant pain to the patient.

SUMMARY OF VARIOUS EMBODIMENTS

In a broad aspect, at least one embodiment described herein provides a device for delivery of acoustic or mechanical energy to perform an action at a target site of the object, the device comprising: a conduit having a proximal end and a distal end with a tip; a displacement signal source for generating a mechanical displacement signal; a coupling assembly having a first end coupled to the displacement signal source and a second end coupled at a coupling point on the conduit between the proximal end and the distal end of the conduit, the coupling assembly being configured to couple the mechanical displacement signal to the conduit during use; a pressure controller coupled to the proximal end of the conduit and being configured to vary an amount of pressure in the conduit during use; and a control unit coupled to the displacement signal source for controlling the displacement signal source to generate the mechanical displacement signal based on at least one of the location of the coupling point and the coupling angle between the second end of the coupling assembly and the conduit to implement a desired acoustic or mechanical wave mode at a portion of the conduit.

In at least one embodiment, the coupling point on the conduit may be near the proximal end of the conduit or a central part of the conduit.

In at least one embodiment, the displacement signal source has a longitudinal axis that is offset or at an angle with respect to the conduit and the coupling assembly has a transition region where a longitudinal central axis of the waveguide is different than a longitudinal central axis of the displacement signal source.

In at least one embodiment, the waveguide is operated as a resonator having an eigenmode that is selected to achieve a preferred resonant frequency of the conduit for improved action at the tip of the conduit.

In at least one embodiment, the coupling assembly comprises a waveguide portion having an S shape.

In at least one embodiment, the second end of the coupling assembly may comprise a converging structure to provide a first stage of amplification for the mechanical displacement signal as the mechanical displacement signal is coupled to the conduit.

In at least one embodiment, the converging structure may comprise an upper portion with a first channel on a lower surface thereof, and a lower portion with a second channel on an upper surface thereof, the first and second channels being sized to receive a portion of the conduit therebetween to transfer the mechanical displacement signal thereto during use.

In at least one embodiment, the upper portion of the second end of the coupling assembly may be shaped to provide an upper portion of the converging structure and the lower portion of the second end of the coupling assembly is shaped to provide a lower portion of the converging structure.

In at least one embodiment, the coupling assembly may comprise a waveguide portion having a J shape.

In at least one embodiment, the second end of the coupling assembly contacts an outer surface of the conduit tangentially to create acoustic or mechanical waves on an inner surface of the conduit and the outer surface of the conduit.

In at least one embodiment, the device may further comprise at least one additional displacement signal source and a corresponding at least one additional coupling assembly that is coupled to the conduit from a different direction than the coupling assembly so that mechanical displacement signals from the at least one additional displacement signal source are coupled to the conduit from at least two of an X-direction, a Y-direction, a Z-direction, or an angle with respect to a longitudinal axis of the conduit and a desired acoustic or mechanical wave mode is generated during use to provide a desired controlled movement for at least one of an end region of the conduit and the tip of the conduit.

In at least one embodiment, operational parameters are selected to achieve controlled movement comprising a linear or non-linear motion in at least one of the Y-direction, the X-direction, and the Z-direction, a rotational movement, a torsional movement, a flexural movement or a pitch movement, a yaw movement or a tilting movement.

In at least one embodiment, the acoustic or mechanical wave mode may be selected to achieve a controlled cavitation at a desired location along the outside or the inside of the conduit.

In at least one embodiment, the acoustic or mechanical wave mode may be selected to generate a standing wave inside the conduit to translate entities obtained from the target site based on a characteristic of the entities including increasing size.

In at least one embodiment, the acoustic or mechanical wave mode may be selected to increase action at the tip of the conduit and decrease action at other portions of the conduit.

In at least one embodiment, the acoustic or mechanical wave mode may be selected to increase activity at a portion or tip of the conduit based on material and structural properties of the coupling assembly and the conduit and frequency of the mechanical displacement signal.

In at least one embodiment, the control unit may be configured to select at least one of a shape, a frequency, a repetition rate, a delay, an amplitude and a linearity or non-linearity of the displacement signal based on the location of the coupling point and the coupling angle to obtain a desired path of movement at a selected point on the conduit or at the tip of the conduit.

In at least one embodiment, the control unit may select the shape of the mechanical displacement signal based on selecting at least one of a pulse, a burst, an impulse, a whiplash, a chirp, a pre-defined noise, a random noise, a shock wave, a sine wave, a sawtooth wave, and a square wave.

The conduit generally provides a waveguide for delivering the mechanical displacement signal to the target site.

In at least one embodiment, the displacement signal source comprises at least one of a Langevin transducer, a flextensional piezo actuator, a piezo transducer, an electric spark gap, a pyrotechnic spark, an optically-induced plasma spark, a PMUT, a CMUT, an IDT, an RF source and a motor.

In at least one embodiment, the mechanical displacement signal may be generated to have a main frequency component or multiple frequency components in the range of about 0.1 Hz to 100 MHz, and more preferably in the range of about 10 to 200 kHz.

In at least one embodiment, a momentary or time-averaged intensity of the mechanical displacement signal is in the range of about 1 $mW/cm^2$ to 10 $kW/cm^2$, and more preferably in the range of about 0.1 to 100 $W/cm^2$.

In at least one embodiment, the mechanical displacement signal may be generated to have a main frequency component or multiple frequency components in the range of about 200 kHz to 20 MHz, with continuous waves or a duty cycle of at least 1%. In at least some of these embodiments, the device may be used to aid in cauterization or reduction in bleeding at the target site.

In at least one embodiment, at least one of an outside surface and an inner surface of the conduit may be coated or patterned to provide at least one of: (i) an antiseptic surface, (ii) enhancement of entity extraction, (iii) cavitation nucleation sites or (iv) modified interaction between the conduit and the target site and between the conduit and the extracted entity in order to provide at least one of better preservation of cells or to detach more cells when obtaining the entity by generating propagating mechanical solitons or spatially controlled cavitation.

In at least one embodiment, the outer surface of the conduit and certain parameters of the displacement signal source may be adapted to generate surface waves on the outer surface of the conduit or to actuate the tip of the conduit to reduce friction during insertion or extraction of the conduit at the target site.

In at least one embodiment, the distal end of the conduit may comprise an end portion having the tip and the tip includes a bevel that provides an additional stage of amplification for the mechanical displacement signal to achieve an action at the tip compared to another portion of the conduit. In at least some of these embodiments, the bevel may has a shape selected to achieve a desired acoustic or mechanical wave mode at the end portion of the conduit.

In at least one embodiment, the conduit may have a tubular wall with a sawtooth pattern on its outer surface or its inner surface and a flat bevel end portion.

In at least one embodiment, the conduit may have a tubular wall that is tapered and end portions of the tubular wall are curved to provide a wavy profile for the bevel.

In at least one embodiment, the bevel may have an average opening angle in the range of about 0.1-180° and more preferably in the range of about 5-45°.

In at least one embodiment, the conduit may comprise two concentric cylinders that each have beveled ends and separately receive the mechanical displacement signal so that a beveled end of the outer cylinder moves momentarily in a different direction than a beveled end of the inner cylinder for enhanced interaction between the conduit tip and the target site.

In at least one embodiment, the motion may comprise a horizontal direction parallel to a longitudinal axis of the conduit, a vertical direction with respect to the longitudinal axis of the conduit, a radial direction with respect to the longitudinal axis of the conduit.

In at least one embodiment, the conduit may be split vertically into two halves to allow for different motion in the different halves.

The device general further comprises a housing, and the mechanical displacement source and the pressure controller may be mounted to the housing, and a portion of the housing may provide a gripping area for allowing a user to handle the device during use.

In at least one embodiment, inner or outer surfaces of the conduit may comprise at least one of grooves, holes, dents, and patterns to provide cavitation nucleation sites during use.

In at least one embodiment, the conduit or the pressure controller may comprise at least one of an optical sensor, an electronic sensor, a pressure sensor or a chemical sensor to obtain measurements of at least one condition at the target site during use.

In at least one embodiment, the device may be operable to atomize or nebulize a given object and spray the atomized or nebulized given object onto a material surface or into a cavity.

In at least one embodiment, the action may comprise obtaining a first entity from the target site, the distal end of the conduit has an aperture that is disposed at the target site during use for obtaining the first entity therefrom, the pressure controller is configured to vary an amount of suction pressure in the conduit when obtaining the first entity, and the control unit is configured to implement the desired acoustic or mechanical wave mode at a portion of the conduit when obtaining the first entity from the target site.

In such an embodiment, the conduit may also act as a common channel for receiving the first entity from the target site.

In such an embodiment, the outer surface of the conduit and certain parameters of the displacement signal source may be adapted to generate surface waves on the outer surface of the conduit or to actuate the tip of the conduit to maintain aspirated entities intact when obtaining the entities.

In such an embodiment, the bevel may have a shape selected to achieve a desired entity extraction mechanism at the end portion of the conduit.

In such an embodiment, the distal end of the conduit may have a puncturing structure for penetrating and actuating the target site when obtaining the first entity.

In such an embodiment, the pressure controller may comprise a reservoir that is adapted to receive the first entity.

In such an embodiment, the pressure controller may comprise a conventional syringe coupled to a needle that provides the conduit and having a piston with a handle at one end for actuation of the syringe and a plunger at another end that is disposed in a reservoir of the syringe, the reservoir being adapted to receive the first entity.

In at least one embodiment, the action may comprise delivering a second entity to the target site, the distal end of the conduit has an aperture that is disposed at the target site during use for delivering the second entity therefrom, the pressure controller is configured to vary an amount of delivery pressure in the conduit when delivering the second entity, and the control unit is configured to implement the desired acoustic or mechanical wave mode at a portion of the conduit when delivering the second entity to the target site.

In such an embodiment, the conduit may also act a common channel for delivering the second entity to the target site.

In such an embodiment, the bevel may have a shape selected to achieve a desired entity delivery mechanism at the end portion of the conduit.

In such an embodiment, the distal end of the conduit may have a puncturing structure for penetrating and actuating the target site when delivering the second entity.

In such an embodiment, the pressure controller may comprise a reservoir that is adapted to store the second entity to be delivered to the target site.

In such an embodiment, the pressure controller may comprise a conventional syringe coupled to a needle that provides the conduit and having a piston with a handle at one end for actuation of the syringe and a plunger at another end that is disposed in a reservoir of the syringe, the reservoir being adapted to contain the second entity to be delivered to the target site In such an embodiment, the second entity that is delivered to the target site comprises one of a drug, a cell, a fixative, and a nanoparticle.

In at least one embodiment, the action may comprise obtaining a first entity from the target site or delivering a second entity to the target site, the distal end of the conduit has an aperture that is disposed at the target site during use for obtaining the first entity therefrom or delivering the second entity to the target site, the pressure controller is configured to vary an amount of suction pressure in the conduit when obtaining the first entity or vary an amount of delivery pressure in the conduit when delivering the second entity, and the control unit is configured to implement the desired acoustic or mechanical wave mode at a portion of the conduit when obtaining the first entity from the target site or delivering the second entity to the target site.

In such an embodiment, the conduit may also act a common channel for receiving the first entity from the target site or delivering the second entity to the target site.

In such an embodiment, the bevel may have a shape selected to achieve a desired entity extraction mechanism at the end portion of the conduit when sampling the first entity from the target site or to achieve a desired entity delivery mechanism when delivering the second entity to the target site.

In such an embodiment, the distal end of the conduit may have a puncturing structure for penetrating and actuating the target site when obtaining the first entity or delivering the second entity.

In such an embodiment, the pressure controller may comprise a reservoir that is adapted to receive the first entity during sampling or to hold the second entity prior to delivery.

In such an embodiment, the first entity may be sampled from the target site before the second entity is delivered to the target site.

In such an embodiment, the second entity may be delivered to the target site before the first entity is sampled from the target site.

In at least one embodiment, the device may comprise an inner member disposed within the conduit and separated from the inner surface of the conduit by a gap, the inner member comprising a reservoir, the conduit and inner member being sized to perform core needle biopsies and the mechanical displacement signal is coupled to at least one of the conduit and the inner member to cause relative motion between the conduit and the inner member.

In such embodiments, the reservoir of the inner member may further comprise a sharp corner and the inner member receives the mechanical displacement signal to cause an end portion of the inner member to extend past the conduit and allow the reservoir with the sharp corner to aid in performing a cutting motion at the target site.

In the embodiments described herein, the object comprises one of alive or dead flora, and alive or dead fauna.

In a broad aspect, at least one embodiment described herein provides a device for obtaining an entity from a target site of an object or delivering a second entity to the target site of the object. The device comprises a conduit having a proximal end and a distal end, the distal end having an aperture and being disposed at the target site of the object for obtaining the entity therefrom or delivering the second entity thereto during use; a displacement signal source for generating a mechanical displacement signal; a coupling assembly having a first end coupled to the displacement signal source and a second end coupled at a coupling point on the conduit between the proximal end and the distal end of the conduit, the coupling assembly being configured to couple the mechanical displacement signal to the conduit during use; a pressure controller coupled to the proximal end of the conduit and being configured to vary an amount of delivery pressure in the conduit during delivery of the second entity or an amount of suction pressure in the conduit during acquisition of the entity; and a control unit coupled to the displacement signal source for controlling the displacement signal source to generate the mechanical displacement signal based on the location of the coupling point and the coupling angle between the second end of the coupling assembly and the conduit to implement a desired acoustic or mechanical wave mode when obtaining the entity from the target site or delivering the second entity to the target site.

In a broad aspect, at least one embodiment described herein provides a method of obtaining a first entity from a target site of an object or delivering a second entity to the target site of the object, the method may comprise: placing a device at the target site, the device comprising: a conduit having a proximal end and a distal end, the distal end having an aperture that is disposed at the target site of the object for obtaining the first entity therefrom or delivering the second entity thereto during use; a displacement signal source disposed near the proximal end of the conduit; a coupling assembly for coupling the displacement signal source to the conduit at a coupling location and a coupling angle at a portion of the conduit; a pressure controller coupled to the proximal end of the conduit for varying an amount of pressure therein for delivery of the second entity or acquiring of the first entity; and a control unit coupled to the displacement signal source for controlling the displacement signal source; selecting a desired acoustic or mechanical wave mode for the displacement signal source based on at least one of the location of the coupling point and the coupling angle between the coupling assembly and the conduit to implement a desired mechanical displacement at a portion or a tip of the conduit when obtaining the first entity from the target site or delivering the second entity to the target site; and generating a mechanical displacement signal using the displacement signal source and the selected acoustic or mechanical wave mode to obtain the first entity from the target site or deliver the second entity to the target site.

In at least one embodiment, before generating the mechanical displacement signal, the method may comprise actuating the pressure controller to a first volume setting for a reservoir of the pressure controller; inserting the conduit into the target site; and actuating the pressure controller to a second volume setting for the reservoir of the pressure controller, the second volume being larger than the first volume.

In at least one embodiment, the mechanical displacement signal may be generated for a first time period after which the pressure controller is actuated to relieve decompression thereby obtaining the first entity from the target site, and the conduit is withdrawn from the target site.

In at least one embodiment, after withdrawing the conduit from the target site, the pressure controller may be actuated to eject the obtained first entity onto a glass slide or in a container.

In at least one embodiment, while generating the mechanical displacement signal, the method may comprise obtaining the first entity from the target site or delivering the second entity to the target site.

In at least one embodiment, while generating the mechanical displacement signal, the method may comprise inserting the conduit into the target site or removing the conduit from the target site.

In at least one embodiment, while generating the mechanical displacement signal, the method may comprise moving the device by hand or with robotics in order to achieve translation, tilting and/or rotation of the conduit or conduit tip within or outside of the target site.

In at least one embodiment, the desired acoustic or mechanical wave mode may be selected to actuate a proximal portion of the conduit, a distal end portion of the conduit or both the proximal and distal end portions of the conduit.

In at least one embodiment, the wave mode may be selected to cause different portions of the conduit to experience different wave modes or to perform different actions.

In at least one embodiment, before generating the mechanical displacement signal, the method may comprises: inserting the second entity into a reservoir of the device; actuating the pressure controller to a first volume setting for the reservoir of the pressure controller; inserting the conduit into the target site; and actuating the pressure controller to a second volume setting for the reservoir of the pressure controller, the second volume being smaller than the first volume to deliver the second entity to the target site.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings, which show at least one example embodiment, and which are now described. The drawings are not intended to limit the scope of the teachings described herein.

FIGS. 3A-3C show top, side and front views of an example embodiment of a prototype of a sampling device in accordance with the teachings herein.

FIGS. 10A-10B show the experimental setup used to test for cavitation effects in water during sonication at different power levels.

FIGS. 10C-10E show light scattering imaged with a microscope at different voltage levels for the function generator.

Figure 1A:
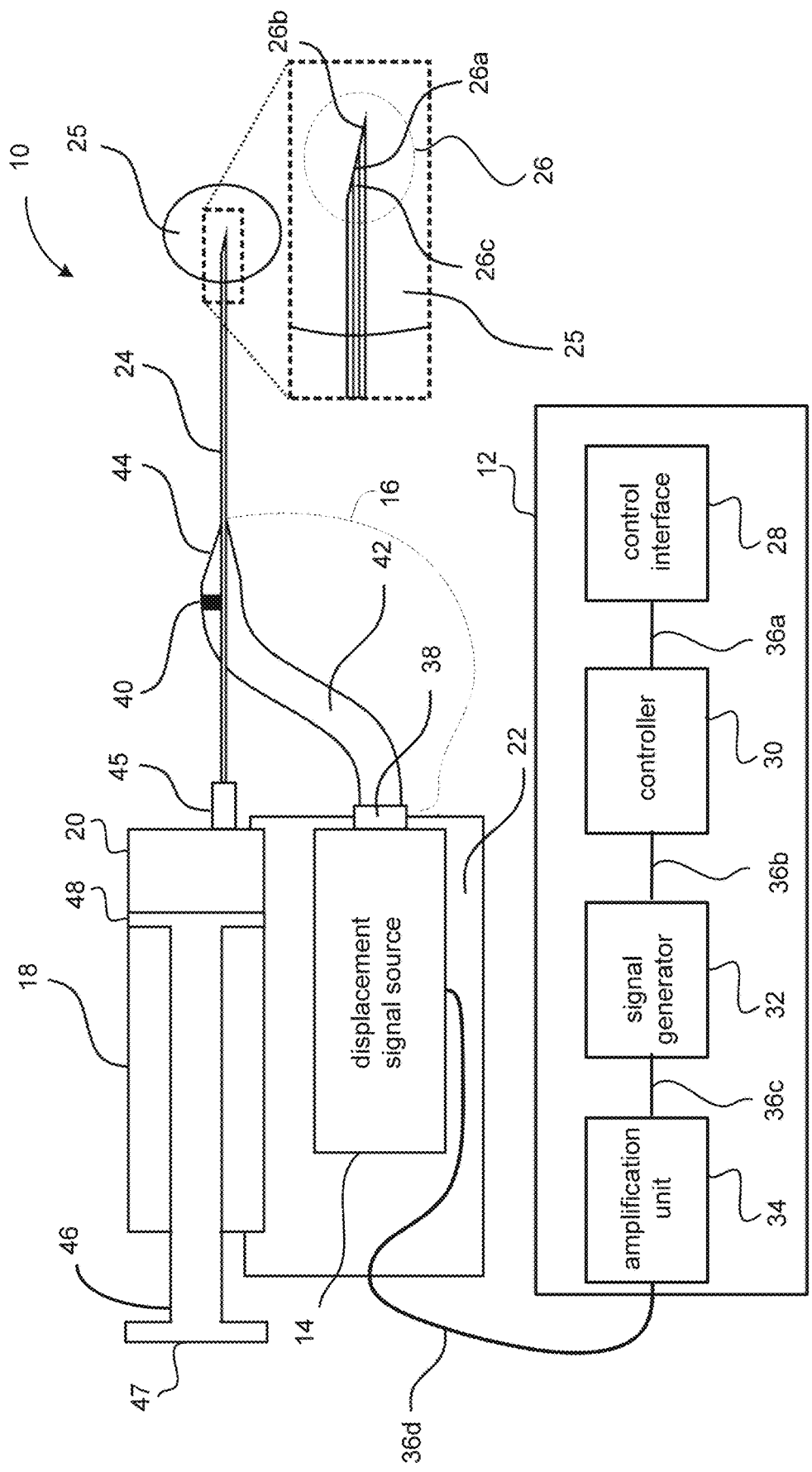
FIG. 1A is a block diagram of an example embodiment of an ultrasound-based tissue extraction system in accordance with the teachings herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices or methods having all of the features of any one of the devices or methods described below or to features common to multiple or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or acoustic connotation. For example, as used herein, the terms coupled or coupling can indicate that two elements or devices can be directly connected to one another or connected to one another through one or more intermediate elements or devices via an electrical signal, a mechanical element, such as, conduits and the like or acoustic signals, such as ultrasound vibrations depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as 1%, 2%, 5% or 10%, if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5% or 10%, for example.

A major part of in vitro diagnostics relies on extraction of tissue and cells from potentially pathologic tissues such as tumors. The obtained sample may be used to diagnose the pathology of the tissue of interest or to evaluate the effectiveness of a therapy, e.g. drug treatment, in modifying tissue pathologies such as sarcomas, tumors, and other lesions. Samples, such as tissue samples, for example, are commonly extracted from the body also in the field of personalized medicine, e.g. in autologous chondrocyte transplantation and tissue engineering. In these examples, cells are extracted from the body (e.g. articular cartilage), grown in a bioreactor, and inserted back into the body in larger quantities with or without modified properties (e.g. modified DNA). A key issue is to acquire an adequate sample volume that contains an adequate number of cells while preserving the sample, i.e. neither modifying the tissue and cell structure nor the function of the cells and the tissue.

High-intensity ultrasound (HIU) displaces material at the nano/micrometer scale in tissue or other objects. By applying high-intensity ultrasound to a needle which propagates towards the needle tip, the sound can move (translate/rotate) the needle tip rapidly several micro-meters at a high frequency (e.g. 35 kHz). The needle tip motion can thus actuate tissue, or other materials, by using certain mechanisms such as one or more of compressive force, tensile force, shear force, torsional force, flexural force, cavitation, radiation force, and acoustic streaming, for example, to extract/loosen cells from the target tissue or target material. However, known ultrasound techniques are not designed to extract samples in a cell-preserving and tissue architecture preserving manner for in-vitro diagnostic purposes or to be used in conjunction with conventional syringes and hypodermic needles.

According to the teachings herein, at least one example embodiment of the sampling/delivery devices described herein can be made in a cost-effective manner and can extract a large volume of sample while preserving the extracted cells and the structure/architecture of the sample, such as tissue structure/architecture, for example, in comparison with conventional techniques. This may be achieved by applying a displacement signal, which may be a mechanical or acoustic wave, to a conduit, such as a needle, in such a way that a high amplitude and controlled motion (e.g. displacement) can be achieved at the tip of the conduit, e.g. a needle tip, to loosen cells in a target site when the sampling device is inserted into the target site such as, but not limited to, a tumor or articular cartilage, for example. During the procedure the conduit may be connected to a pressure control unit which simultaneously applies a low pressure while the sample is being acquired so that the loosened cells and possibly tissue constructs are collected into at least one of a hollow center of the conduit or a chamber within the pressure control unit.

It should be noted that while the devices described in accordance with the teachings herein are mainly described as a sampling device for ease of illustration the sampling device can also be used and referred to as a delivery device by changing some of the operational parameters as discussed herein for certain use case scenarios.

Mechanical or acoustic waves travelling along the outer surface of the conduit of the sampling device may also contribute to overcoming or reducing any friction forces or hydraulic resistance of the conduit when penetrating the target site. This may enable the use of fine needles as the conduit, even at deep target sites for obtaining certain types of cells, such as, but not limited to, pressure sensitive cells, for example. A similar kind of displacement signal may be generated to travel along the inner surface of the conduit thereby reducing hydraulic resistance inside the conduit which may make it easier to suction in a larger amount of cells from the target site while maintaining the overall anatomy/architecture of the extracted sample.

In one aspect, in at least one of the example embodiments of the sampling device described in accordance with the teachings herein, a larger sample volume may be extracted from the target site as compared to FNA. In addition, the tip of the conduit may be controlled with a greater precision and accuracy by using certain mechanical displacement signals when obtaining a sample from the target site. This increased control and greater sampling volume may lead to the use of smaller conduit tips. The increased control may appear as smaller inter-user or intra-user variability in e.g. sample volume as compared to FNA, since FNA requires highly subjective hand motion by the operator whereas the technology represented by the embodiments described herein do not necessarily require subjective hand motion. An example of the enhancement in intra-user variability is demonstrated by data presented in FIG. 6B. Accordingly, there is at least one embodiment of the sampling device that may be used in non-invasive procedures outside of a surgical setting, e.g. in a general practitioner's office.

It should be noted that the terms mechanical displacement signals or displacement signals refer to signals that are generated by a displacement source and that are coupled to a conduit for transmission along the conduit, via an external and/or internal surface thereof, to an end of the conduit to perform a certain action at the end of the conduit such as sampling from a target site or delivery of an entity to the target site. Examples of a displacement signal include, but are not limited to, an acoustic wave, a mechanical wave or strain due to applied stress. The acoustic wave may be at various frequencies including ultrasonic frequencies. The terms displacement signal and mechanical displacement signal are equivalent to one another. In addition, sound and ultrasound are examples of acoustic waves. Furthermore, it should be noted that acoustic or mechanical wave modes can be resonant modes. The modifier "acoustic or mechanical" which may apply to e.g. waves, pressure, stress, intensity, energy or modes is used herein since the movement of the conduit may be due to i. acoustic or mechanical waves, ii. acoustic and mechanical waves or iii. strain.

In another aspect, at least one embodiment of the sampling device described in accordance with the teachings herein may be configured to minimize trauma and damage to cells, tissues and other areas outside of a target site, such as a biopsy site, and to control the amount and type of extracted sample. For example, the acoustic or mechanical waves propagating along the conduit may be controlled to be quite low in intensity (e.g. <1 W/cm$^2$). Therefore, the acoustic or mechanical waves do not interfere or damage the environment surrounding the conduit, which is important for patient safety when used on living humans or animals especially because the conduits used for obtaining tissue samples may need to be very long and located adjacent to sensitive organs within the patient's body. However, when the acoustic or mechanical wave energy propagates to the converging bevel at the tip of the conduit, the acoustic or mechanical wave energy can be greatly amplified geometrically, because the same power in the conduit is concentrated in a smaller cross-sectional area. Thus, a high intensity (>1 W/cm$^2$) and high displacement (>1 µm) motion may be achieved at the very tip of the conduit. This intensity and motion is strong enough to cut/scrape out cells/tissue constructs/cores. Thus, the acoustic/mechanical structure of the sampling device has 1) structural simplicity, 2) is easy to manufacture, 3) has a low cost, and 4) increased patient safety since greater actuation only needs to occur at the conduit tip where a sample needs to be taken. For tissue sample acquisition, this also provides for great spatial accuracy, because the conduit tip of the sampling device, if desired, needs not to be moved about as in conventional FNA.

It should be noted that the target site to which the various sampling devices described herein are applied is part of an object. The object may be alive or dead flora or fauna including humans and animals. The humans or animals may be patients or test subjects. In other cases, the object may be engineering materials such as, but not limited to, polymers, nanomaterials, biomaterials, nano-composites, ceramics, dialysis membranes, highly viscous fluids, textiles, or paper pulp, for example. In still other cases, the object may be a food product such as, but not limited to, dairy products such as cheese, meat products, fish products, and vegetable products, for example. In still other cases, the object may be a natural material such as, but not limited to, clay, soil, and sandstone, for example.

Potential applications for at least one example embodiment of a sampling device described in accordance with the teachings herein may include, but are not limited to, at least one of histology, in vitro diagnostics, bone marrow extraction, bone extraction, cytology, imaging and micro-imaging of tissue, tissue engineering, drug delivery (especially localized) and micro-tissue stimulation, for example. In the case of micro-tissue stimulation, US may be used to stimulate or down regulate local tissues by using specific US frequencies and other characteristics in effect performing US "acupuncture". Another embodiment may involve micro or nanostructured material which may be stimulated according to the teachings herein to change properties such as shape, permeability and the like, in a momentary/reversible or permanent/irreversible manner.

In at least one embodiment of the sampling device described in accordance with the teachings herein, displacement signals, e.g. mechanical waves, acoustic waves or strain (e.g. compressional, tensile, shear or torsional) due to applied stress, having at least one frequency, which are emitted from a displacement signal source are coupled as an input signal to a conduit, such as a needle, and transmitted through or along the conduit towards the a distal end portion of the conduit, e.g. the needle end/tip. In at least some cases, the needle may be a hypodermic needle. The distal end of the conduit has a puncturing structure to penetrate and actuate the target site during entity acquisition. The geometry of the conduit end portion may be tapered such that it amplifies and alters the displacement signals that are transmitted to it. Thus, high pressure/displacement amplitudes as well as predetermined tip trajectories may be achieved at the conduit end portion. Depending on the coupling of the mechanical or acoustic waves to the conduit, mechanical or acoustic waves according to a mechanical or acoustic wave mode propagate within or along the conduit and/or conduit end portion and can be at least one of, but are not limited to, longitudinal, shear, flexural, Lamb, quasi-Lamb, Scholte, Stoneley, Love, Rayleigh, Franz, or torsional waves, for example. These waves can be travelling waves or standing waves and may be preferably flexural waves or longitudinal waves. For example, the size and shape of a single coupler or a multitude of couplers connected to the same conduit can be used to generate acoustic or mechanical wave modes in the conduit that are beneficial for a certain desired action at the tip and end potion of the conduit. The input displacement signal may be a continuous wave, a pulse, or a burst with constant or dynamically varying amplitude or with constant or dynamically varying frequency or with constant or dynamically varying phase that propagates in a linear or non-linear fashion. When an embodiment uses acoustic waves that are ultrasonic, i.e. exceeding 20 kHz, the embodiment may be referred to as "Ultrasound-enhanced fine-needle aspiration", i.e. USeFNA.

Referring now to FIG. 1A, shown therein is an example embodiment of a sampling device 10 according to the teachings herein. The sampling device 10 comprises a control unit 12, a displacement signal source 14, a coupling assembly 16, a pressure controller 18, a reservoir 20, a housing 22 and a conduit 24 with a conduit end portion 25. The housing 22 provides a gripping area for the sampling device 10 that may be held by a user, such as a medical practitioner, during operation. The housing 22 also protects several internal components of the sampling device 10 and also provides a platform for the mechanical connection of certain components of the sampling device 10. The user may use the sampling device 10 to obtain an anatomical sample from a target site and/or to provide a substance to a target site, as is described in more detail below. The target site may correspond to a patient, an animal, a deceased individual or an object or material.

The control unit 12 comprises a control interface 28, a controller 30, a signal generator 32, and an amplification unit 34. Electrical connections 36a, 36b and 36c couple the components of the control unit 12 to one another while electrical connector 36d couples the control unit 12 to the displacement signal source 14. A power supply, which is not shown but is known to those skilled in the art, is coupled to the control unit 12 to provide power thereto. The power supply can be a battery, a rechargeable battery, or a converter coupled to an AC power source. Electrical connections 36a and 36b can be replaced with wireless connections (e.g. electromagnetic or acoustic) in some embodiments.

The control interface 28 receives inputs from a user to control the operation of the sampling device 10. The control interface 28 can include a display and possibly at least one of a mouse, a keyboard, a thumbwheel, a track-pad, a track-ball, footswitch, optical or acoustic sensors, such as movement and proximity sensors, and the like. In some cases, the display of the control interface 28 can be a touch screen, which can function as an input means.

The controller 30 controls the operation of the sampling device 10 and can comprise any suitable processor, controller or digital signal processor (DSP) that can provide sufficient processing power as is known by those skilled in the art. For example, the controller 30 may be a high performance general processor. In alternative embodiments, the controller 30 may include more than one processor with each processor being configured to perform different dedicated tasks. In alternative embodiments, specialized hardware can be used, such as Application Specific Integrated Circuits (ASICs), to provide some of the functions provided by the controller 30.

The signal generator 32 generates an electrical drive signal that is provided to the displacement signal source 14 to drive the displacement signal source 14 to generate acoustic or mechanical waves that are then converted to a mechanical displacement signal along the conduit 24 and end portion 25. The signal generator 32 can control the amplitude and frequency content of the drive signal so that the mechanical displacement signal is generated according to a desired acoustic or mechanical wave mode, which is explained in more detail below, to allow for fine control of a tip 26 of the conduit end portion 25. The signal generator 32 may be implemented using a DSP along with a digital to analog converter (DAC), using discrete electrical analog and digital components or a combination of a DSP, a DAC and discrete electrical components. In an alternative embodiment, the functionality of the signal generator 32 may be provided by the controller 30 which digitally generates the drive signal that is then converted to an analog drive signal via a DAC.

The power amplification unit 34 amplifies the drive signal provided by the signal generator 32 so that it has sufficient current and voltage to drive the displacement signal source 14 to generate the desired mechanical displacement signals for propagation along the conduit 24 of the sampling device 10. Accordingly, the amplification unit 34 includes analog circuitry for providing the amplification, which may include operational amplifiers, transistors, resistors, inductors and capacitors arranged in a certain circuit configuration in order to provide the desired amplification as is known by those skilled in the art.

The control unit 12 may be implemented as being part of the sampling device 10 and may be portable. Alternatively, in other embodiments, the control unit 12 may be provided by a computing device such as a desktop computer, a laptop, a tablet computer, a mobile communication device, a headset and the like.

In an example embodiment, the displacement signal source 14, which may also be referred to as a mechanical displacement source, an acoustic wave source or a strain source, is a Langevin transducer meaning that the displacement signal source 14 comprises an ultrasound-emitting transducer (e.g. a piezo-electric transducer) and at least one acoustic resonator and/or horn to amplify the sound generated by the piezo-electric transducer. Alternatively, in other embodiments, the displacement signal source 14 can be a flextensional piezo actuator. In other embodiments, the displacement signal source 14 includes at least one of a piezo (e.g. flat or focused element or transducer array), an electric spark gap, a pyrotechnic spark, an optically-induced plasma spark, a CMUT (capacitive micromachined ultrasonic transducer), a PMUT (piezo-electric micromachined ultrasonic transducer), an IDT (inter-digital transducer), an RF source (based on electrostriction, magnetostriction or induction), a flextensional transducer, a motor or any other equivalent source of acoustic or mechanical waves or strain. In such cases, the power amplification unit 34 and the signal generator 32 can be replaced by units specifically optimized for driving the particular mechanical displacement source that is used.

The mechanical energy that is generated by the displacement signal source 14 can have a main frequency (e.g. sinusoidal) or multiple frequencies (e.g. broadband) in the range of about 0.1 Hz-100 MHz, and more preferably from about 10-200 kHz. To achieve e.g. thermal or acoustic radiation force effects, higher frequencies of about 200 kHz to 20 MHz may be used. The momentary or time-averaged intensity of the generated acoustic or mechanical wave can be in the range of about 1 mW/cm$^2$-10 kW/cm$^2$, and more preferably in the range of about 0.1-100 W/cm$^2$. The generated mechanical energy can include pulses, bursts, or continuous waves and the temporal relationships between parameters such as pressure, density, displacement and particle velocity can be linear or non-linear. The envelope, frequency content and amplitude of the generated acoustic waves can be modulated temporally or spatially by any known or arbitrary function. For example, modulation may be used to achieve "pulsating" radiation forces.

In some embodiments, the displacement signal source 14 may comprise a multitude of transducer types or a multitude of transducers with different orientation angles with respect to the conduit 24 in order to use acoustic or mechanical wave mode control to achieve a desired action at the conduit tip 26 and conduit end portion 25 which is beneficial for the particular application of the sampling device 10. Acoustic or mechanical wave mode control is further discussed in relation to FIGS. 4A-4G herein.

The coupling assembly 16 comprises acoustic/mechanical couplers 38 and 40, a waveguide 42 and a converging structure 44. The acoustic/mechanical couplers 38 and 40 are acoustic impedance matching elements that are used to couple a first end of the waveguide 42 to the displacement signal source 14 and a second end of the waveguide 42 to the conduit 24. The acoustic/mechanical couplers 38 and 40 may be made of material that provides electrical isolation between the displacement signal source and the conduit 24 thereby providing enhanced electrical safety. Different means or fasteners may be used to attach the acoustic/mechanical couplers 38 and 40 to either end of the waveguide 42 such as, but not limited to, screws, quick-locks or threads or adhesion means (e.g. glue, ionic or covalent bond), for example. The acoustic and mechanical impedances of the acoustic/mechanical couplers 38 and 40, the conduit 24 and the displacement signal source 14 can be similar for energy efficient transmission of waves from one element to another and for acoustic/mechanical coupling to the waveguide 42.

The length and shape of the waveguide 42 can be matched with desired acoustic/mechanical wave modes that will be used in practice to induce resonances within the waveguide 42 in order to generate desired action (e.g. a desired amount and/or type of mechanical displacement) at the conduit tip 26 and the conduit end portion 25, which is beneficial for the particular application of the sampling device 10. A resonance can be achieved in a structure whose length in a dimension is in proportion to the wavelength's fraction propagating along that dimension. For example, in a straight waveguide, a desired resonance may be achieved when the length of a "half open" waveguide is $n \times \frac{1}{4} \times$ the wavelength or the acoustic or mechanical wave, where n is a positive integer. Material selection affects the speed of an acoustic or mechanical wave of a desired acoustic or mechanical wave mode. The size and shape of the waveguide 42 may be used to amplify the displacement at a certain location of the waveguide 42. A tapered structure may also be used to amplify the displacement.

The waveguide 42 can be of any size, shape, and material that can be selected to achieve geometric amplification and control of an intended displacement at the end portion 25 and tip 26 of the conduit 24 for efficient loosening of cells while, at will, preserving the relative order, structure, and function of these cells and not generating excess damage to the surrounding areas of the target site, such as surrounding tissues, for example. An example of such an embodiment is presented in FIG. 1A.

The mechanical or acoustic impedance of the waveguide 42 is preferably close to those of the acoustic/mechanical couplers 38 and 40 and/or the displacement signal source 14. This is to achieve efficient transfer of mechanical or acoustic waves from the displacement signal source 14 to the acoustic/mechanical couplers 38 and 40 and, potentially, to avoid or to reduce standing waves in the conduit 24 when they are unwanted. However, in at least some of the embodiments according to the teachings herein, it may be desirable to exploit standing waves of intended acoustic or mechanical wave modes to achieve large displacements of the conduit tip 26 for maximal dynamic range in displacement. In some embodiments the entire waveguide 42 is extracorporeal, but in some embodiments the waveguide 42 may be within the object where the target site is situated.

In embodiments in which the displacement signal source 14 includes a hot electrode, the conduit 24 needs to be electrically isolated from the hot electrode to avoid providing an electric shock to the patient. However, in embodiments in which electric actuation, e.g. RF ablation or cauterization of tissue, is intended, the electric current can be passed to and through the conduit 24 to the target site. In this case an electrically grounded electrode or grounded separate needle, parallel or near to the conduit 24, can be used to avoid leakage of the electric current into the target site or to avoid providing an electric shock to the target site when the target site is part of a living entity such as a patient or an animal. Exposed regions of the conduit 24, and any additional needles that may be used, may be coated with electrically isolating material for enhanced safety.

An optional converging structure 44, which may be integral with the waveguide 42, provides a first stage of geometric amplification to the energy that is received from the waveguide 42 and propagates the amplified wave energy towards the conduit tip 26. The amplification is provided e.g. in the flexural or longitudinal mode for frequencies typically >1 kHz. When the amplified mechanical or acoustic wave reaches the conduit tip 26, the energy of the wave and thus, also the particle (e.g. molecule) displacement associated with the mechanical or acoustic wave energy within the structure of the conduit 24 undergo a second stage of geometric amplification that is provided by a converging structure 26b at the end of the conduit tip 26. In this embodiment, the tubular sides 26a of the conduit 24 provide a bevel as the converging structure 26b that provides the further amplification to the mechanical or acoustic wave energy as well as a channel 26c to receive sample cells that are displaced at the target site due to the acoustic or mechanical wave energy that is provided thereto during use.

The conduit 24 can be made from various medical grade materials such as, but not limited to, stainless steel, brass, nitinol, MRI compatible metals, silicon, polymer, or ceramic, for example. The conduit 24 may also be coated using various materials such as, but not limited to, nickel-plated, PTFE, Parylene, ceramic, silicon nitride, gold, carbon, diamond, or drugs, for example. Alternatively, in some embodiments the conduit 24 may be non-coated. The topology of the conduit 24 can be selected depending on the particular application of the device 10. In this example embodiment, the conduit 24 includes the hollow channel 26c, and angled walls 26a and 26b to form a bevel.

In one example embodiment, the conduit 24 may be a disposable hypodermic needle that is made of coated or non-coated stainless steel, and has an outer needle diameter that is at least 150 μm, and preferably gauge 14-34 (i.e. nominal outer diameter 0.184-2.11 mm). The hypodermic needle may have one or multiple cores. In embodiments where there is a double core, one core may be used to deliver an agent or entity to the target site and the second core may be used to extract an entity or sample from the target site. The agent may be drugs or cells or other materials. In other embodiments, other types of needles may be used.

In at least one embodiment, the outside and/or inner surfaces of the conduit 24 can be coated or patterned to provide at least one of: (i) an antiseptic surface, (ii) enhancement of sample extraction, (iii) cavitation nucleation sites or (iv) modified interaction between the conduit 24 and the cells at the target site as well as between the conduit 24 and the extracted sample for various purposes such as, but not limited to, better preservation of cells if desired or to detach more cells during the cell extraction procedure, for example. In some embodiments, more cells may be detached by generating propagating mechanical solitons or spatially controlled cavitation by creating or trapping air pockets into patterns that are used at the inner and/or outer surface of the end portion 25 of the conduit 24 or at the outer or inner surface of the conduit 24. More particularly, the inner or outer surfaces of the conduit may include at least one of grooves, holes, dents, and patterns to provide the nucleation sites during use. In some embodiments, cells can be extracted and a different application can be applied to the cells after extraction from the target site, such that the cells (such as tissue cells or cells of other material) may be disrupted in a controlled manner to yield cell components having a particular size, and certain properties.

In one aspect of the teachings herein, the modified interaction between the conduit 24 and the tissue at the target site and/or between the conduit 24 and the extracted sample may be achieved by using different shapes for the inner surface of the conduit, the outer surface of the conduit 24 and/or the beveled end portion 25 and configuring the displacement signal source 24 to generate certain acoustic or mechanical waves. For example, in at least one example embodiment according to the teachings herein, the outer surface of the conduit 24 and the displacement signal source 14 may be adapted to generate surface waves (also known as leaky waves) on the outer surface of the conduit 24 that may be used to reduce friction during insertion/extraction of the conduit 24 at the target site and act as 'sonic lubrication', i.e. non-chemical reduction of friction by acoustic or mechanical waves, as well as to maintain the aspirated sample cells intact during aspiration.

In another aspect according to the teachings herein, the bevel shape can be designed to control or modify or amplify a desired acoustic or mechanical wave mode or sample extraction mechanism at the end portion 25 of the conduit 24. Example embodiments for different conduit end portions and bevels with various shapes are shown in FIGS. 1B-1G and 1M (side views) and FIGS. 1H-1K (top views).

Figure 1B:
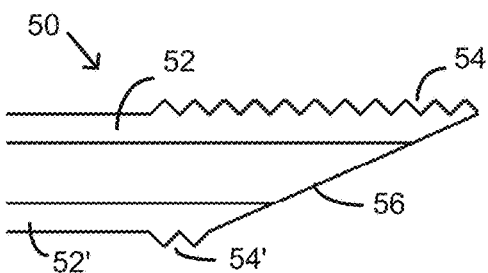
FIGS. 1B-1L show various example embodiments for an end portion of a conduit that may be used with the device of FIG. 1A.
Figure 1C:
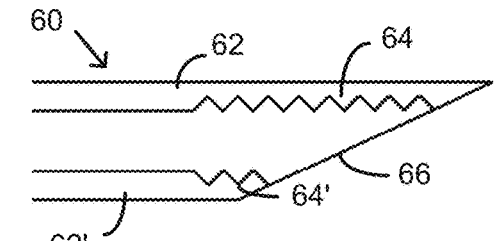

For example, FIG. 1B shows a conduit 50 having a tubular wall 52 with a sawtooth pattern 54 on its outer surface and a flat bevel end portion 56. It should be understood that the sawtooth pattern 54 extends around the exterior circumference of the conduit 50 but since a portion of the tubular wall 52 of the conduit 50 has been removed the sawtooth pattern 54 has a tapered portion 54'. In an alternative embodiment, shown in FIG. 1C, a conduit 60 may have a tubular wall 62 with a sawtooth pattern 64 on its inner surface and a flat bevel end portion 66. The sawtooth pattern 64 extends around the interior circumference of the conduit 60 and has a tapered portion 64'.

Figure 1D:
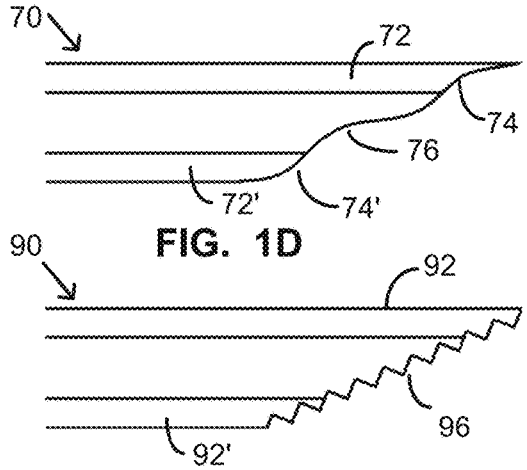

Referring now to FIG. 1D, shown therein is an alternative embodiment of a conduit 70 that has a tubular wall that is tapered so that it transitions from a longer wall 72 to a shorter wall 72' and end portions 74 and 74' respectively of the walls 72 and 72' are curved such that the bevel 76 has a wavy or sinusoidal profile to achieve zones that apply different amounts of force to the target site such as, for example, higher pre-stress between the convex areas on the needle bevel and the target site compared to concave areas on the needle bevel and the target site.

Figure 1E:
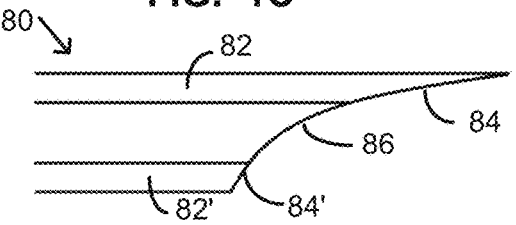

Referring now to FIG. 1E, shown therein is an alternative embodiment of a conduit 80 that has a tubular structure that has an opening that is tapered so that it transitions from a longer wall 84 to a shorter wall 84' and the end portions of the walls are curved such that the bevel 86 has a single or multiple adjacent semi-concave or exponentially converging profiles. This structure enables very high displacement amplitudes to be achieved at the distal end of the bevel 86 compared to the proximal end of the bevel 86. In alternative embodiments, the end portions of the wall 84 can be shaped so that the bevel 86 can have a fuller concave profile or a different radius of curvature.

Figure 1F:
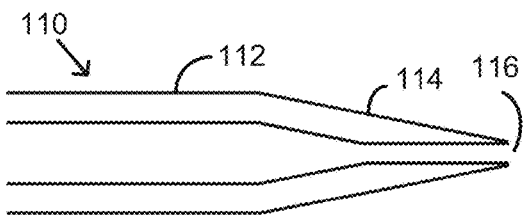

Referring now to FIG. 1F, shown therein is an alternative embodiment of a conduit 90 that has a tubular wall that is tapered so that it transitions from a longer wall 94 to a shorter wall 94' and the end portions of the walls are shaped such that the bevel 96 has a stepped, granular or sawtooth profile. This structure achieves multiple contact points or stress points (e.g. 3-$10^9$ at one bevel with a surface area of 2 mm$^2$) with the target site with high stress prior to and during bevel movement. A bevel with 3 stress points may correspond to a stepped or sawtooth profile whereas a bevel with approximately 1,000 stress points may correspond to a granular profile or a micro-roughness profile and a bevel with approximately $10^9$ stress points may correspond to a nano-roughness profile.

Figure 1G:
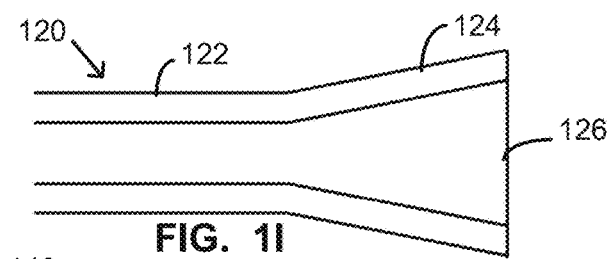

Referring now to FIG. 1G, shown therein is an alternative embodiment of a conduit 100 that has a tubular wall 102 that is jagged so that it has an upper portion 104 and a lower portion 104' that have large spike shapes such that the bevel 106 is multi-tipped. This structure achieves multiple actuation points at the bevel end with high material displacement amplitude.

Figure 1H:
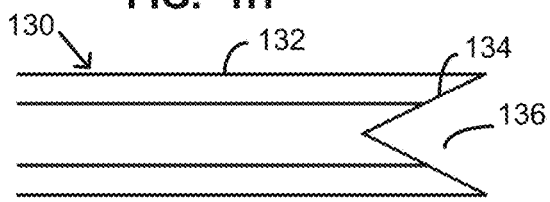

Referring now to FIG. 1H, shown therein is an alternative embodiment of a conduit 110 that has a tubular wall 112 that has an end portion 114 that is tapered inwards so that the bevel is a converging structure and has a conical shaped profile. This structure allows for actuation at the proximity of the opening 116 of the conduit 110.

Figure 1I:
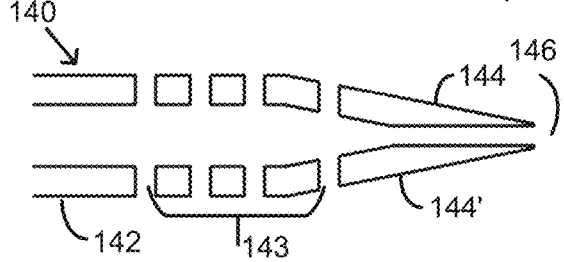

Referring now to FIG. 1I, shown therein is an alternative embodiment of a conduit 120 that has a tubular wall 122 that has an end portion 124 with sidewalls that are flared outwards or are diverging so that the end portion 126 has a horned or funnel shaped profile with a flat edge. The diverging structure can be simultaneously converging when observed from another viewing angle to obtain (similar to what is presented in FIG. 1H, for example) a large displacement at the bevel end, but have a large contact area between the target site and the bevel. This may be used for obtaining samples from linear tissue structures such as vessels and nerves, for example.

Figure 1J:
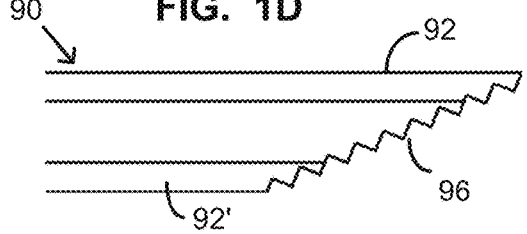

Referring now to FIG. 1J, shown therein is an alternative embodiment of a conduit 130 that has a tubular wall 132 that has a notch 134 at its end portion such that the bevel 136 has a triangular or V-shaped profile. This may be used to achieve large displacements uniformly at all points on the outer edge of the conduit bevel, for example.

Figure 1K:
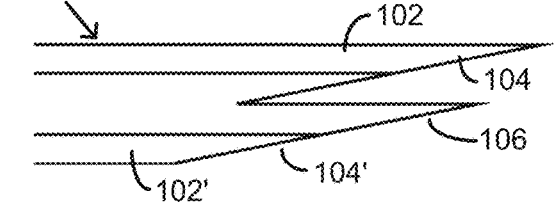

Referring now to FIG. 1K, shown therein is an alternative embodiment of a conduit 140 that has a tubular wall with a solid portion 142, an aerated portion 143 with various openings, and an end portion 144 with walls that are tapered inwards to form a converging structure having a conical shape for the bevel 146. This structure permits inflow of material from the target site into the inner part of the conduit 140 from multiple points in the proximity of the conduit end portion or the bevel. In alternative embodiments, the aerated portion 143 may have different patterns of openings such as a grid-like pattern or a spiral pattern or a different number of openings such as one, two, or three or more.

Figure 1L:
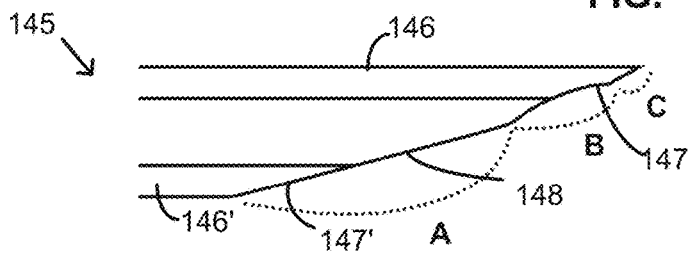
Figure 1M:
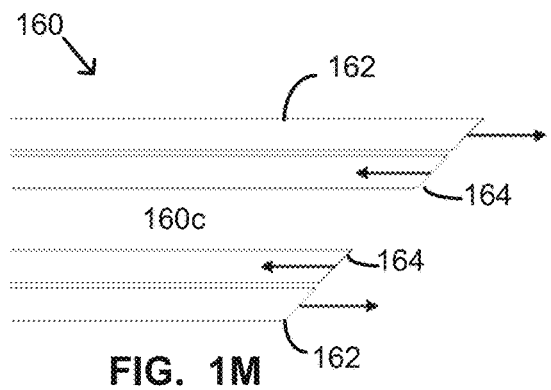
FIGS. 1M-1P show another example embodiment for an end portion of a conduit that comprises two concentric cylinders that may experience different movement depending on the acoustic energy that they receive during use.
Figure 1N:
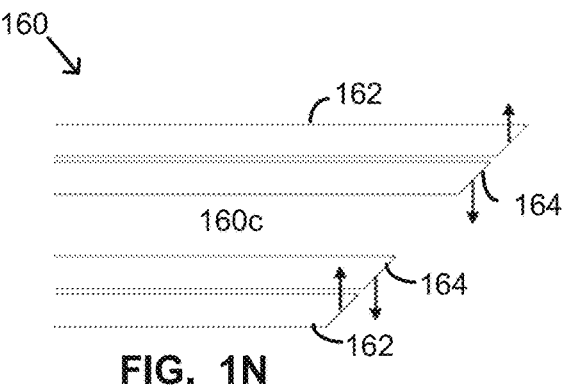
Figure 1O:
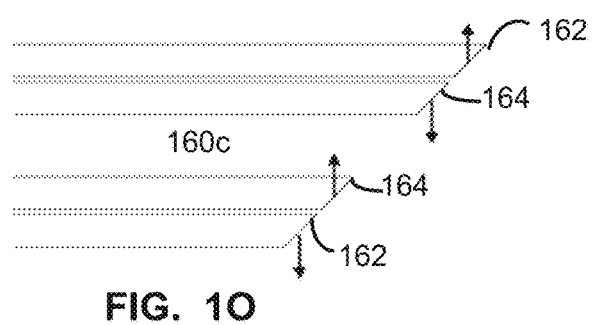

Referring now to FIG. 1L, shown therein is an alternative embodiment of a conduit 145 that has a tubular wall that is tapered so that it transitions from a longer wall 146 to a shorter wall 146'. The tip of the conduit 145 has edges 147' and 148 that are linear or straight (as identified by region A) whereas the edge 147 has a concave-like portion and a straight portion identified by regions B and C, respectively. Accordingly, the conduit 145 may be described as having a stepped bevel with multiple tip segments A, B and C. This bevel has a relatively thin tube wall near tip region B and does not converge rapidly while converging rapidly in segment C as compared with the bevel of FIG. 1E, for example. This provides a relatively high amplitude motion near the needle tip (at regions B and C), but is potentially more durable (i.e. does not crack that easily) than other very thin bevel ends such as the bevel in FIG. 1E. The conduit 145 may be considered to have a profile with zones that apply different amounts of force to the target site such as, for example, higher pre-stress between the convex-like areas on the needle bevel (i.e. near the boundaries between sections A and B or sections B and C or near the needle end) and the target site compared to concave-like areas (i.e. the central part of sections A, B or C) on the needle bevel and the target site.

The various shapes for the end portions and bevels of the different conduit embodiments may be used to detach cells selectively by one or more of cell type, cell size, cell shape, cell orientation, cell pathology, cell count, cell type or any other property of the cell or any property of embedding structures and materials. This may be achieved since different bevel geometries are expected to produce different kinds of actuation since the bevel geometry is expected to change the displacements at different parts of the conduit and bevel. Furthermore, different tissues react differently to USeFNA (as discovered by the inventors). Therefore, it is expected that the quality of the samples may be different depending on the bevel properties.

In general, the bevel of the conduit end portion 25 may have an average opening angle that can range from about 0.1-180° (0.1° corresponds to a very sharp tip, 180° corresponds to a flat-ended tip), and may be preferably in the range of about 5-45°. The term average opening is used as the angle may be difficult to define for stepped or sawtooth-like bevels or bevels with roughness but can be considered to be the angle defined by the wall edges of the conduit that converge at the tip of the conduit. As shown in FIGS. 1B-1L, the bevel shape is convergent for most embodiments and can be converging linearly or exponentially at a certain rate. The bevel shape can have a geometry that can be expressed by a known function or an arbitrary function.

Furthermore, depending on the shape of the bevel, for some embodiments, the pressure and displacement amplitudes of the conduit 24 are greatest at the tip 26, especially at 26b, or end portion 25 of the conduit 24 and more particularly at the sharp corners or edges of the needle bevel structures 26b, especially when the opening angle of the bevel is small.

Furthermore, in another aspect, in at least one embodiment described in accordance with the teachings herein, the motion of the conduit tip 26 during use may be controlled or uncontrolled to exert different types of force or actions at the target site such as, but not limited to, cutting, tearing, gripping, pinching, compressional, tensile, shear, flexural, peristaltic, and torsional forces, for example. In addition, the magnitude of these forces may be controlled by configuring the displacement signal source 14 to generate certain acoustic or mechanical waves and by having a particular shape for the conduit end portion 25 so that sufficient force and/or stress is applied at the target site to detach objects e.g. desired cell constructs at the target site such as, but not limited to, cells, groups of cells, clusters of cells, or extracellular tissue matrix such as fibers, or tissue fragments or soft/hard tissue cores for certain objects, for example. The tissue fragments may include but are not limited to one or more of pathologies (e.g. sarcomas, tumors, or any other tissue lesions); tissues (e.g. soft tissue such as breast, thyroid, prostate, articular cartilage, fibrocartilage, tendons, ligaments, liver, pancreas, brain, nerves, eye, muscles, bladder, kidney, heart, bone marrow; lining tissues and mucosa such as skin, gastrointestinal (e.g. oral, pharyngeal, esophagus, stomach small intestine, large intestine, gall bladder, bile ducts); respiratory (e.g. lung, laryngeal, bronchial, small airways); urinary (e.g. ureter, bladder, urethra); female genital tract [endometrium, cervix, vagina]) and hard tissues (e.g. compact bone, porous bone, subchondral bone or other calcified tissues), for example. In practice, compressional, tensile, shear and torsional forces in the target site near the needle end can be achieved when the displacement signal source 14 comprises an ultrasound sandwich transducer that produces a longitudinal wave generating a flexural or longitudinal motion near converging structure 44 of the waveguide 42 to achieve flexural or longitudinal standing wave motion in the conduit 24 to achieve a high amplitude displacement motion at the bevel 26b. The magnitude of displacement is generally >1 µm, and is preferably >10 µm for some applications. In some conditions, e.g. at a low fundamental resonant frequency of the conduit 24, the magnitude of the displacement can be e.g. >1 mm during flexural motion.

Referring back to FIG. 1A, the conduit 24 may be connected to the sampling device 10 by a connector 45, which may be an aluminum or polypropylene hub, for example, to a pressure controller 18. The connector 45 has an aperture to allow for the flow of sample from the target site through the conduit 24 towards the pressure controller 18 or the flow of a drug to the conduit 24 and then to the target site. The pressure controller 18 comprises a pressure actuator 46 that may be operated to apply a low pressure (i.e. a suction pressure) through the conduit 24 to obtain the sample or to apply a high pressure (i.e. a delivery pressure) to the conduit 24 to deliver a drug or other entity to the target site.

In at least one example embodiment, the pressure controller 18 may be implemented using a conventional syringe with a piston that operates as the actuator 46. The piston comprises a handle 47 to allow a user to operate the piston by either pushing towards the conduit 24 or pulling the piston away from the conduit 24. The piston also includes a head or plunger 48 that is used to interact with the contents of the reservoir 20. In alternative embodiments, a gas/water pump or a piezo-electric pico-pump may be used instead of the piston.

In use, a low pressure may be applied by pulling the piston which achieves suction in the hollow structure/channel of the conduit 24 and in the proximity of the conduit end portion 25 and tip 26 when the conduit end portion 25 is within an object, e.g. the target tissue. This then induces a suction or peristaltic translation of detached tissue constructs from the target tissue site into the channel 26c of the conduit end portion 25 and, potentially, into the reservoir 20 within the pressure controller 18. It should be noted while the example embodiments are described herein terms of being used with a target tissue, there can be other target objects that the embodiments can be used with.

In at least one example embodiment, the conduit 24 or the reservoir 20 comprises at least one of an optical sensor, an electronic sensor or a chemical sensor to obtain measurements of at least one condition at the target site during use of a relevant parameter such as, but not limited to pH, blood sugar, pressure, and oxygen saturation, depending on the type of sensor(s) used.

The mechanical or acoustic waves emitted by the structures of the needle end portion 25 and the conduit tip 26, in accordance with the teachings herein, can generate non-linear acoustic phenomena e.g. acoustic streaming, acoustic radiation force and cavitation, inside the target site, which contributes to detaching cellular constituents from the target site depending on the object where the target site resides. Moreover, the target site may be modified by mechanical or acoustic waves before, during or after the cell extraction procedure for diagnostic or therapeutic purposes. In practice, the structure of the target site may be modified, for example, for enhanced penetration of drugs or fixatives for therapy or diagnostic purposes, respectively, in certain use case scenarios. Mechanical or acoustic waves may contribute to overcoming or reducing the friction or hydraulic resistance of a long thin conduit when penetrating the target site or to enhance extraction of cells. This action may then enable the use of fine conduits/needles at even deeper sites for obtaining different types of cells, such as pressure sensitive cells, for example. In another aspect, in at least some embodiments, the lowered penetration resistance may contribute to reduced pain sensation at the skin level or at or near the target site when the object is a living person or animal. This feature may be advantageous for various procedures such as, but not limited to, pain-free tattooing of agents, e.g. drugs, contrast agents, or soft electrodes, into the skin or other tissues.

In some embodiments, such as those shown in FIGS. 1M to 1P and 1R, the conduit 160 may comprise two concentric cylinders 162 and 164 that both have beveled ends with the inner cylinder 164 having a channel 160c. Each of the cylinders 162 and 164 are connected to separate waveguides to separately receive acoustic or mechanical wave energy in such a manner that any part of the conduit 160, preferably the bevel of the outer cylinder 162, moves momentarily in a different direction than the inner cylinder 164 for enhanced needle interaction with the tissue at the target site, e.g. for more efficient loosening of the cells that are to be sampled.

Figure 1P:
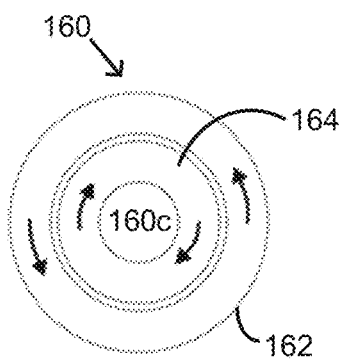

The motion can be e.g. horizontal i.e. in a direction parallel to the central longitudinal axis of the conduit 160 (see FIG. 1M), in a vertical direction with respect to the central longitudinal axis of the conduit 160 (see FIG. 1N), in a radial direction with respect to the central longitudinal axis of the conduit 160 (see FIG. 1O) or in a torsional direction (see FIG. 1P).

Figure 1Q:
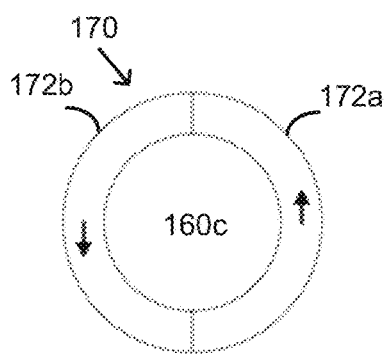
FIGS. 1Q-1R show other example embodiments for an end portion of a conduit that comprises cylindrical elements that are made of two separate parts.
Figure 1R:
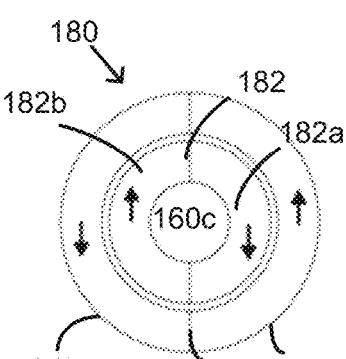
Figure 1S:
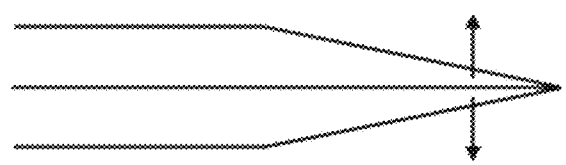
FIG. 1S shows another example embodiment for an end portion of a conduit (top view) that comprises cylindrical elements split vertically into two separate parts.

In an alternative embodiment, a single needle 170 can be split vertically to have different motion in the different needle halves 172a and 172b (see FIG. 1Q). This may be used in a concentric needle 180 which comprises first and second needles 182 and 184 that are concentric and similarly split vertically to have different parts 182a and 182b as well as different parts 184a and 184b, respectively, which may move differently with respect to one another (see FIG. 1R).

The previously mentioned configurations of the conduits 160, 170 and 180 of FIGS. 1M-1S are provided as examples and the number and locations of the needle splits, the number of concentric cylinders and needle tips, and the directions and motion (e.g. amplitude, direction, acoustic or mechanical wave mode) of the needle are not limited to what is shown herein. Furthermore, in some embodiments, the configurations covered by FIGS. 1M-1S may be combined with the example configurations shown in FIGS. 1A-1L.

Figure 2A:
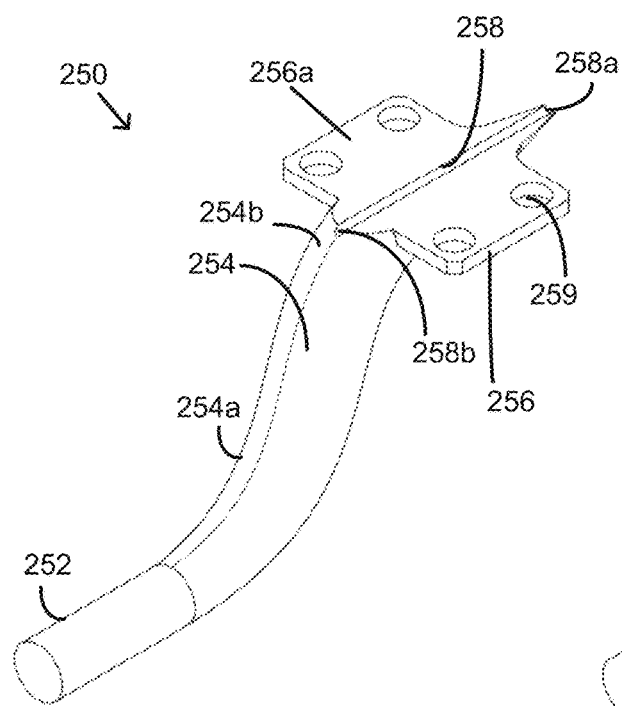
FIGS. 2A-2B show rear and front perspective views of a first portion of a waveguide in one example embodiment for use with the device of FIG. 1A.
Figure 2B:
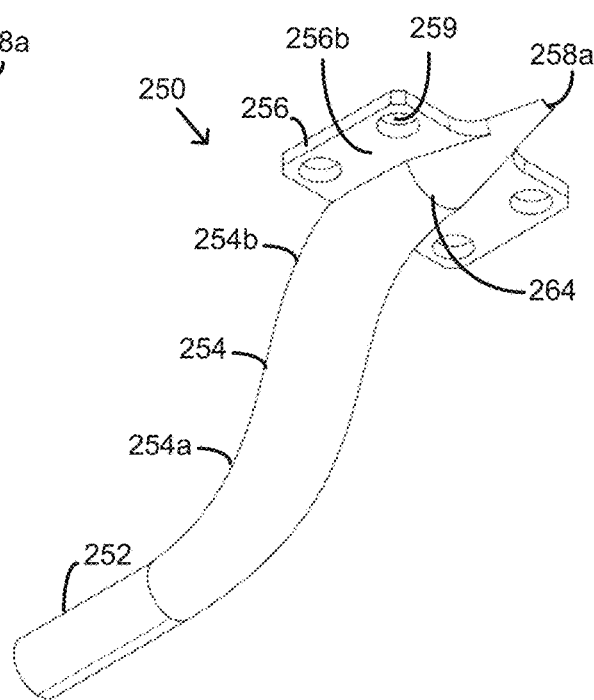

Referring now to FIGS. 2A-2B, shown therein are rear and front perspective views, respectively, of a first portion of a waveguide 250 in one example embodiment according to the teachings herein. The coupling assembly 250 comprises a first coupling region 252 for coupling with the acoustic/mechanical coupler 38, a transition region 254 and a second coupling region 256 for coupling with the acoustic/mechanical coupler 40 and the conduit 24.

The end portion 254a of the transition region 254 that is nearest the first coupling region 252 of the waveguide portion 250 has a different longitudinal axis than the longitudinal axis of the transition region 254 and the longitudinal axis of the displacement signal source 14 (in this case the end portion 254a is curved but it may not be curved in other embodiments) so that the acoustic or mechanical wave energy from the displacement signal source 14 can be more efficiently transmitted to the straight transition region 254. Likewise, the end portion 254b of the transition region 254 that is nearest the second coupling region 256 also has a longitudinal axis that is different from the longitudinal axis of the transition region 254 (in this case the end portion 254b is curved but it may not be curved in other embodiments) to guide acoustic or mechanical waves from the transition region 254 to the second coupling region 256. It should be noted that in some embodiments the end portions 254a and 254b can have similar curvatures. When intended, the waveguide portion 250 provides high amplitude flexural-like (vertical) motion or longitudinal motion at 258 or 258a depending on the type of displacement signal that is generated by the displacement signal source 14. The combination of the waveguide portions 250 and 260 (see FIGS. 2C-2D) permits firm compression around the portion of the conduit 24 that is within grooves 258 and 268 (when assembled) using e.g. screws passing through holes 259 and 266 in order to achieve energy-efficient transmission of acoustic or mechanical waves from the waveguide 250 to the conduit 24.

In this example embodiment, the second coupling region 256 is shaped like a plate having an upper surface 256a and a lower surface 256b, a channel 258 with a first end region 258a and a second end region 258b and several apertures 259 (only one of which is labelled for simplicity). The channel 258 is shaped to receive a lower circumferential portion of conduit 24.

The lower portion of the second coupling region 264 is conical to form a lower portion 264 of a converging structure of the waveguide 254 that works with a corresponding converging portion on an upper waveguide portion 260 to amplify the acoustic or wave energy that is transferred from the waveguide 254 to the conduit 24. When designed to be optimal for the application in question, this arrangement provides high amplitude flexural-like (i.e. vertical) motion (e.g. extraction of an aspirate) or longitudinal-like motion (e.g. extraction of soft tissue core) at 258 or 258a to achieve a standing flexural wave in the conduit 24. For drug delivery, the wave mode within the conduit 24 is expected to change the sound field near the needle. This may enable changing the sound field (e.g. direction or intensity distribution) and, therefore, the direction and location of drug delivery.

Figure 2C:
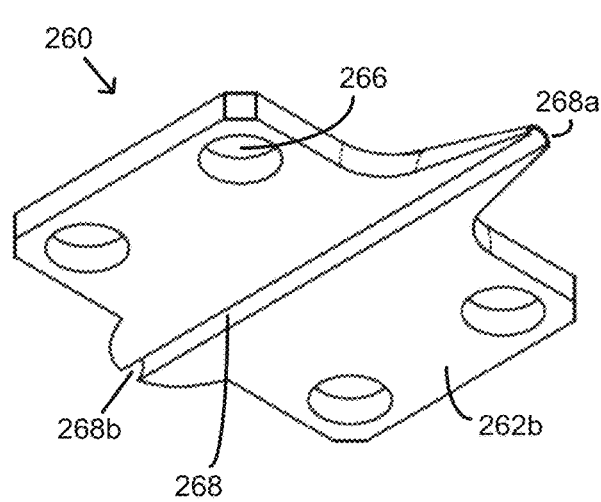
FIGS. 2C-2D show lower and upper perspective views of a second portion of the waveguide of FIG. 2A in one example embodiment.
Figure 2D:
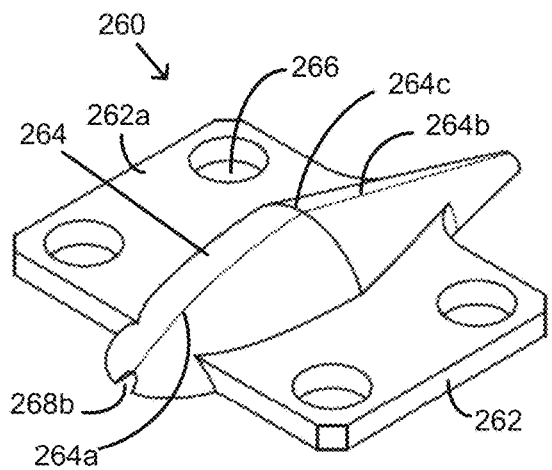

Referring now to FIGS. 2C-2D, shown therein are lower and upper perspective views of a second waveguide portion 260 in one example embodiment. The second waveguide portion 260 has a main body 262 shaped like a plate having an upper surface 262a and a lower surface 262b. The second waveguide portion 260 also comprises an upper portion 264 of a converging structure, a channel 268 and apertures 266 (only one of which is labelled for simplicity).

The channel 268 is sized to receive an upper circumferential portion of the conduit 24. The longitudinal axis of the channel 268 is aligned with the longitudinal axis of the channel 258 of the first waveguide portion 250. Likewise, the locations of the apertures 266 correspond to the location of the apertures 259 of the first waveguide portion so that the apertures 259 and 266 can receive fasteners after the conduit 24 has been placed into the channels 258 and 268.

The upper portion 264 of the converging structure has a first region 264a that has a conical shape that is flared outwards from a first end portion 268b of the channel 268 to a mid-portion 264c of the upper portion 264 of the converging structure. On the other side of the mid-portion, the upper portion 264 of the converging structure has a second region 264b which is similarly shaped to the first region 264a but opposite in disposition so that the second region has a tapered conical shape that tapers inwards from the mid-portion 264c to a second end portion 268a of the channel 268. When intended, this arrangement provides high amplitude flexural-like (vertical) motion at 268a to achieve a standing flexural wave in the conduit 24.

Referring now to FIGS. 3A-3C, shown therein are top, side and front views of an example embodiment of a portion of a prototype of a sampling device 300 in accordance with the teachings herein. In this example prototype, the sampling device 300 comprises a coupling assembly 316, a pressure controller 318, a reservoir 320, a housing 322 and a conduit 324 with a conduit end portion 325 and a conduit tip 326. The coupling assembly 316 comprises acoustic couplers 338 and 340, a waveguide 342 and a converging structure 344. The conduit 324 is connected to the sampling device 300 by a connector 345, which may be an aluminum or polypropylene hub, for example, to the pressure controller 318. The pressure controller 318 comprises a pressure actuator 346 that may be operated to apply a low pressure (typically lower than the pressure of the operational environment, e.g. <1 atm or a lower pressure than in the object, e.g. target tissue) through the conduit 324 to obtain the sample or to apply a high pressure (typically higher than pressure of the operation environment, e.g. >1 atm, or higher pressure than in the object, e.g. target tissue) to the conduit 324 to deliver a drug or other entity to the target site. In this example embodiment, the pressure controller 318 is a conventional syringe with a piston that comprises a handle 327 and a plunger 348. This embodiment, together with the transmission of flexural standing wave motion to the conduit 324 with high amplitude displacements (e.g. >1 μm) at the conduit tip 326, enables for efficiently obtaining samples from the target site. The acoustic impedance of the coupler 342 needs to be sufficiently low to obtain large material displacements within the coupling assembly 316. The transducer enclosed within the housing 322 was connected to a power amplifier, which was connected to a signal generator unit.

Figure 3D:
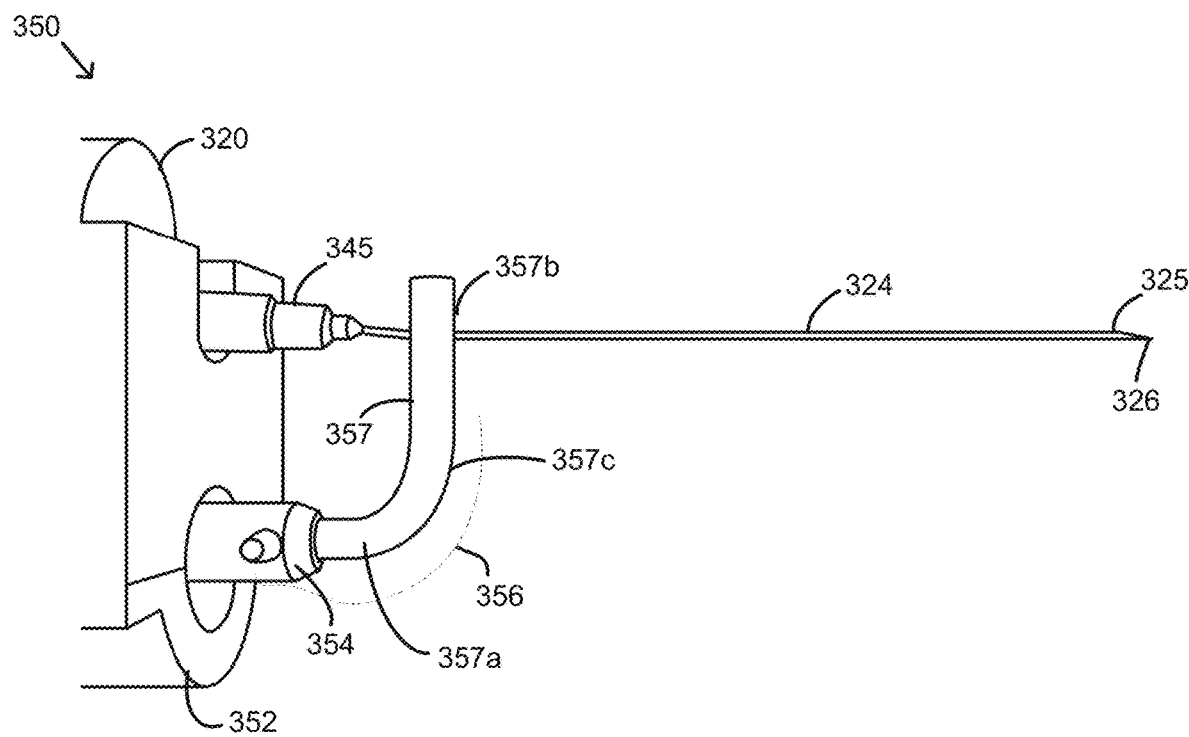
FIG. 3D shows a side view of an example embodiment of another prototype of a sampling device in accordance with the teachings herein.

Referring now to FIG. 3D, shown therein is a side view of an example embodiment of a portion of another prototype of a sampling device 350 in accordance with the teachings herein. Some of the elements of the sampling device 350 are similar to those of sampling device 300 and are numbered similarly. Housing 352 is similar to housing 322. However, the sampling device 350 has a different coupling assembly 356. The coupling assembly 356 has a "J" shape whereas the coupling assembly 316 of the device 300 has a stretched "S" shape. The coupling assembly 356 comprises a first coupler 354, and a waveguide 357 with a first end portion 357a, a second end portion 357b, a transition region 357c where the orientation of the central longitudinal axis of the waveguide 357 changes so that acoustic or mechanical wave energy from the displacement signal source is guided and coupled to the conduit 324 from an end 357e of the waveguide 357.

Figure 3E:
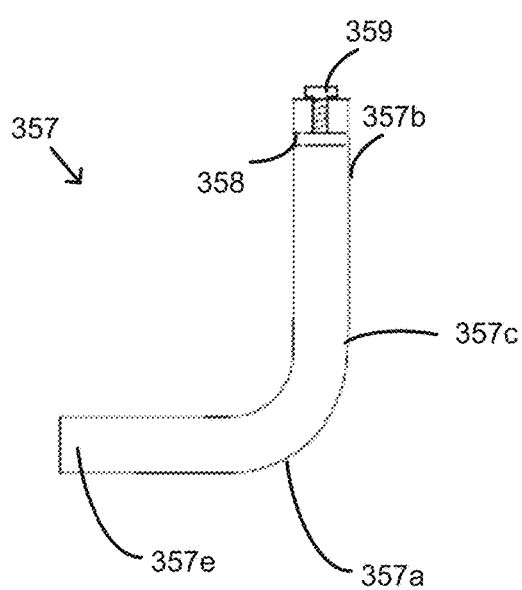
FIG. 3E shows a cross-sectional view of the waveguide of the coupling assembly of FIG. 3D.

The waveguide 357 comprises a channel 358 to receive a portion of the conduit 324 and a fastener 359, such as a screw, for firmly holding the waveguide 357 and the conduit 324 in mechanical contact with one another. This is better shown in FIG. 3E which shows a cross-sectional view of the waveguide 357. In this view, the fastener 359 is in an open position and after the conduit 324 is received within the channel 358, the fastener 359 is tightened to a closed position (in which the top of the fastener may not be seen from a side view (as shown in FIG. 3D). In some cases, the screw may not have an enlarged head. The end 357e of the waveguide 357 is received within an aperture (not shown) of the coupler 354 which maintains the waveguide 357 and the displacement signal source (not shown) in mechanical contact with one another. The shape of the waveguide 357 may allow for certain acoustic or mechanical wave modes to be enabled during use; e.g. the eigenmodes depend on the shape and speed of the mechanical waves in the waveguide material.

Figure 4A:
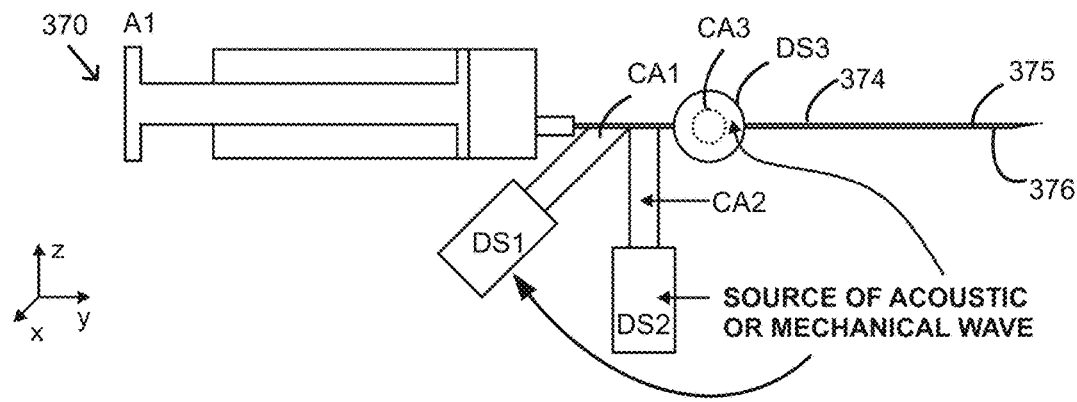
FIGS. 4A-4C shows examples of different ways to couple at least one displacement signal source to the conduit of the sampling device in order to achieve mechanical or acoustic wave mode control for obtaining desired mechanical displacements at the tip of the conduit.

Referring now to FIG. 4A, shown therein is an example embodiment A1 showing the different ways of coupling displacement signal sources DS1, DS2 or DS3 via coupling assemblies CA1, CA2 or CA3, respectively, to the conduit 374 of a sampling device 370 in order to achieve acoustic or mechanical wave mode control for the displacement energy at the end portion 375 and tip 376 of the conduit 374. In either case, the displacement signal sources DS1, DS2 or DS3 generates acoustic or mechanical waves that are made to propagate to the corresponding coupling assembly CA1, CA2 or CA3 in a direction that is typically non-parallel with the longitudinal central-axis of the conduit 374. In this example embodiment, only one of the displacement signal sources DS1, DS2 or DS3 is coupled to the conduit 374. In general, when a given coupling assembly contacts the conduit 374 at an angle, as is the case for the displacement signal source DS1 and coupling assembly CA1, the intended acoustic or mechanical wave mode generation can be achieved using a single displacement signal source and a single coupling assembly. The angle can be selected to enhance the acoustic or mechanical wave modes that are beneficial for achieving desired needle tip action and material displacement during use. For example, in some cases, actuation perpendicular to the longitudinal center axis of the conduit may more efficiently generate flexural waves than actuation in the direction of the longitudinal center axis of the conduit.

Figure 4B:
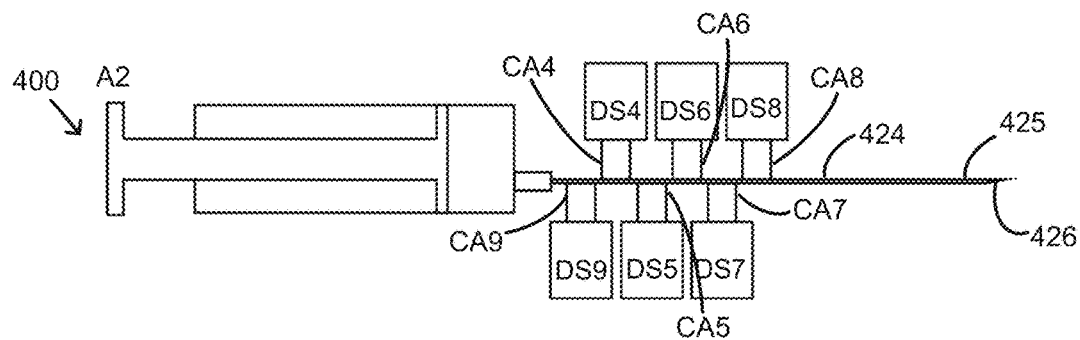
Figure 4C:
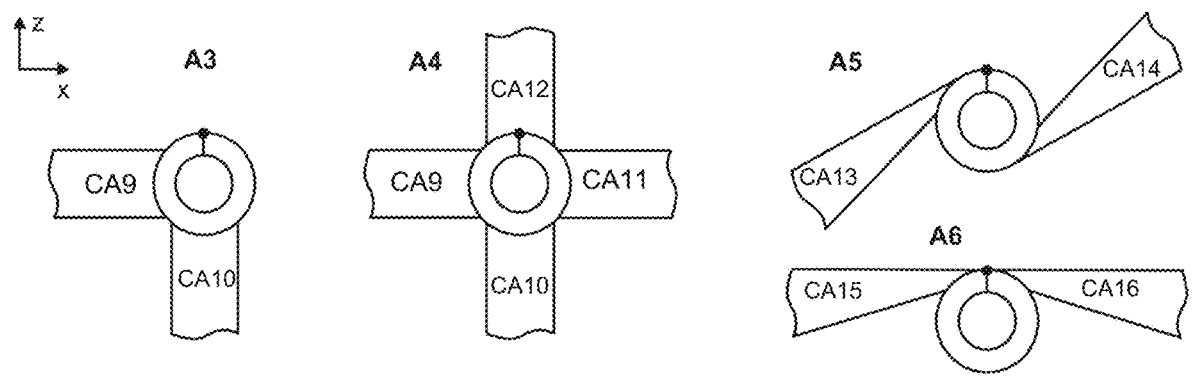
Figure 4D:
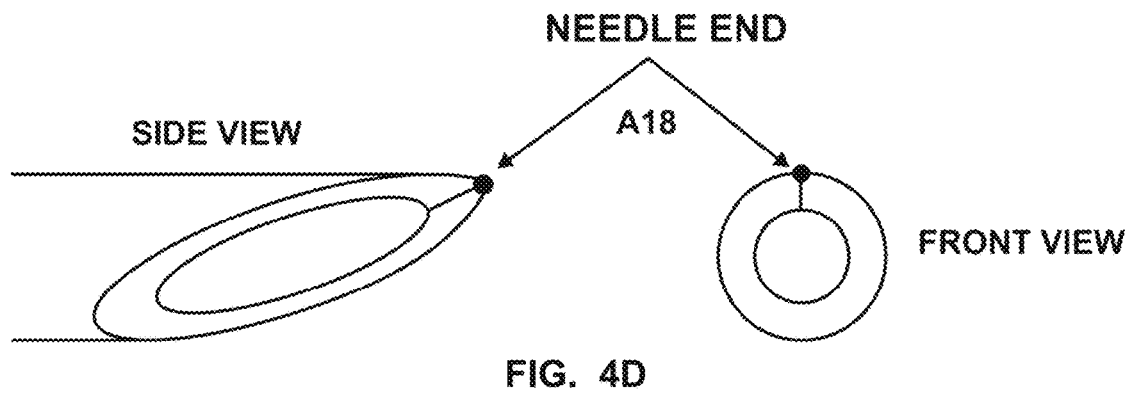
FIG. 4D shows side and front views of an example embodiment of a conduit tip having a beveled end.
Figure 4E:
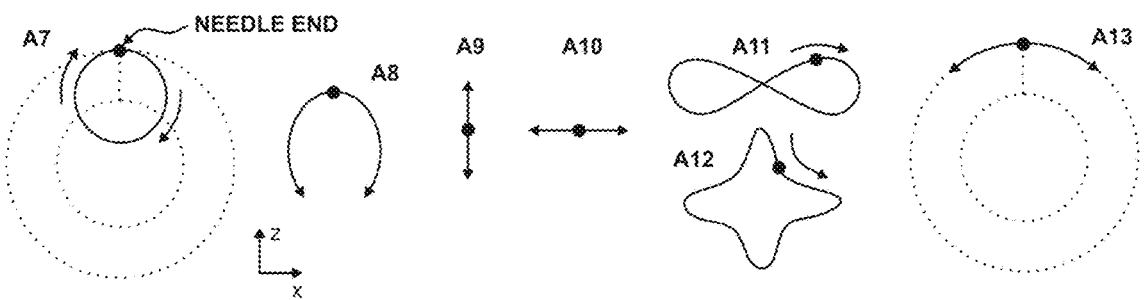
FIGS. 4E-4F show examples of different motions of the conduit tip due to acoustic or mechanical wave mode control.
Figure 4F:
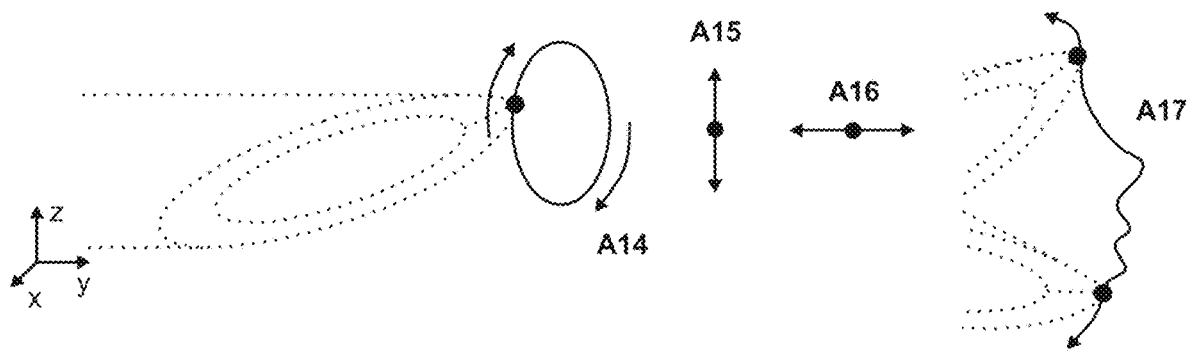

In embodiments in which multiple displacement signal sources and multiple coupling assemblies are introduced to the conduit from different directions, e.g. at least two of the x-direction, the y-direction, the z-direction, (see examples A3, A4 in FIG. 4C) or at an angle (see A1 in FIG. 4A), acoustic or mechanical wave modes can be generated, which at a selected point of the conduit can provide controlled movement as shown in examples A7-A17 of FIGS. 4E-4F. This point of controlled movement can be selected to be the end portion of the conduit 375 and/or the conduit tip 376 (see example A18 in FIG. 4D) or a point on the sharp edge or flat area of the bevel of the conduit tip or at any other desired point on the conduit. For example, a frequency for the mechanical displacement signal, which may or may not be a resonant frequency corresponding to an eigenmode of the conduit, can be selected from a group of frequencies to maximize the motion at an intended location along the conduit shaft and/or near the end portion of the conduit.

Referring now to FIG. 4B, shown therein is one example embodiment that enables acoustic or mechanical wave mode control by placing two or more displacement signal sources DS4 to DS9 and corresponding coupling assemblies CA4 to CA9 in a row. The couplers CA4 to CA9 can be physically the same or different (e.g. they may have the same or different materials, shapes, and sizes). The displacement signal sources DS4 to DS9 may produce sequential or combined displacement impulses with time delays to achieve enhancement of an intended acoustic or mechanical wave mode.

Referring now to FIG. 4C, a coupler assembly can also contact the needle surface tangentially (see examples A5-A6) to create acoustic or mechanical wave modes on the outer or inner surface of the conduit. This approach can be used to, for example, achieve torsional motion of the conduit 24 in a propagating or standing wave fashion (see FIG. 1P or 4E, for example). Sinusoidal signals may be used to drive the displacement signal sources, for example. In the case of multiple displacement signal sources and waveguides, the driving signals can be sequential or simultaneous (in phase or out of phase) with respect to one another.

It should be noted that in FIGS. 4C to 4F, the dot indicates the tip of the conduit and the line joining the inner and outer surfaces of the conduit indicates the "separation line" of two different surfaces which might not be parallel where they meet. A lancet typically has a two sharp blades which meet near the tip of the conduit.

In at least one example embodiment in accordance with the teachings herein, acoustic and/or mechanical wave mode control may be achieved by electronically controlling the displacement signal sources, which enables tissue-dependent and/or application-dependent selection of motion trajectories at different points along the conduit. For example, depending on the coupling location where the coupling assembly is coupled to the conduit and depending on the coupling angle at this location, a shape for the acoustic or mechanical wave may be selected (e.g. pulse, burst, continuous wave, impulse, whiplash, chirp, pre-defined noise, random noise, shock wave, sine, sawtooth, square/boxcar), as well as one of more of a main frequency or several frequencies of operation, a wave repetition rate, a delay, an amplitude and a linearity/non-linearity, a desired displacement trajectory can be obtained at a selected point on the conduit.

The selection of the wave type depends on the kind of motion that is desired at certain portions of the conduit. For example, a short pulse (e.g. a pulse, impulse, or shock wave) may be selected to have momentary action at the conduit tip. A short pulse has broadband frequency content, which may make the conduit also resonate at multiple frequencies. Alternatively, if it is desired to make the conduit resonate at a specific frequency, it might sometimes be more preferred to use a long bursts or continuous waves with a selected frequency, which has narrow band frequency content, which is advantageous as selecting one frequency may allow for the excitation of flexural resonant modes (i.e. a standing wave), while selecting another particular frequency may excite a longitudinal resonance mode.

For instance, considering example embodiment A3 in FIG. 4C, coupling assemblies CA9 and CA10 are coupled at the same or different longitudinal position on the conduit and the displacement signal sources can produce sinusoidal flexural motion, typically simultaneously, on the conduit to produce Lissajou patterns. For example, if the flexural motion at the coupling point is sinusoidal and the frequency and phase of both motions are the same along the Z and X axes and the displacement amplitudes can be the same or different along these axes, a diagonal-like displacement motion can be generated on the X-Z plane at the coupling point.

As another example, if the temporal phase difference is π/2 between the signals generated by the two displacement signal sources and the displacement amplitudes (i.e. intensity from the displacement signal sources) of the flexural waves are the same, a circular or torsional motion at the coupling point is generated (for example, see FIG. 1P and embodiment A13 in FIG. 4E). As yet another example, if the displacement amplitudes are different, then elliptic motion can be generated. If the displacement amplitude on the X-axes is zero, then linear motion along the Z-axis can be generated. If the displacement amplitude on the Z-axes is zero, then linear motion along X-axis can be generated. In another embodiment with a third displacement signal source and a third coupling assembly in addition to the first and second displacement signal sources and first and second coupling assemblies, displacement motion can be generated on the Y-axis, the previous displacement motions can be generalized for displacement motion control of the needle tip in three dimensions.

When the above mentioned summed acoustic or mechanical wave is made to propagate to the needle tip, displacement motion control of the needle tip can be achieved similar to that at the coupling point. Pre-determined displacement functions at the displacement signal source permit controlled motion of the distal end of the needle. The displacement functions can be defined by a known function or arbitrary function. Depending on the geometry of the distal end of the conduit, the conduit end can thus be made to perform a certain motion e.g. a scraping/abrading, peeling or cutting motion at the target site. Complex displacement motions along different axes (X, Y and Z-axes, torsional/rotational axes) permit controlling complex displacement motion of the needle end portion and the needle tip.

For example, the driving frequency for the displacement signal source may be selected to achieve flexural resonant mode and crease an up-and-down motion of the conduit tip which may be used in scraping, or abrading the target. Alternatively, the driving frequency may be selected to achieve longitudinal motion to achieve a back-and-forth motion to achieve a cutting effect. As another example, a combination of flexural and longitudinal motion can be achieved at the conduit tip to move according to a certain pattern to perform a certain function such as, for example, a Lissajous patter for performing a peeling-like or scooping-like action.

In at least one example embodiment in accordance with the teachings herein, a combination of acoustic waves from different acoustic sources can be introduced to the conduit through the corresponding couplers to amplify the bevel movement in the Y-direction as shown in example A16 in FIG. 4F. Another combination of parameter values can be applied to achieve amplified movement of the bevel in the X-direction (see example A10 in FIG. 4E) or in the Z-direction (see examples A9 and A15 in FIGS. 4E and 4F, respectively) as explained previously. For example, a frequency can be selected for the different sources to generate a longitudinal resonance in the conduit.

In at least one embodiment in accordance with the teachings herein, another combination of parameter values can be applied to achieve rotational movement (see examples A7 and A14 in FIGS. 4E and 4F, respectively), torsional movement (see example A13 in FIG. 4E) or pitch/yaw/tilting-like movement (see example A17 in FIG. 4F). Other complex trajectories, such as those shown in examples A8, A11 or A12 in FIG. 4E, or arbitrary-shaped trajectories (see example A17 in FIG. 4F) can also be achieved. The determination of the parameter values follows a similar approach as previously described.

Figure 4G:
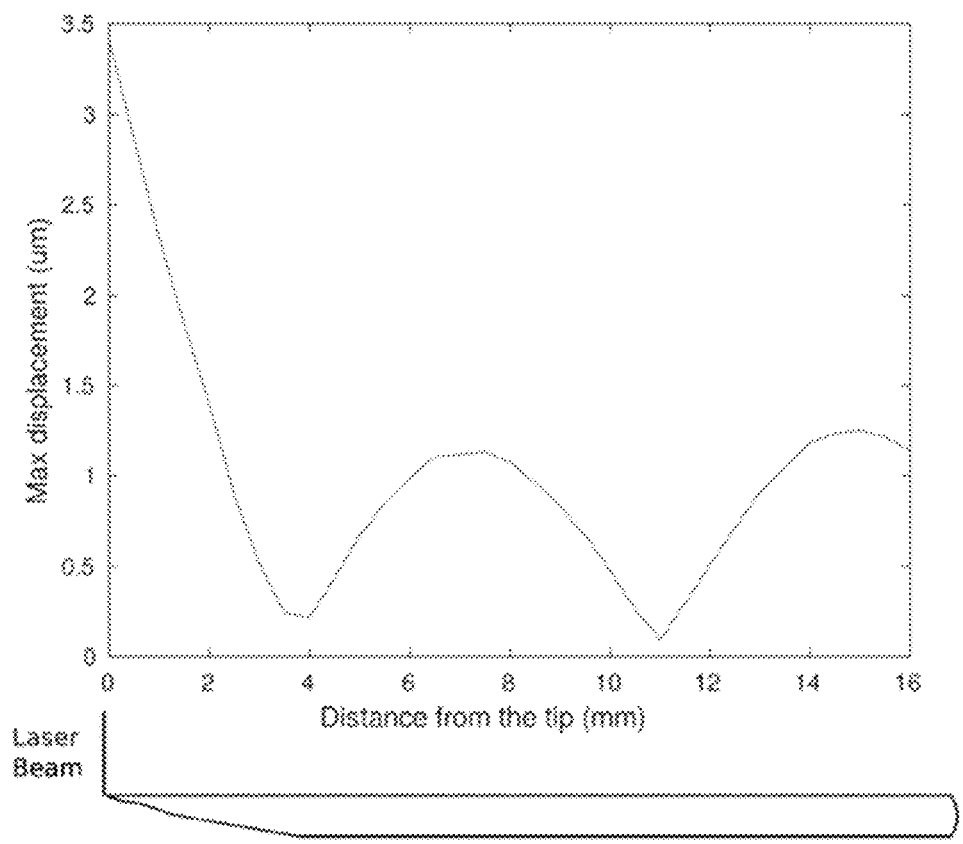
FIG. 4G shows experimental data of the maximum displacement of an end portion and tip of a conduit for a prototype sampling device similar to that presented in FIG. 1A.

As demonstrated in FIG. 4G, using a laser Doppler vibrometer the maximum flexural standing wave was characterized at 0.5 mm steps from the needle tip (along a distance of 0-16 mm) towards the proximal end of the needle. Flexural motion with displacements of several micrometers can be achieved. This result was generated using a similar system as shown in FIG. 1A with a frequency of 30.1 kHz for the displacement signal.

In another aspect, in at least one embodiment in accordance with the teachings herein, the acoustic or mechanical wave mode control can be configured to achieve bevel movement that may be specific to a certain tissue or pathology for efficient sample extraction or to selectively obtain certain objects such as, but not limited to, tissue cores, cyto-cores, tissue constructs, cells, and interstitial fluid, for example. This may be achieved by using acoustic or mechanical wave mode control based to achieve a certain type of movement (i.e. torsional, flexural, and the like) which are more suitable for use with one of the objects listed previously (which may be determined experimentally).

Figure 4H:
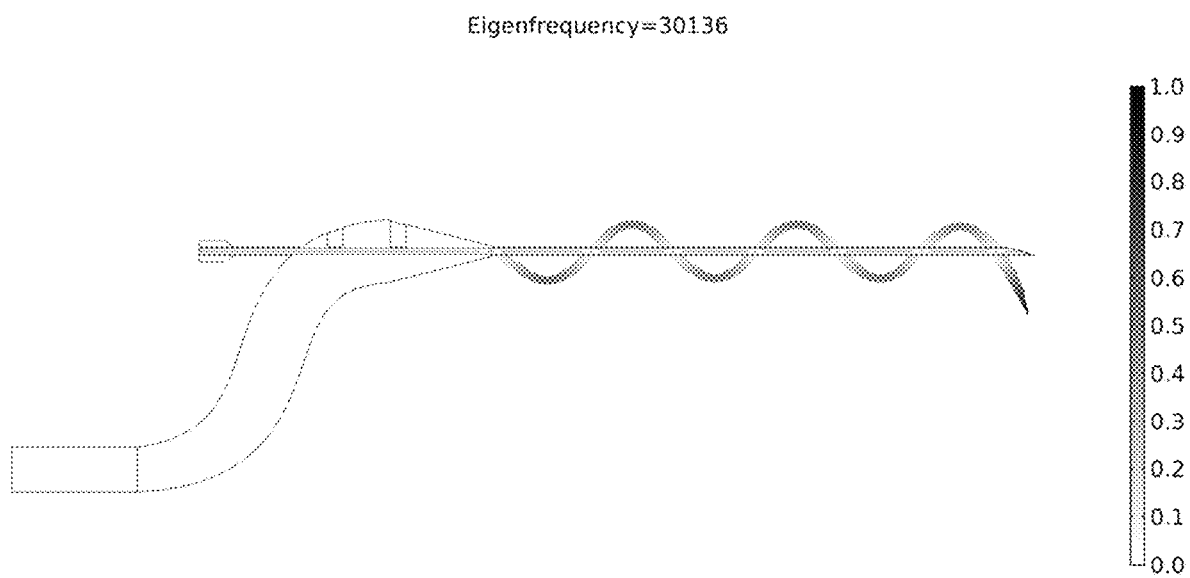
FIG. 4H shows simulation data for an example embodiment of the conduit and waveguide shown in FIG. 1A for achieving a flexural wave mode in the distal end portion of the conduit.
Figure 4I:
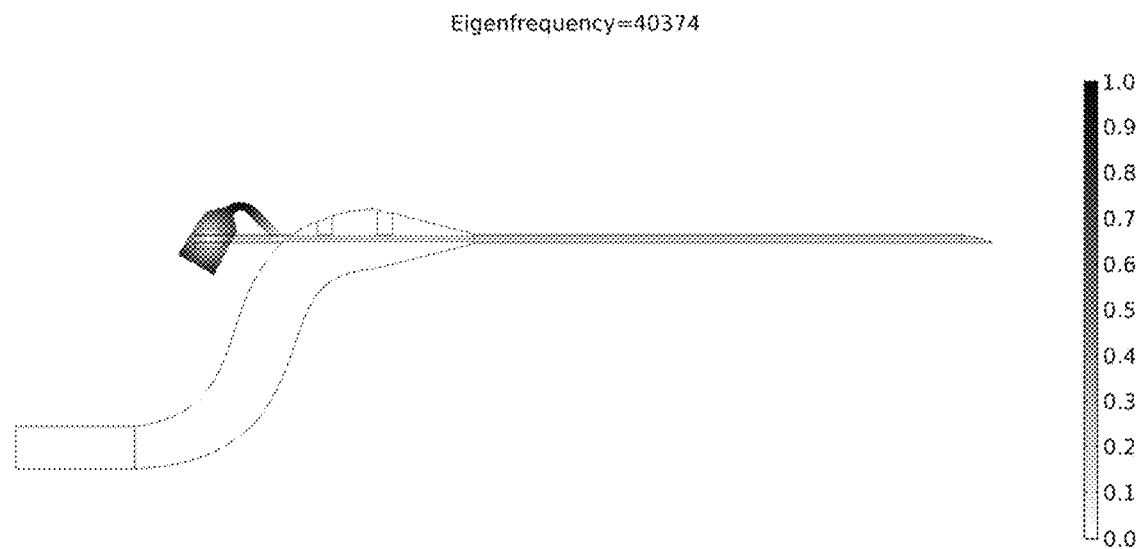
FIG. 4I shows simulation data for an example embodiment of the conduit and waveguide shown in FIG. 1A for achieving a flexural wave mode in a proximal portion of the conduit that is adjacent to the coupler.
Figure 4J:
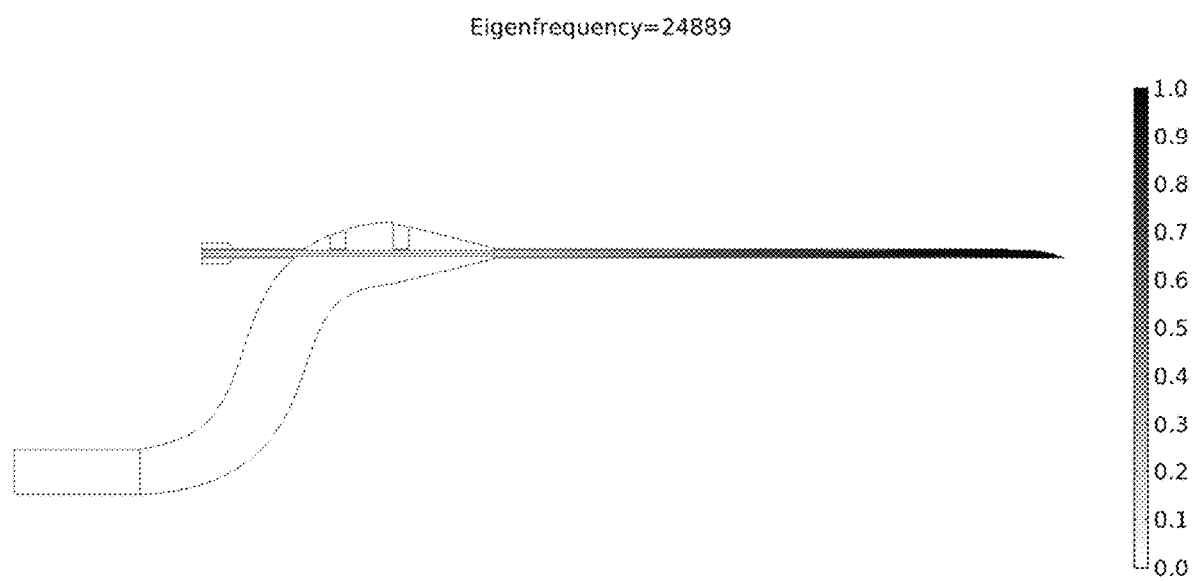
FIG. 4J shows simulation data for an example embodiment of the conduit and waveguide shown in FIG. 1A for achieving a longitudinal mode in the distal end portion of the conduit.

For example, referring now to FIGS. 4H-4J, shown therein is simulation data using a Finite element method (FEM) simulation for an example embodiment of the conduit and waveguide shown in FIG. 1A to achieve: (1) a flexural wave mode in the distal end portion of the conduit (see FIG. 4H), (2) a flexural wave mode in a proximal portion of the conduit that is adjacent to the coupler (see FIG. 4I), and (3) a longitudinal mode in the distal end portion of the conduit (see FIG. 4J). These modes are different eigenmodes that can implemented by using certain operational parameters for the displacement signal source based on certain physical characteristics (i.e. material, coupler geometry) for the device.

The geometric parameters for the simulation included using: (a) the waveguide of FIG. 1A; (b) a conduit length of 80 mm from the base (e.g. element 45) to the beveled end; (c) a distance of 52 mm between the waveguide tip (adjacent and to the right of the converging structure 44—i.e. end regions 258a and 268a) and the beveled end; (d) an inner and outer diameter of 0.5521 mm and 0.8 mm, respectively for the conduit; and (e) the bevel length was 3.12 mm (z-coordinate difference between the bevel start and the sharp tip of the conduit).

The material parameters for the simulation included specifying all materials to be linear elastic materials. In particular, the conduit and waveguide were specified as being made of "structural steel" with a density of 7850 kg/m$^3$, a Young's modulus of 200 GPa and a Poisson's ratio of 0.33. The connector 45 around the base of the conduit was specified as being made of "PET" material with a density of 1,430 kg/m$^3$, a Young's modulus of 6.9814 GPa and a Poisson's ratio of 0.39. The temperature was assumed to be constant during the simulations.

The boundary conditions for the simulation included specifying that: (a) the displacement of the waveguide base rim was zero, (b) the waveguide and the conduit as well as the conduit and the connector 45 have perfect contact coupling, e.g. are welded together; and (c) the simulation model had left-right symmetry (i.e. along the y-axis) and no symmetry along the conduit direction (i.e. the z-axis) or in the up/down directions (i.e. the x-axis) although in some parts there may be symmetry in the z-axis.

It should be noted that the displacement amplitude shown in these figures is deliberately exaggerated for visualization purposes and that these amplitudes actually range from a few microns to a few tens or hundreds of microns. However, in the figures these amplitudes have been scaled to range from 0 to 1, with 1 indicating the maximum displacement in each figure, and 0 indicating zero displacement. It should also be noted that light shading indicates little or no displacement while dark shading indicates a large displacement.

Each of FIGS. 4H-4J are representative of different resonant modes. By selection of different ultrasound parameter(s), such as frequency in these three examples, one can control (1) what wave mode is generated and (ii) the wave mode can be generated at will at selected locations of the conduit. This may have various benefits as shown in the following examples.

Example A

The wave mode can be chosen such that the distal part of the conduit (i.e. the end portion) moves while the proximal part of the conduit is still. This may be useful in sucking up a sample into the proximal end of the conduit (or into reservoir 20) such that it is not actuated while still actuating the distal end portion to perform actuation. This may help reduce cell lysis in the proximal end and maintain better tissue architecture for the obtained samples in the case of tissue samples (this may also improve patient safety).

Example B

The wave mode can be selected to achieve actuation in the proximal part of the conduit while the distal part of the conduit (i.e. the end portion) remains still. This allows the distal part of the conduit to be inside an object or a patient, while the proximal part of the conduit is actuated. This may allow for enhanced sample fixation within the proximal part of the conduit (or within the reservoir) if a fixative is used, while not subjecting the object or the patient to any unnecessary sound exposure (this improves patient safety).

Example C

The ultrasonic parameters can be adjusted to excite an intended mode (e.g. flexural or longitudinal) within the distal part of the conduit. This may have various benefits as described herein.

Example D

The wave mode can be selected such that the proximal and distal end portions of the conduit can be actuated simultaneously with the same or different wave modes. For example, the distal end portion of the conduit can be excited with a longitudinal wave mode while the proximal end portion can be excited with a flexural wave mode which may be used to achieve a cutting action to obtain soft tissue cores near the distal portion of the conduit while the displacement action in the proximal portion of the conduit may enhance the action of a fixative (if used).

Example E

The sampled material is in the reservoir and proximal conduit action can be used to functionalize the sampled material such as by selecting the wave mode to: (1) reduce the time needed for fixative to enter sampled cells (which may lead to better cell/RNA preservation) or (2) generate microbubbles within the fluid inside the reservoir before injecting the fluid into the object so that the microbubbles may be used as an US contrast agent during US imaging or as ultrasound microactuators to enhance biopsy action.

Example F

The wave mode in the proximal part of the conduit can be used to activate the content of the reservoir which can then be delivered as cells, or particles in a motion/fluid/cell/tissue translation that can be achieved using radiation forces, acoustic streaming (e.g. Eckart, Schlichting or Rayleigh streaming), primary/secondary Bjærknes forces and cavitation.

Example G

A superposition of longitudinal, flexural and radial wave modes can be used to facilitate movement of entities along the conduit similar to peristalsis or palpation. The superposition may be used to generate Standing waves.

Example H

A smooth transition between different wave modes may be coordinated by using pressure sensors and by the positioning of the head or plunger 48 of the pressure actuator 46. For example, the pressure sensors (not shown) may be used to detect resonance and the plunger 48 may be used to modify resonance within the reservoir 20 depending on the detected resonance. It is expected that the needle resonance may be controlled electrically by using a pressure sensor to identify when resonance occurs in the reservoir.

In another aspect, in at least one embodiment in accordance with the teachings herein, the acoustic or mechanical wave mode control can be configured to achieve controlled cavitation at a desired location of the conduit. Inertial cavitation is a threshold phenomenon that is strongly dependent on e.g. negative pressure amplitude, presence of nucleation sites, applied frequency and history of the acoustic field. Knowledge of the acoustic field near the conduit and temporal control over sonication parameters permits one to control the cavitation sites. By introducing nucleation sites, i.e. micro-bubbles, through the conduit to the target site, cavitation can be efficiently limited to the proximity of the distal end of the conduit. Nucleation sites for can be achieved by generating grooves, holes, dents, or patterns on the inner or outer surfaces of the conduit (some examples for this are shown in FIGS. 1B, 1C, 1F and 1K) that can trap gas. This is discussed further with respect to the experimental results shown in FIG. 11.

In another aspect, in at least one example embodiment in accordance with the teachings herein, a standing wave can be generated inside the conduit to translate matter obtained from the target site to the reservoir of the sampling device. Alternatively, the standing wave inside the conduit can be used to arrange the matter obtained from the target site according to a certain characteristic, such as in order of increasing size, for example, as follows: cell nuclei, small cells, big cells, small tissue constructs, big tissue constructs. The forces acting on the matter (objects) and the velocity of objects can be controlled, e.g. by modifying the amplitude and frequency of the electrical driving signals that are provided to the displacement signal sources to create the mechanical or acoustic waves. This is because standing waves can generate a force gradient that can translate particles faster or slower depending on the particle size, shape and acoustic impedance in respect to the surrounding medium (e.g. interstitial fluid, fixative or physiological saline). Therefore, the particles can be ordered within the conduit according to the particle properties.

Figure 5:
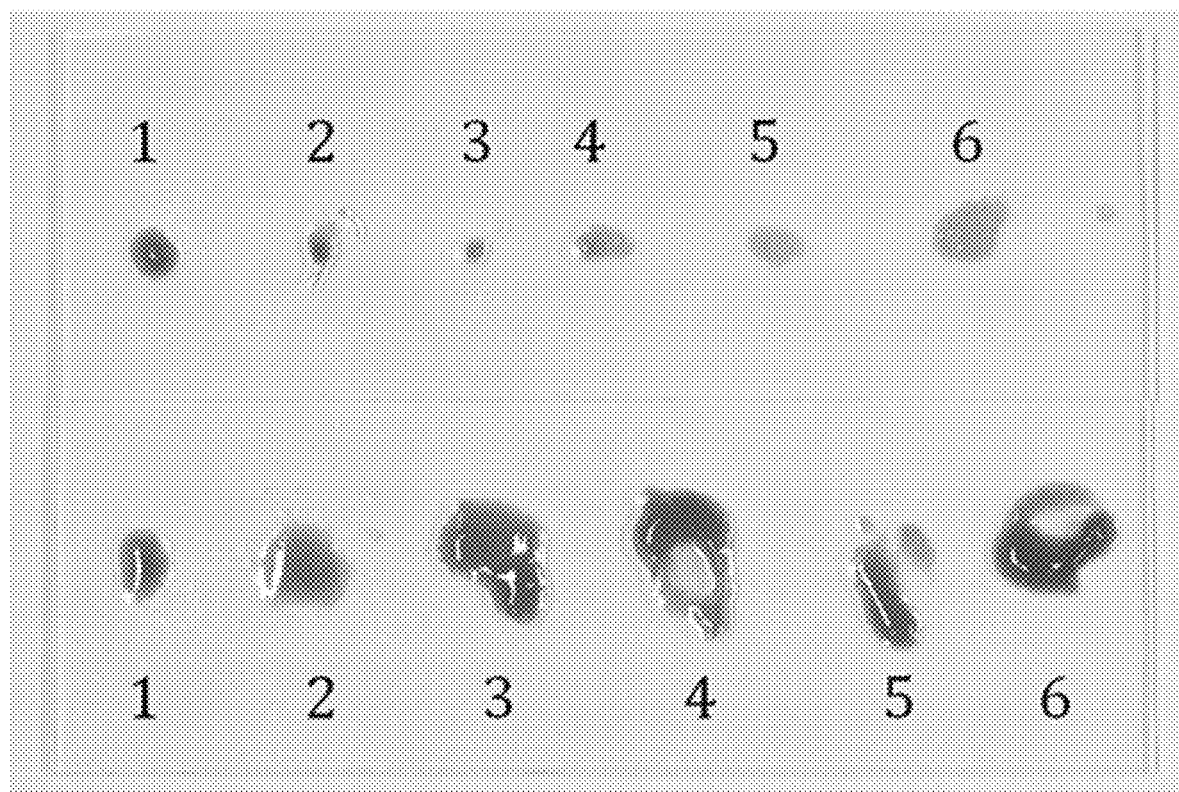
FIG. 5 shows preliminary results of sampling using a sampling device prototype similar to that in FIG. 1A.

Referring now to FIG. 5, shown therein are tissue samples extracted from bovine liver using conventional FNA (upper row) and using USeFNA in accordance with the teachings herein (lower row). To acquire the samples described in FIG. 5, sinusoidal ultrasound bursts (300 cycles/burst, burst repetition frequency 30 Hz) were produced at 31.21 kHz center frequency to achieve the mechanical displacement signal. The detailed experimental protocol that was followed in shown in Table. 1.

TABLE 1

Experimental Protocol

| Step # | USeFNA | CONVENTIONAL FNA |
|---|---|---|
| 1 | Decompress syringe to the 5 ml mark and hold the plunger | Decompress syringe to the 5 ml mark and hold the plunger |
| 2 | Insert needle into the sample | Insert needle into the sample |
| 3 | Decompress syringe to the 20 ml mark and hold the plunger | Decompress syringe to the 20 ml mark and hold the plunger |
| 4 | Turn ultrasound on | N/A |
| 5 | Wait for 10 seconds | Wait for 10 seconds |
| 6 | Turn ultrasound off | N/A |
| 7 | Release the plunger to relieve the decompression | Release the plunger to relieve the decompression |
| 8 | Withdraw needle from the sample | Withdraw needle from the sample |
| 9 | Compress the syringe to eject collected matter from the needle onto a glass slide | Compress the syringe to eject collected matter from the needle onto a glass slide |

Accordingly, in at least one embodiment, there is provided a method of using a device having a pressure controller with a reservoir, a conduit and a displacement signal source for generating a mechanical displacement signal to obtain an entity from a target site when the conduit is placed at the target site, wherein before generating the mechanical displacement signal, the method comprises actuating the pressure controller to a first volume setting for a reservoir of the pressure controller; inserting the conduit into the target site; and actuating the pressure controller to a second volume setting for the reservoir of the pressure controller, the second volume being larger than the first volume. In the example testing, the second volume setting was 4 times the value of the first volume setting. However, in other cases, the second volume may be much smaller or much larger than the first volume. In addition, in some cases the first volume can be much smaller or greater than the 5 ml setting used in the example testing.

The mechanical displacement signal is generated for a first time period after which the pressure controller is actuated to relieve decompression thereby obtaining the entity from the target site, and the conduit is then withdrawn from the target site. This may involve adjusting the volume setting for the reservoir back to the original or to another setting that is lower than the setting associated with the second volume.

After withdrawing the conduit from the target site, the pressure controller is actuated to eject the obtained entity onto a glass slide or into a container.

Alternatively, while generating the mechanical displacement signal, the method may comprise obtaining the entity from the target site or delivering a second entity from a reservoir or from the conduit to the target site.

In another alternative, while generating the mechanical displacement signal, the method may comprise inserting the conduit into the target site or removing the conduit from the target site. This may be advantageous as it may result in lowered penetration resistance and lower pain for the patient during biopsy or drug delivery.

In another alternative, while generating the mechanical displacement signal, the method may comprise moving the device using an operator's hand or robotics in order to achieve translation, tilting or rotation of the conduit or conduit tip within or outside of the target site.

Accordingly, USeFNA, according to the teachings herein, may be combined with translation, tilting, and/or rotation of the device during entity extraction or entity delivery. Combination of USeFNA and this movement of the device may generate a greater yield and better repeatability, as demonstrated in FIGS. 6A and 6B.

The results shown in FIG. 5 demonstrate that on average a greater volume of tissue sample can be extracted with USeFNA (n=6) as compared to FNA (n=6) (no ultrasound) when the instruments are not intentionally moved by the operator's hand.

Figure 6A:
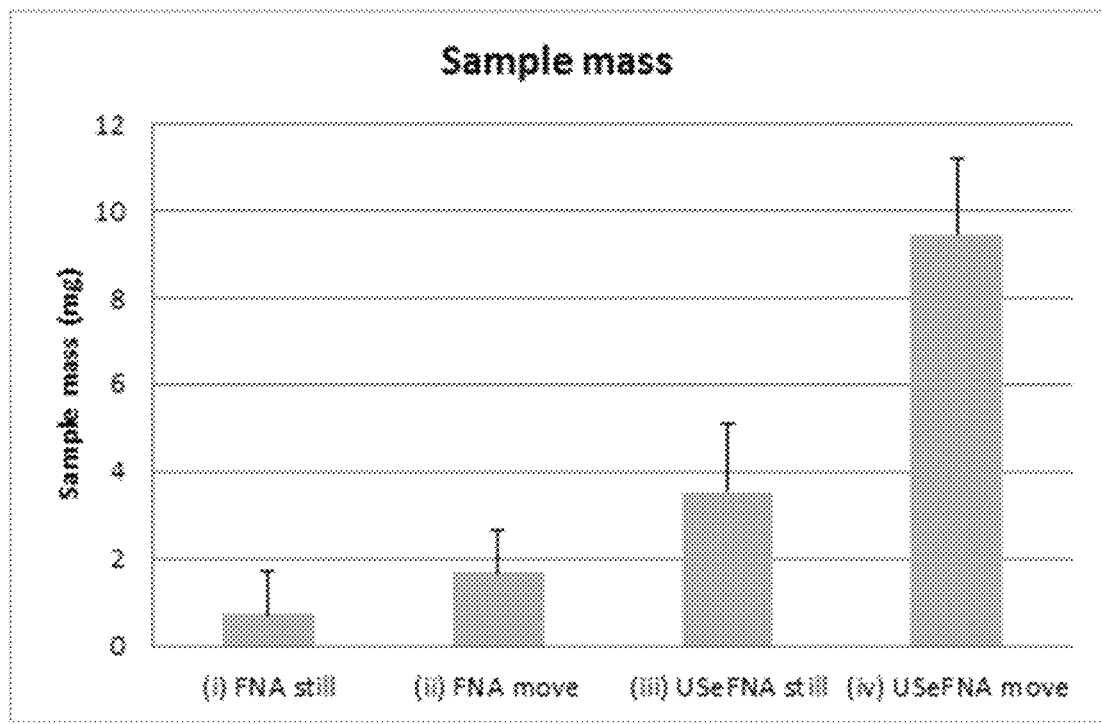
FIGS. 6A and 6B show extracted sample volumes obtained with FNA and ultrasound-enhanced FNA, as well as the repeatability of each approach, respectively.
Figure 6B:
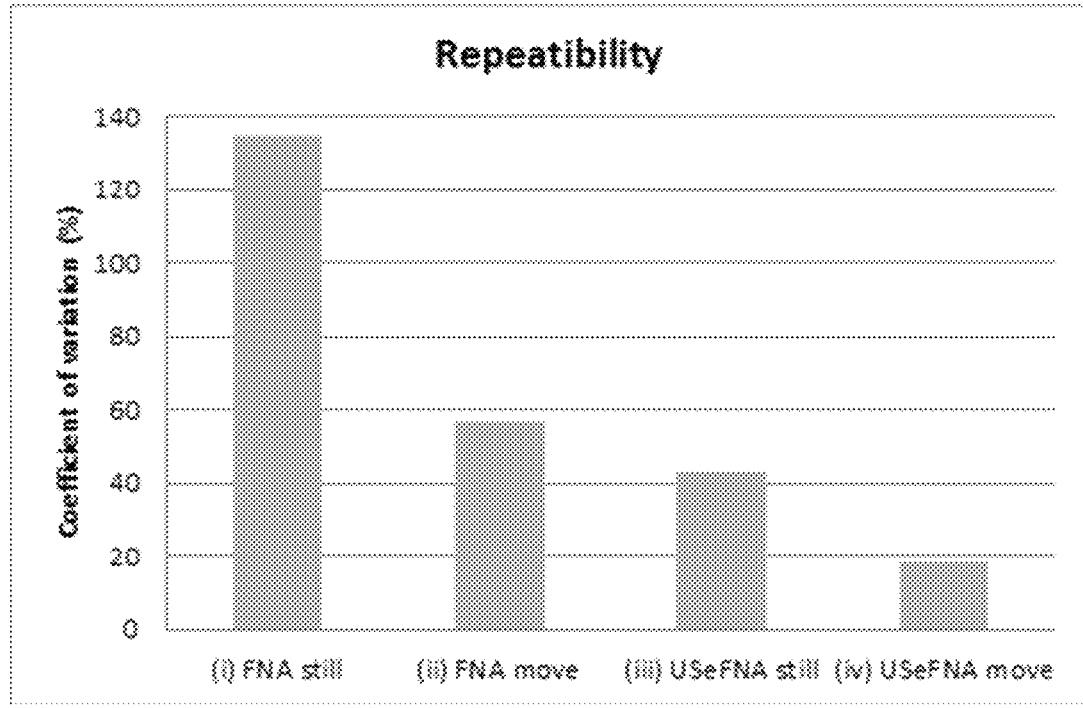

FIG. 6A presents the weight of bovine liver samples obtained with (i) conventional FNA with the instrument being still (n=10), (ii) conventional FNA with the instrument being moved (e.g. the syringe and needle were rotated relative to the center axis of the needle while varying the angle of entry) (n=9), (iii) USeFNA in accordance with the teachings herein with the instrument being held still (n=10) and (iv) USeFNA in accordance with the teachings herein with the instrument being moved (e.g. the syringe and the needle were rotated relative to the center axis of the needle while varying the angle of entry) (n=10). The ultrasound settings and sample acquisition process were the same as those used to acquire the data shown in FIG. 5 with the following exception: in experiments (ii) and (iv) the instrument was moved during step 5 (See Table 1). The obtained sample volumes with the used settings were on average 2.1× and 5.6× greater in USeFNA without or with instrument movement, respectively, as compared to conventional FNA with movement (equivalent to standard FNA). FIG. 6B presents the coefficient of variation (%) for sample mass obtained with the different approaches described above as (i)-(iv). The results demonstrate that the coefficient of variation is 13 percentage points and 38 percentage points greater with conventional FNA (with movement, CV %=57%, n=9) as compared to USeFNA without (CV %=43%, n=10) or with (CV %=18%, n=10) instrument movement, respectively. The results suggest that USeFNA enhances intra-user repeatability, while significantly increasing the volume of sample extracted from tissue.

Figure 7:
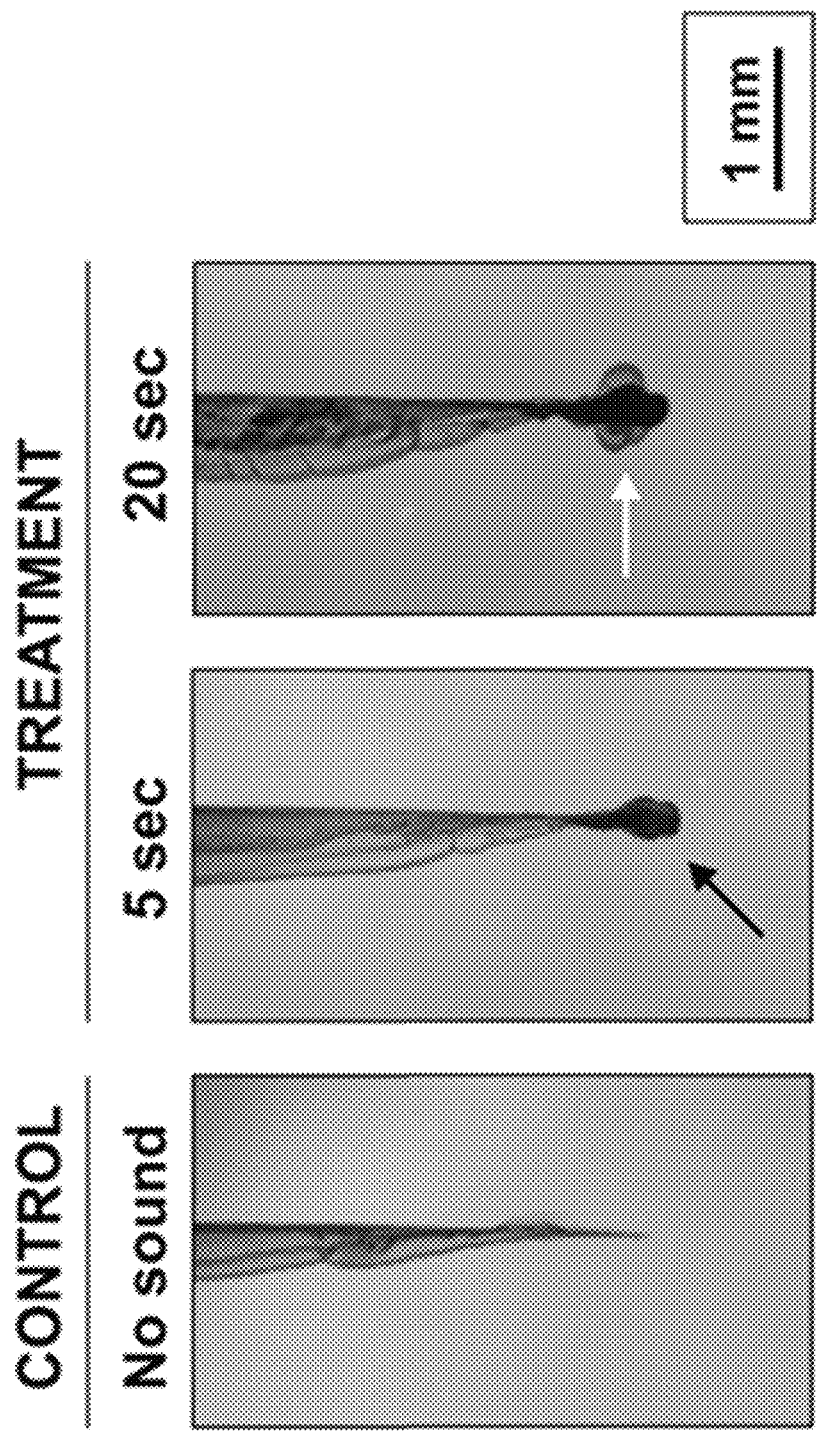
FIG. 7 demonstrates the capability of ultrasound-enhanced FNA to deliver drugs.

Referring now to FIG. 7, shown therein are images that demonstrate the capability of USeFNA, in accordance with the teachings herein, to deliver agents into a tissue phantom. Optically transparent gelatin (~5% w/v) was used as the phantom and 17% w/v Winsor & Newton black ink was used as a drug surrogate. The control treatment consisted of penetrating the hypodermic needle into gelatin, without the application of ultrasound. The investigated treatment consisted of penetrating the hypodermic needle into the gelatin after which ultrasound was applied for 5 or 20 seconds (i.e. sinusoidal ultrasound bursts at 30 kHz, burst repetition frequency 55 Hz). Following ultrasound exposure, delivery of black ink (vertically and horizontally from the location of the hypodermic needle tip) into gelatin was observed after 5 sec of ultrasound exposure (black arrow) as compared to a control with no ultrasound. The delivery was pronounced (enhanced horizontal delivery, white arrow) when sonication time increased to 20 sec.

Figure 8A:
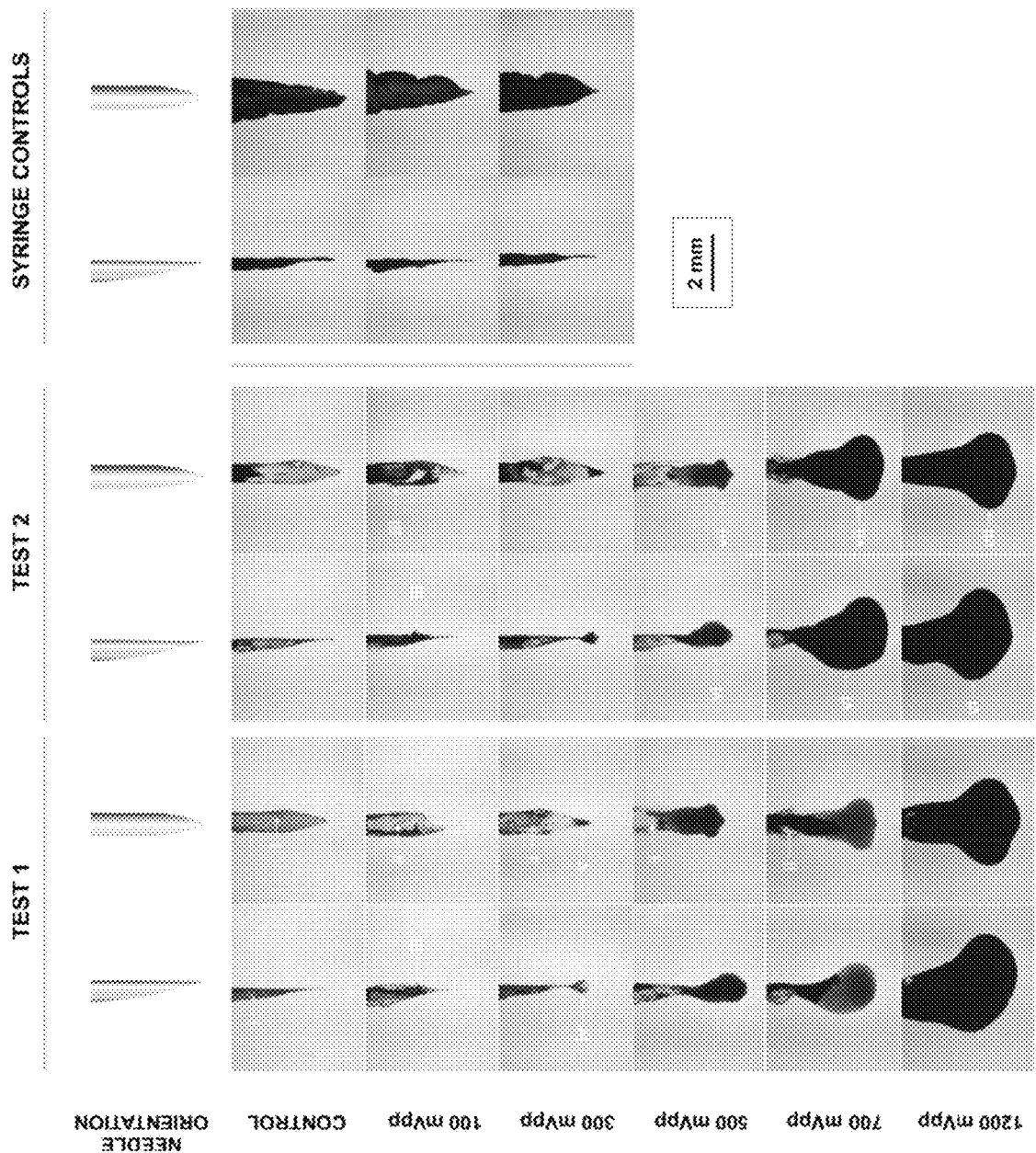
FIG. 8A shows experimental test results and syringe controls illustrating the dependence of ultrasonic power and penetration depth on the delivery of agents inside gelatin.

Referring now to FIG. 8A, shown therein are experimental test results illustrating the relationship between ultrasonic power and penetration on the delivery of agents inside gelatin. The experiment involved using a custom-made amplifier, an HP33120A function generator, and the sampling device prototype of FIG. 1A. The samples were 4.8% w/v gelatin (i.e. 10 g of gelatin powder to 200 mL of ion-exchanged water). The samples were stirred and heated over 60° C. A volume of 3.5 mL of gelatin solution was then poured into 4.5 mL cuvettes with four clear faces. One cuvette corresponds to one sample. Samples were then cooled in a fridge for more than 1 hour before the experiments were performed. A Contrast Agent (CA) was also used in the experiments. The CA comprised 15% v/v Winsor & Newton black ink (15 mL) mixed with ion-exchanged water (85 mL).

A series of experiments involved vertically connecting the sampling device prototype to a translation stage with the needle tip facing down. The syringe and needle were then filled with the CA. A few droplets of the CA were ejected onto the gelatin surface. The needle was positioned at the center of the 10×10 mm² cuvette. The needle was then placed into the gelatin. The depth of the needle tip from the gelatin surface varied between about 6-10 mm. The needle was then moved 3 times up and down ("pumping") to deliver the CA to the tip of the needle. No CA was ejected from the syringe reservoir to the needle tip while the needle was inserted in the gelatin in order to avoid damage to the gelatin. Then with the needle inserted into the gelatin, sonication was applied for 5 seconds at different function generator voltages. Treatment sonication used a function generator voltage ranging from 100-1200 mV and the control did not use sonication. Test parameters are shown in TABLES 2 and 3. The test series were repeated to show repeatability (n represents the number of tests). Peak resonance was at about 31.2 kHz, but the system was deliberately driven adjacent to resonance, i.e. at 30.9 kHz to avoid the system flipping into anti-resonance.

TABLE 2

List of samples & treatments

| Sample | n | Sonicated? | Function generator peak-to-peak voltage (mV) |
|---|---|---|---|
| Control | 2 | No | N/A |
| T_100 | 2 | Yes | 100 |
| T_300 | 2 | Yes | 300 |
| T_500 | 2 | Yes | 500 |
| T_700 | 2 | Yes | 700 |
| T_1200 | 2 | Yes | 1200 |

TABLE 3

Sonication parameters

| Parameter | Value |
|---|---|
| Frequency | 30.9 kHz |
| PRF | 55 Hz |
| Cycles per burst | 300 |
| Duty Cycle | 53% |
| Gain setting at custom-made amplifier | 10 |

The syringe control experiments were done by penetrating the needle tip of the prototype sampling device into the gelatin to a depth of about 20 mm and pressing the piston of a 1 mL syringe to deliver approximately 30 μL of CA into the gelatin. The test was conducted for three samples CS1, CS2, and CS3. No "pumping" or ultrasound was applied.

The locations of the delivery of the CA to the gelatin samples were imaged from the front and side of the gelatin samples using a Zeiss Stemi 2000-C microscope and a Thorlabs USB camera that was operated in reflection mode with an angular magnification of 0.8×.

The delivered cargo dimensions (e.g. length, width, and height) were measured from the microscope images. An ellipsoid assumption was used to calculate volume (e.g. as a first ballpark estimate). This is because the height measure of the delivered cargo is highly subjective, and, thus, the height and volume measures are biased and, thus, serve only as the first estimate of the volume of the delivered cargo.

The results shown in FIG. 8A for the row labelled control are microscope images of the delivered cargo under no sonication and with different function generator voltages. The results in FIG. 8A illustrate that the contrast of the CA was quite uniform in the syringe controls (i), but was found to be heterogeneous at a function generator voltage setting of about 100 mV or higher for the points labeled (ii) (see the second column of the Test 1 series results in FIG. 8A). At a function generator voltage setting of 100 mV, "spikes" of CA were observed at the points labeled (iii) in the first, second and third columns of FIG. 8A, which might be due to cavitation. Rather, delivery of the CA was observed with function generator voltage settings of 300 mV and higher (see the points labeled iv-vii). The size, shape and volume of the delivered cargo were repeatable by visually comparing the Test 1 results to the Test 2 results. The tests results generally show that the delivered cargo was heart-shaped at 300 mVpp, and that the shape changed to droplet-like (side view) or arrow-like (front-view) at 500 mVpp and higher. In syringe controls, the delivery of 30 μL of CA was seen within the channel of the needle, but enhanced delivery downwards from the approximate location of the needle tip was not observed (see the syringe control images in FIG. 8A). Macroscopically, the ink was "pushed" up through the channel of the needle to the top surface of the gelatin sample.

Accordingly, volumetric precision/control with the syringe approach was inferior to USeFNA, which was performed in accordance with the teachings herein.

Figure 8B:
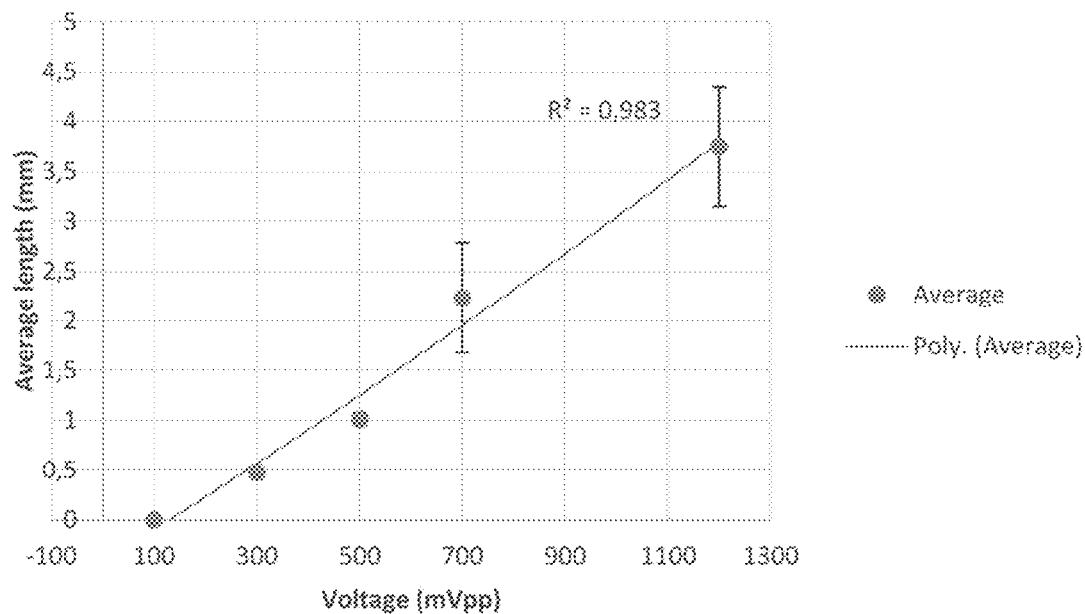
FIG. 8B shows the average length of the delivered cargo as a function of different function generator voltages.
Figure 8C:
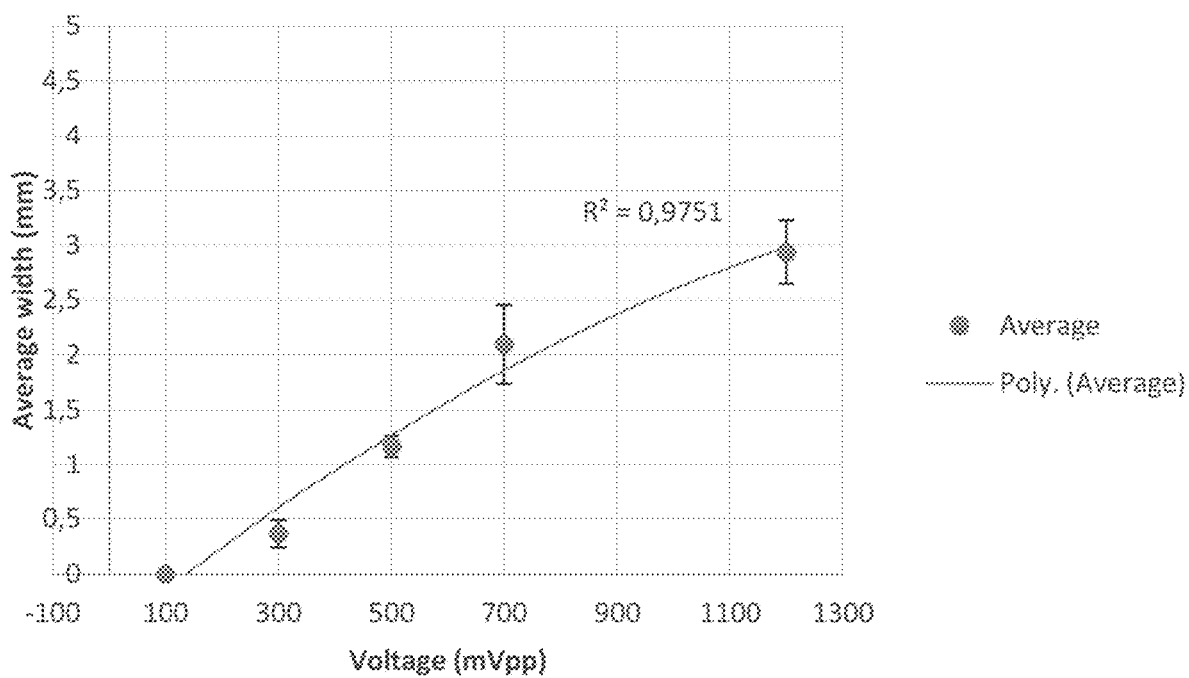
FIG. 8C shows the average width of the delivered cargo as a function of different function generator voltages.

The length, width, height and volume (ellipsoid assumption) of the delivered entities are presented in FIGS. 8B-8C. In particular, FIG. 8B shows the average length of the delivered cargo as a function of different function generator voltages (e.g. different power levels) while FIG. 8C shows the average width of the delivered cargo as a function of different function generator voltages (e.g. different power levels). The results suggest that increasing the driving voltage (i.e. increasing power) increases the dimensions and volume of the delivered cargo. At the highest voltage applied during the experiments (about 1200 mV), disintegration of the gelatin sample was observed.

Accordingly, these test results show that: 1) the dimensions and volume of the delivered cargo increase with increasing acoustic power with the assumption that increasing electric power increases acoustic power; 2) the delivered cargo was a volume on the order of tens of microliters; 3) the USeFNA technique in accordance with the teachings herein delivered the CA into a small and confined volume of the gelatin samples as compared with the conventional needle & syringe approach; and the volume covered by the delivered CA may represent where actuation of the tissue occurs during extraction of cells within the tissue.

Figure 9A:
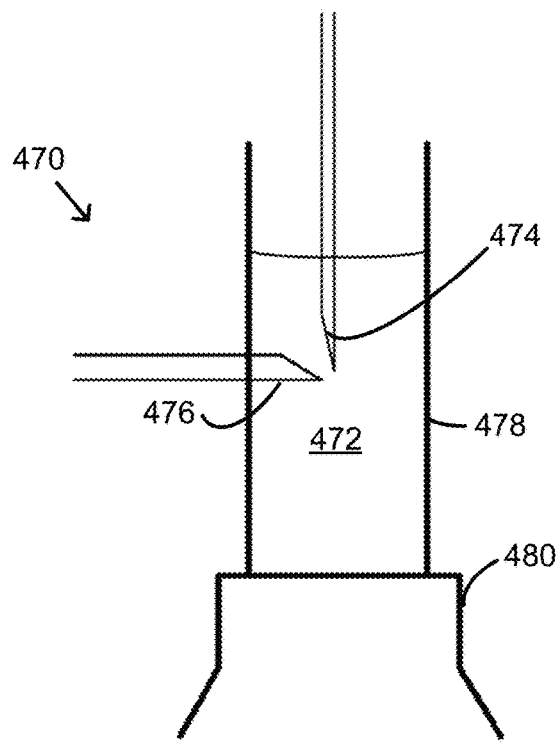
FIG. 9A shows the experimental setup for testing temperature rise in gelatin during sonication with different power levels.

Referring now to FIG. 9A, shown therein is an experimental setup 470 for testing temperature rise in gelatin during sonication with different power levels for the sampling device prototype. The needle tip 474 of the sampling device prototype was positioned about 2 mm from a thermometer tip 476 (Gulton Tastotherm D700) that was positioned horizontally. The thermometer needle tip 476 and the needle tip 474 of the sampling device prototype were then molded into the gelatin 472 which was in a container 478 mounted on a base 480. The USeFNA equipment was as described for the testing shown in FIGS. 8A-8C.

The material sample comprised 4.8% w/v gelatin (i.e. 0.5 g of gelatin powder and 10 mL of ion-exchanged water). The sample was stirred and heated over 60° C. About 3.5 mL of gelatin solution was poured into a 4.5 mL cuvette along with a thermometer and USeFNA needle (see FIG. 9A). The sample was then cooled in room temperature to about 23° C. before the experiments were performed. The gelatin sample acted as a tissue phantom in these experiments.

Two additional experimental series, were established in which a 5 second sonication and a 20 second sonication were used in obtaining the results. In both series (5 sec and 20 sec), the sampling device prototype had a G21 needle that was vertically connected to a translation stage needle tip that was facing downwards and the needle tip depth in the gelatin sample was ~6 mm (see FIG. 9A). The thermometer tip was introduced horizontally into the cuvette through a hole drilled in the cuvette as shown in FIG. 9A. The thermometer tip and the needle tip were molded into the gelatin sample to have a good thermal coupling between the thermometer tip, the needle tip and the gelatin sample. The USeFNA sonication was applied for 5 seconds and 20 seconds and the thermometer reading was recorded before and after sonication. The sample was allowed to cool down between successive sonications. The applied sonication settings were the same as what is shown in Table 3 and the function generator provided voltages having amplitudes of 100, 300, 500, 700 and 1200 mVpp. After sonicating the sample with the 5 different function generator voltages and the two different sonication times (5 sec and 20 sec), the tests were repeated.

Figure 9B:
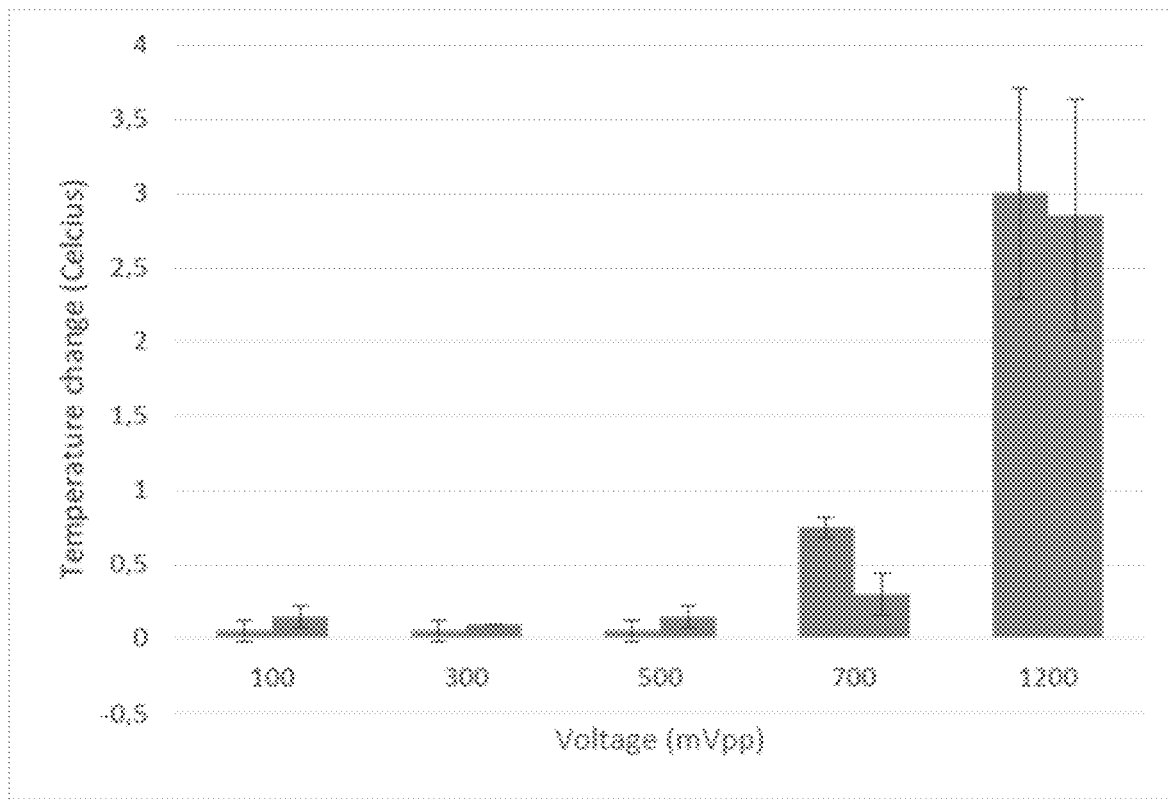
FIG. 9B shows a bar chart illustrating temperature change for different applied voltages for the two different experimental series (i.e. Series 1 and Series 2).

Referring now to FIG. 9B, shown therein is a bar chart illustrating temperature change for different applied voltages for the two different experimental series (5 sec and 20 sec), which represents the temperature rise close to the needle tip of the sampling device as a function of function generator voltage. The first bar in each pair of bars is for 5 second sonication while the second bar in each pair of bars is for 20 second sonication and for both bars, the error bar shows the standard deviation (SD) of the test results. On average, the temperature rise was <1° C. for function generator voltage settings that were 700 mVpp or lower. The temperature rise was on average 3° C. (a maximum reading was 3.5° C.) with a voltage setting of 1200 mVpp for the function generator.

Accordingly, with a 5 sec sonication time, the temperature rise was (i) negligible (on average it was about 0.1-0.2° C.) with 500 mVpp or lower function generator voltage, (ii) small (<1° C.) with 700 mVpp setting and (iii) relatively small (average 3° C., maximum reading: 3.5° C.), but clinically potentially acceptable at a 1200 mV setting (see FIG. 9B). When increasing the sonication time to 20 sec, a slight temperature rise was observed at function generator voltage settings of 500 mVpp or lower, but a smaller temperature rise was seen at 700 mVpp and 1200 mVpp (see FIG. 9B). A potential explanation for this difference is that the longer sonication time of 20 seconds combined with visible acoustic streaming at function generator voltages of 700 mVpp and 1200 mVpp (i.e. which were visible to the naked eye), resulted in heat convection near the needle tip of the sampling device prototype that allowed the heat to diffuse outwards in close proximity to the thermometer compared to lower sonication times (e.g. for 5 sec). The mean temperature (±SD) before the sonication was 23.0±0.3° C. (n=20). Therefore, with the function generator voltages at 700 mVpp or less, the temperature rise was less than 1° C. for 5 and 20 second sonications which demonstrates that the technique of USeFNA in accordance with the teachings herein may be thermally safe when applied to tissue.

Referring now to FIGS. 10A-10B, shown therein is an illustration of the experimental setup used to test for cavitation effects in water during sonication at different power levels. The experimental equipment was similar to that used in the previous tests described herein with the addition of a Zeiss Stemi 2000-C microscope, a Thorlabs USB camera, and a white light source. A program used to analyze the results was programmed using MATLAB™ (R2012a). The sample was ion-exchanged water that was maintained at room temperature.

The experiments involved vertically connecting the sampling device prototype having a G21 needle to a translation stage needle tip facing down and immersed in water (see FIG. 10B). A light beam was introduced horizontally to the needle tip in the water. A microscope was used to observe the needle tip at a 90° angle with respect to the light beam (see FIG. 10A) so that no light was directly pointing into the microscope. This experimental setup permitted observing light reflections from the needle and light scattering/reflection from objects floating in the water (e.g. microbubbles). The experiments were done using the experimental parameters shown in Table. 3 with operating voltages of 100, 300, 500, 700 and 1200 mVpp at the function generator. Before each sonication, an image of the sampling device prototype needle with no sound was taken for reference. After the reference image was taken, sound was applied to the sampling device prototype and a video was acquired at 20 frames/sec for 10 seconds using the microscope and the USB camera.

The analysis involved performing certain image processing methods on the images that were obtained during experimentation and analyzing the processed images for any cavitation effects. An image processing method was used to obtain a pixel-wise temporal maximum image (the maximum value in each pixel was calculated as the maximum value in that pixel during a specified time window) using MATLAB™.

The image processing method used to obtain the pixel-wise temporal maximum image involved averaging the first 10 first frames of video corresponding to 0.5 seconds of sonication to obtain a time-averaged image in order to visualize the transient light scattering/reflection. Following this, the background reference image (i.e. an image of the needle taken with no sound, before sonication) was subtracted from the time-averaged image to make the image background uniform. Subsequently, a silhouette of the needle with no sound was then overlaid on the time-averaged image to obtain an intermediate image. Following this, the pixel-wise temporal maximum image was generated. The final image was then obtained after median-filtering (using a 7×7 pixel moving window).

The experiments showed that at low intensity, no light scattering around the needle tip was observed (shown in FIG. 10C). However, with increasing power, light scattering was observed near the needle tip at function generator voltages of 500 mVpp (shown in FIG. 10D) and greater (shown in FIG. 10E). The light cloud that was observed was likely a microbubble cloud (as it matched spatially with micro-bubble observations that are visible to the naked eye). The importance of this finding is that micro-bubbles act as micro-actuators that may be potentially useful for loosening cells within tissue during tissue extraction or for enhancing drug delivery (e.g. permeabilization, sonoporation, or convection). It is notable that areas with high bubble density are rather confined with function generator voltage settings of about 500-700 mVpp, but in size exceed the outer diameter of the needle (0.8 mm). This provides spatial control for sampling objects at the target site or for drug delivery to certain objects at the target site.

The experimental results demonstrate that cavitation can be involved in USeFNA at will, when applied in water. Further testing may be done to show whether or not cavitation occurs with USeFNA is applied inside the body. Cavitation may be switched on in the optimization of USeFNA in that cavitation may potentially enable a shorter sample extraction time of a few seconds. Furthermore, cavitation may be used to extract sample entities from tissue volumes with diameters greater than the needle diameter. As demonstrated in FIG. 10E, the bubble cloud is greater in size than the diameter of the needle. These cavitation bubbles can interact with tissue and loosen cells, groups of cells, tissue constructs and tissue cores for biopsy. In e.g. drug delivery application, this bubble may can interact with an object to deliver entities into the object; e.g. the object may be tissue and the delivered entities may be tissue or cells.

Figure 11:
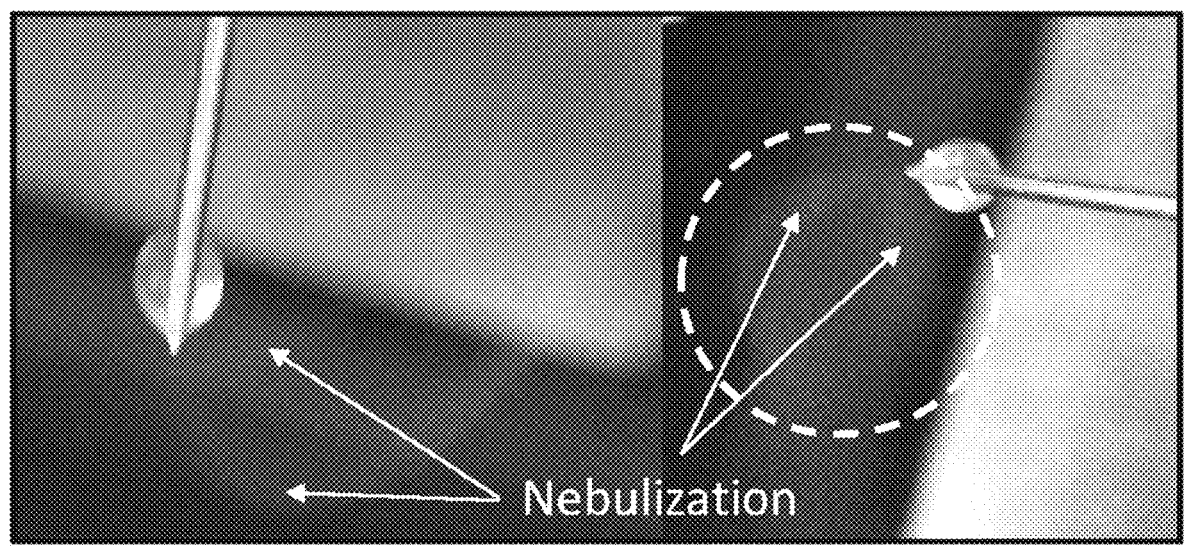
FIG. 11 shows experimental testing that was done in which atomization or nebulization was achieved.

Referring now to FIG. 11, shown therein is experimental testing that was done with water in which atomization and nebulization was achieved with the prototype of FIG. 4A using displacement signal source DS2 and coupler CA2. In particular, FIG. 11 shows atomized water from a droplet of water at the tip of the needle of the prototype. The settings used for the displacement signal source in this testing was a frequency of 726 kHz, a pulse repetition frequency (PRF) of 150 Hz, and 100 cycles per burst. The atomization or nebulization may be used to, respectively, atomize or nebulize certain objects, e.g. ethanol/drugs, and spray the atomized or nebulized objects on a material surface, e.g. tissue surface, or inside cavities such as air cavities, e.g. within the broncus or the skull. Accordingly, the device may be used to achieve atomization or nebulization. Atomization or nebulization can be achieved e.g. by selecting frequency and displacement amplitudes so that capillary waves on the liquid droplet surface or cavitation within the droplet are generated.

Accordingly, in another aspect, in at least one example embodiment described herein, micro-bubbles or nano-bubbles may be introduced into the target site or near the target site through the conduit end portion 25 or are created in situ near the tip 26 of the conduit 24. Following this, mechanical or acoustic waves may be introduced to the tip 26 of the conduit 24 to achieve enhanced actuation by using at least one of cavitation, shock waves, streaming and radiation forces, for example. The enhanced actuation can be used to enhance extraction of cells and tissue constructs for cytology as described earlier. Alternatively, the enhanced actuation may be used or to achieve enhanced delivery of objects into cells or tissue and possibly for enhanced imaging contrast during US imaging, for example.

Figure 12:
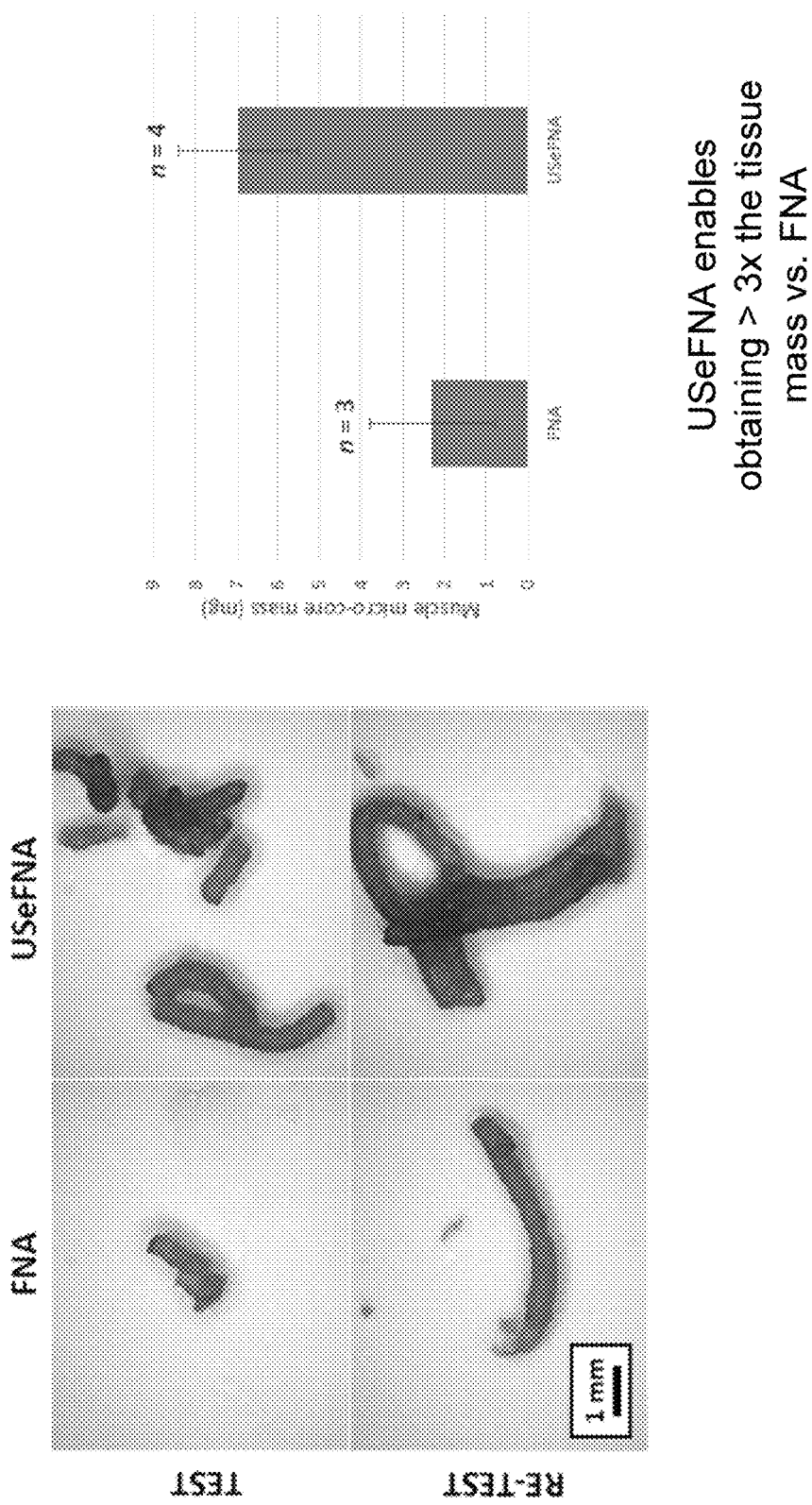
FIG. 12 shows bovine muscle micro-core samples obtained using conventional FNA and ultrasound based FNA in accordance with the teachings herein.

Referring now to FIG. 12, shown therein are bovine muscle micro-core samples obtained using conventional FNA and USeFNA in accordance with the teachings herein. Several repeats (n=3, FNA; n=4; 30±2 kHz, ultrasound based FNA with a total acoustic power of 0.28 W, a 10 second sample acquisition time, a pulse repetition frequency of 55 Hz, and 300 cycles per burst) revealed that the mass of the tissue samples was remarkably greater (>3×) with USeFNA compared to FNA. Thus, USeFNA described in accordance with the teachings herein may be used to obtain core biopsies.

Figure 13:
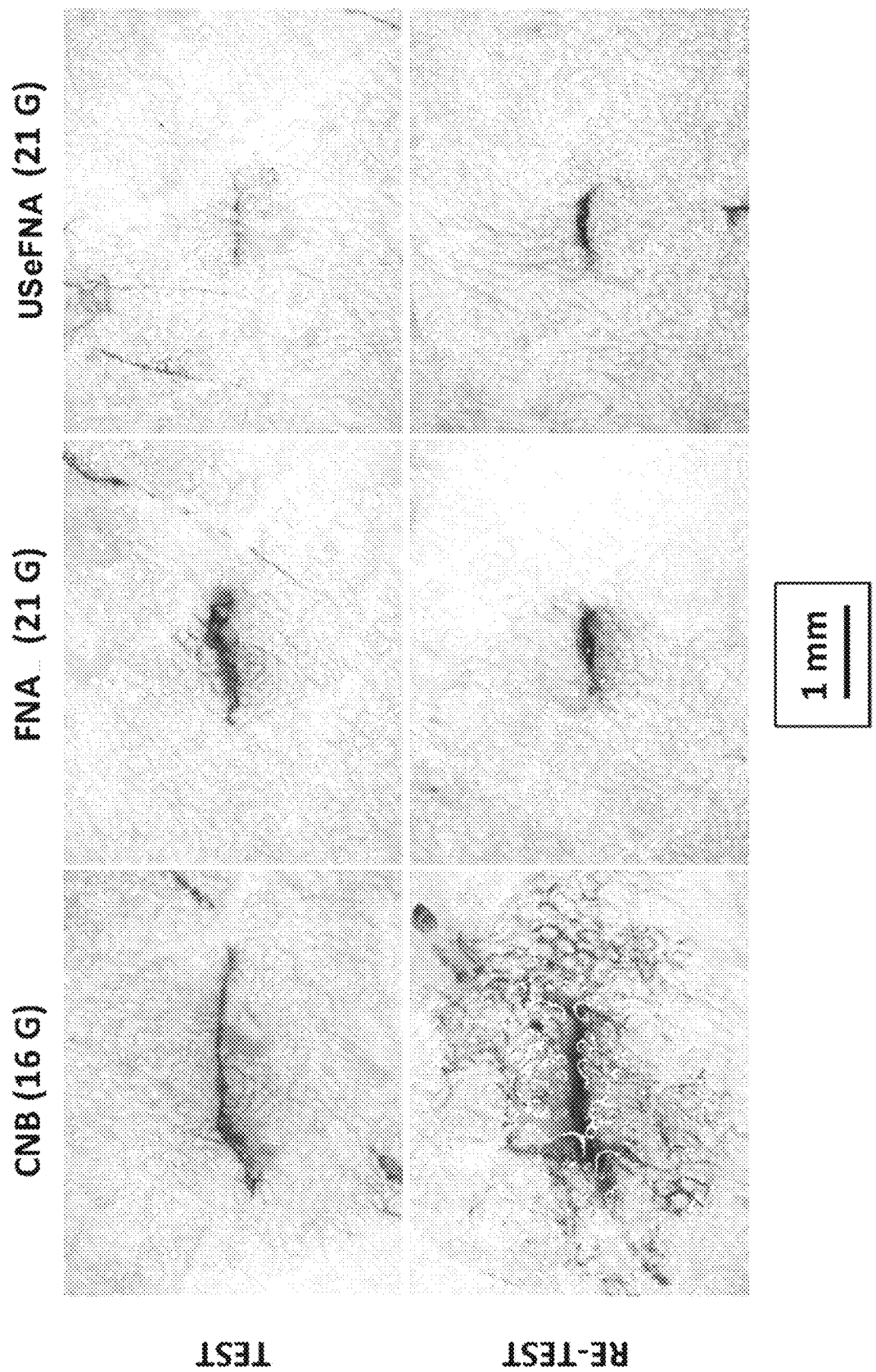
FIG. 13 shows pictures of porcine skin samples that were used for performing core needle biopsies (first column), fine needle aspiration biopsy (second column) and USeFNA biopsies (third column).

Referring now to FIG. 13, shown therein are pictures of porcine skin samples that were used for performing core needle biopsies (first column), fine needle aspiration biopsy (second column) and USeFNA biopsies (third column) using the embodiments shown in FIGS. 3A-3C. The CNB tests were performed using a 16 G needle, the Fine Needle Aspiration (FNA) Biopsy tests were performed using a 21 G needle and the USeFNA tests were also performed using a 21 G needle and stimulation parameters including a frequency of 30±2 kHz, a pulse repetition frequency=55 Hz, and 300 cycles per burst. The results shown in FIG. 13 are images seen under a microscope. To visualize the hole that was generated, black ink was placed on top of the locations of penetration and washed with water. A re-test was run (second row of images) to see if the outcomes were repeatable. The damage by CNB was greater compared to FNA or USeFNA. It also appeared that the hole generated with USeFNA was less destructive compared to FNA. The resistance force was smaller with USeFNA than with FNA or CNB. These results indicate that USeFNA may reduce the trauma to skin during and after penetration.

In another aspect, in at least one example embodiment described herein, the waveguide may be used as a resonator such that it acts as at least one of an energy storage unit, a frequency amplifier, an attenuator an acoustic diode. Choosing the shape, size, speed of sound and/or density of the waveguide appropriately can make the waveguide to be in resonance (e.g. energy storage) or in anti-resonance (e.g. attenuation). Accordingly, the same waveguide can be used for energy storage at one frequency and for attenuation at another frequency. Acoustic diodes may be used to pass energy into the conduit and permit sound waves returning back to the displacement signal source.

For example, assuming that there is a conduit that has resonance at frequencies of A, B and C Hz and there is a waveguide that is in resonance at B Hz, but out of resonance at A Hz and C Hz. Therefore, a displacement signal having a frequency of A or C Hz are attenuated or damped by the waveguide, but a displacement signal of B Hz passes through the waveguide without attenuation. Thus, the waveguide acts as a filter or a frequency selector, by mechanically "selecting" or allowing signal content at a frequency at B Hz to pass therethrough unattenuated. This may be useful in situations where the displacement signal source provides broadband excitation but the best conduit action is achieved at B Hz and frequency content at A and C Hz are not desired, the frequency selection provided by the waveguide can provide means to filter out the unnecessary frequencies. Accordingly, the eigenmodes (i.e. resonances) of the waveguide may be matched with the eigenmodes of the conduit to "select" the preferred resonant frequency of the conduit for preferred action at the tip of the conduit.

In another aspect, the USeFNA techniques described herein can be applied to needles (a.k.a. conduits) used for CNB. Since the CNB needle diameter is larger than the FNA needle diameter, the penetration force can be large and so if USeFNA is applied to CNB needles, then this may allow for penetration into stiff or calcified tissues to extract a core whereas CNB alone cannot accomplish this without having to apply considerable force. In another aspect, USeFNA combined with CNB may be used to loosen samples from a target object rather than to cut them from the target object. For example, USeFNA combined with CNB may be used to extract a core of muscle tissue or of tumor.

Figure 14A:
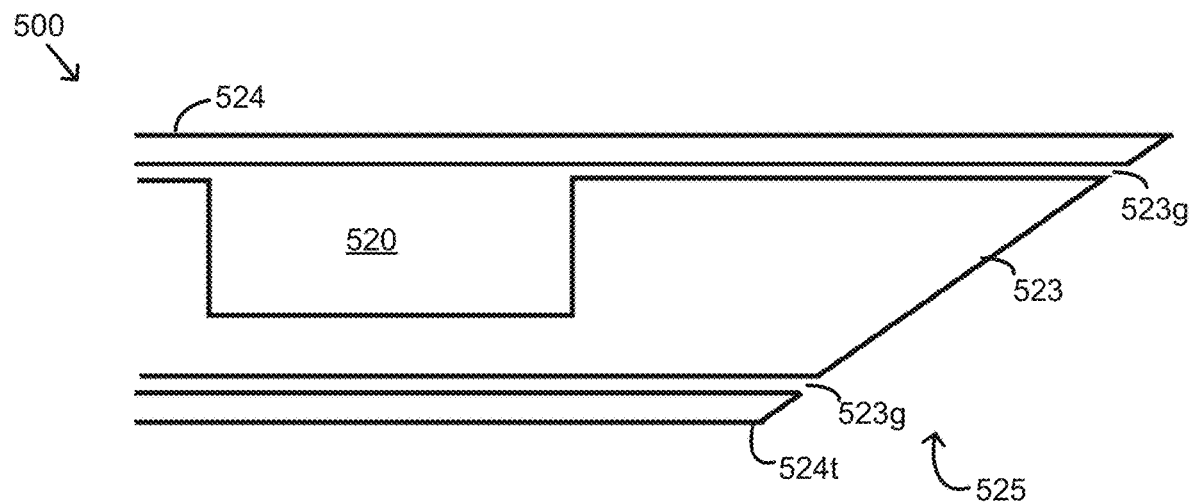
FIGS. 14A-14B show example embodiments of conduit structures that may be used when USeFNA is combined with CNB.
Figure 14B:
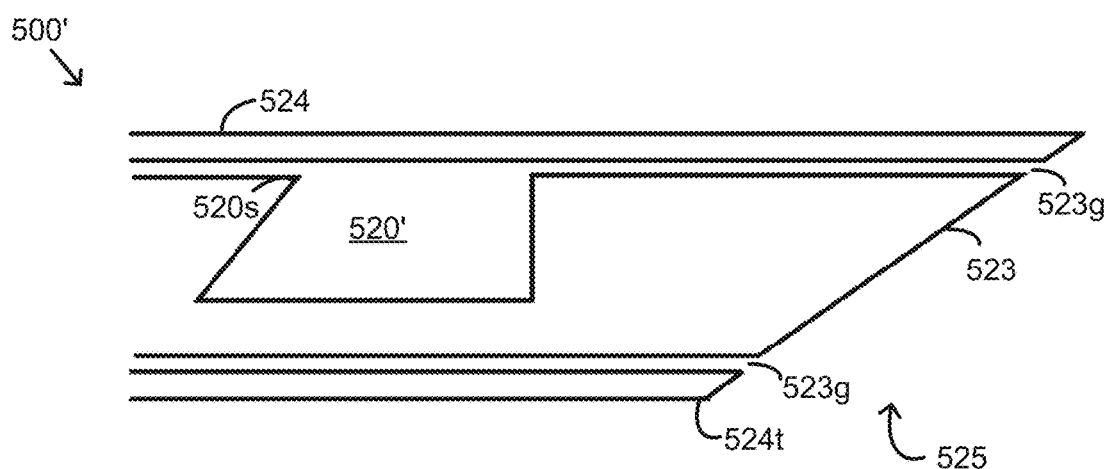
Figure 14C:
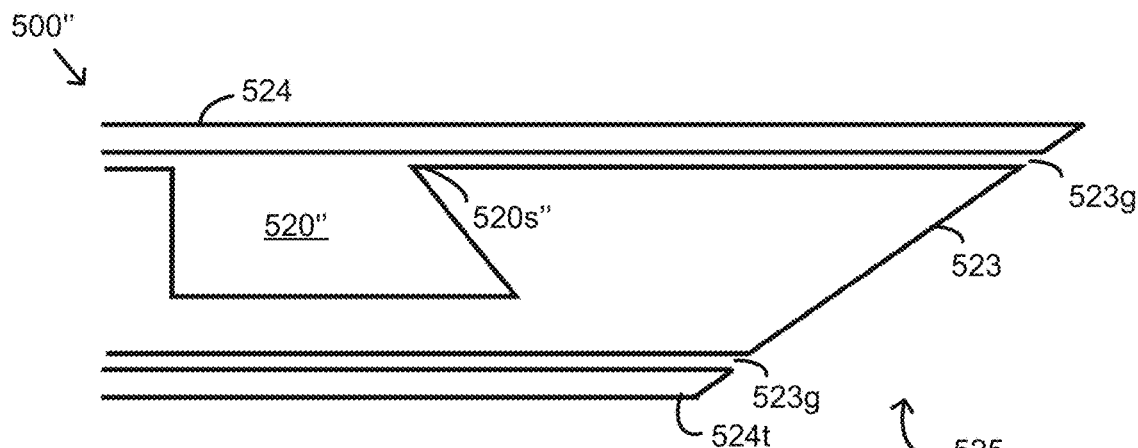

Referring now to FIGS. 14A-14C, shown therein example embodiments of conduit structures 500, 500' and 500" that may be used when USeFNA is combined with CNB. The conduit structure 500 comprises an outer conduit 524 with tapered wall 524t and an inner member 523 having a reservoir formed 520 formed therein. The conduit structure 500 has an end portion 525 with a beveled tip 523. There is a gap 523g around the outer surfaces of the inner member 523 that enable longitudinal and rotational movement of conduit 524 during biopsy procedure. The reservoir 520 may be used to store sampled entities or to store an entity that is to be delivered to a target object. The conduit structures 500' and 500" are similar in structure and operation to the conduit structure 500 except for having a different shaped reservoir 520' and 520" The sharp parts 520s and 520" of the reservoir 520' and 520" may have motion generated by a sound source, and their motion contributes to performing cutting at the target site (e.g. at tissue to obtain a tissue sample).

During use, the outer conduit 524 and the inner member 523 may be made to move in different directions with respect to each other. In addition, the boundaries of the reservoir 520 where a target object, e.g. core sample, is being collected, can be actuated by displacements, e.g. sound, to enhance cutting at the target object. This sound may be provided by coupling ultrasound energy, as explained for coupling for USeFNA described in accordance with the teachings herein, to the inner member 523, the outer conduit 524 or both the inner member 523 and the outer conduit 524 at same or different ultrasound parameters. The ultrasound-actuated elements contribute to cutting the object to obtain the sample. This approach can be used to acquire samples from tissues that are difficult to cut or to penetrate (e.g. calcified or fibrous tissues).

In another aspect, in at least one example embodiment described herein, the hollow structure of the conduit 24 may be used to guide electromagnetic waves, e.g. a laser beam, to the target site in order to enhance loosening of cellular constructs at the target site by one or more of thermal effects, optical disintegration and photo-acoustic phenomena (elastic or ablation). This may be achieved e.g. by focusing the optical beam into the inner portion of the conduit. This may be used in conjunction, i.e. simultaneously, before or after, applying mechanical or acoustic waves using the displacement signal source 14 along with the acoustic/mechanical couplers 38 and 40, the waveguide 42 and the converging structure 44.

In another aspect, in at least one example embodiment described herein, an external Ultrasound imaging machine or an MRI machine may be used to energize the conduit 24 with single or multiple beams. The benefit of using multiple beams is to deliver a higher amount of energy at the location where the beams cross (compared to using one beam or separate beams that do not intersect), while avoiding heating problems within a single beam. Another option to reduce the risk of heating is to use relatively low frequencies (e.g. <1 MHz), which typically attenuate less in the tissue than high frequencies. This may be achieved by using a magnetic needle and actuating the needle with external magnetic fields.

In another aspect, in at least one example embodiment described herein, the conduit 24 may be used to inject entities (e.g. anti-cancer drugs, genes, enzymes) into the target site. Prior to injection, the entities reside inside the conduit 24 or the reservoir 20. Before, during and/or after injection, the acoustic or mechanical waves coupled to the conduit 24 may be applied (i) to enhance uptake of the entities into the cells or into the tissue at the target site or (ii) to transport or deposit the entities into the target site, by enhancement of at least one of permeability, acoustic streaming, palpation by acoustic radiation force, cavitation and heating, for example). For example, if the group of delivered objects are enzyme molecules (e.g. trypsin or collagenase molecules), they may contribute to detaching the cells from the extra-cellular matrix at the target site by degrading the collagen matrix, for example.

Methods related to other embodiments according to the teachings herein may be used to extract cells or other entities from the target site into the conduit needle. For example, in one embodiment, the entities delivered through the conduit 24 may be modified (e.g. disintegrated, comminuted, integrated, formulation modified, atomized, or nebulized) by the mechanical or acoustic wave energy or electromagnetic waves delivered using the same conduit 24 needle or by other means. The delivered entities may be at least one of molecules, drugs, vehicles carrying the entities, imaging contrast agent, minerals, fixation chemicals and nanofibers, for example. If the delivered entity is a fixation chemical and the target site is tissue, the tissue sample may be fixed within the patient's body at the target tissue before detaching from the target site to preserve the original tissue morphology in the extracted sample. Additionally or alternatively, fixation may take place within the conduit 24 or the reservoir 20. Biologically active materials that may be of interest include, but are not limited to, analgesics, antagonists, anti-inflammatory agents, anthelmintics, antianginal agents, antiarrhythmic agents, antibiotics (including penicillins), anticholesterols, anticoagulants, anticonvulsants, antidepressants, antidiabetic agents, antiepileptics, antigonadotropins, antihistamines, antihypertensive agents, antimuscarinic agents, antimycobacterial agents, antineoplastic agents, antipsychotic agents, immunosuppressants, antithyroid agents, antiviral agents, antifungal agents, anxiolytic sedatives (hypnotics and neuroleptics), astringents, beta-adrenoceptor blocking agents, blood products and substitutes, anti-cancer agents, cardiacinotropic agents, contrast media, corticosterioids, cough suppressants (expectorants and mucolytics), diuretics, dopaminergics (antiparkinsonian agents), haemostatics, immunosuppressive and immunoactive agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, vasidilators, neuron blocking agents, anticholinergic and cholinomimetic agents, antimuscarinic and muscarinic agents, vitamins, and xanthines, for example. Some example medicaments include but are not limited to ibandronic acid, zolendronic acid, teriparatide, denosumab, IGF-1, TGF-beta, FGF-beta, BB1/biopharm and hydroxyapatite.

In another aspect, in at least one example embodiment described herein, an object may be delivered so that the object is between an implant material and tissue or bone using the device and the described drug delivery method. An example application may be that the object is hydroxyapatite and the hydroxyapatite may be delivered into bone pores, implant pores or implant-bone-interface for stronger adhesion of an implant to bone. If there is a bacterial infection around an implant, in one example embodiment, the conduit and the pressure controller can be used to first deliver an antiseptic between the implant and the surrounding tissue or bone (e.g. deliver the antiseptic into the gap between bone and implant). After the antiseptic is delivered, high-intensity mechanical or acoustic waves can be applied to the conduit in order to enhance delivery of the antiseptic around or into the implant or the tissue, or to enhance antiseptic action.

In another aspect, in at least one example embodiment described herein, the sampling device may be used to trigger an action of an entity such as, e.g., triggering the action of a drug. For example, embodiments of the device described herein can be used to trigger action of pressure sensitive drugs or thermosensitive drugs. For example a shell encapsulating a drug can be broken by the ultrasound energy provided by the sampling device to release the drug into the environment, which may be a tumor for example.

In another aspect, at least one of the example embodiments of the devices and methods described in accordance with the teachings herein may be used to break calculi (e.g. kidney or bladder stones) or to induce micro-fractures or perforations to bone (e.g. to subchondral bone to stimulate articular cartilage repair). In practice, the needle tip may be located near the calculi or located to be in contact with calculi. High amplitude acoustic or mechanical wave forces may be applied that are strong enough to break the calculi via at least one of shear/tensile forces, cavitation and cavitation-induced shock waves.

In another aspect, at least one example embodiment described herein may be used to generate an occlusion in a blood vessel by generating sufficient heat within or near the conduit 24. Alternatively, at least one example embodiment described herein may be used to induce thrombolysis by using at least one of shear-forces, acoustic streaming, radiation forces and cavitation, for example, to disintegrate the blood clot.

In another aspect, at least one example embodiment of the devices and methods described herein may be combined with motorized movement of the device and/or sample similar to a tattooing device or a sewing machine. The movement may also be achieved by means of robotics or tele-robotics in alternative embodiments. Applying the acoustic or mechanical waves to the needle of the sewing machine may permit lower mechanical resistance to sew strong materials e.g. thick leather or polymers.

In another aspect, any of the embodiments described herein may be modified to incorporate image-guidance by using current or prospective imaging techniques e.g. optical microscopy (e.g. light microscopy, optical coherence tomography, scanning white light interferometry), ultrasound imaging, photo-acoustic imaging, magnetic-resonance imaging, X-ray, computed tomography, micro-computed tomography, ESEM, SPECT or PET in an in vitro or in vivo setting and in a qualitative or quantitative manner.

In another aspect, in at least one example embodiment described herein the reservoir 20 may be filled with a fixative (e.g. ethanol or formalin) to fix the sample immediately after extraction from the target object. Alternatively, a separate vial having the fixative may be connected to the conduit 24. Alternatively, optical, electronic, pressure or chemical sensors known in the art may be incorporated into the conduit 24, outside the conduit 24 or into the reservoir 20 to obtain a reading of a relevant parameter (e.g. pH, blood sugar, oxygen saturation).

In another aspect, at least one of the example embodiments described in accordance with the teachings herein may be used in fine needle aspirate biopsies at any tissue site and there is likely to be a higher cell yield compared to conventional FNA for epithelial cells due to the ability to fine-tune the motion at the conduit tip using acoustic or mechanical wave mode selection in accordance with the teachings herein.

In another aspect, at least one of the example embodiments described in accordance with the teachings herein may be used in cytology (e.g. in scraping or brushing) for any tissue site with a surface such as, but not limited to, skin tissue, oral tissue, the cervix, the prostate, the bladder, the ureter, the G-I tract, the trachea, the bronchus, and endovascular structures. The motion of the conduit tip 26 or conduit end portion 25 can be adapted by selecting particular bevels and acoustic or mechanical wave modes based on tissue type or based on selectively extracting single cells or a cluster of cells.

In the above-noted applications, the samples may be retrieved for analysis for cytology, genomics, transcriptomics, proteomics, or metabolomics.

In another aspect, at least one embodiment of the sampling device described in accordance with the teachings herein may be tunable to sample single cells or cell clusters, or to sample from connective tissue, sarcomas, and cancers with extensive collagen, for example. Again for these different uses, the motions of the conduit tip 26 or conduit end portion 25 can be adapted by selecting particular bevels and acoustic or mechanical wave modes to achieve better sampling of certain objects.

In another aspect, at least one embodiment of the sampling device described in accordance with the teachings herein may be used in the field of endodontics for various dental applications such as debris removal by "sampling" the debris using one of the sampling techniques described in accordance with the teachings herein and/or irrigation by delivering a fluid to a region of a patient's mouth using one of the object delivery techniques described in accordance with the teachings herein. Alternatively, a device in accordance with the teachings herein may be used to fill dental canals or micro-cracks or to enhance tooth whitening.

In another aspect, at least one embodiment of the sampling device described according to the teachings herein may be used in facilitating histology, histochemistry, cytology or cytochemistry preparation by obtaining samples that may be used for fixed, dehydrated tissue renaturation (alcohol to aqueous environment in cell or tissue or tissue section preparations) to enable antibody binding and other purposes or to obtain samples that may be used in antibody staining (i.e. forcing antibodies into cells), in vitro, in a cell culture and in vivo.

In another aspect, USeFNA may be used with a larger conduit (or even multiple conduits) to perform a liposuction-type procedure. Obesity is a major problem, and liposuction is a means of cosmetic surgery for this condition. Liposuction does have its hazards including death from fat which enters blood vessels and becomes fat emboli. In this situation, USeFNA may be advantageous as it might be used to obtain fat cells or fat and leave blood vessels intact. For example, USeFNA may be used in cosmetic facial surgery where the amount of fat removed is more modest. Alternatively, in hip surgery, a fat embolism occasionally occurs because fat is mobilized in the femoral bone marrow during the exothermic process of placing in bone cement. USeFNA may be used to remove fatty marrow reducing this hazard.

In another aspect, for at least one of the devices described herein the mechanical displacement signal can be generated to have a frequency in the frequency range of 200 kHz-20 MHz and the device can be used in therapeutic applications that operate in this frequency range.

In another aspect, for at least one of the devices described herein the mechanical displacement signal can be generated to have a frequency in the frequency range of 200 kHz-20 MHz with continuous waves or a high duty cycle (e.g. >1%) and the device may be used to aid in cauterization or reduction in bleeding. At high frequencies attenuation in tissue is high so the very high frequency ultrasound energy that is generated and applied to the conduit will be deposited in the target tissue near the distal end portion and the tip of the conduit which will aid in cauterization or bleeding reduction in tissue that is local or nearby to the conduit end portion and tip.

The example embodiments that have been presented in accordance with the teachings herein are not limited by (i) number, duration, shape, frequency content of pulses or pulse repetition frequency or frequencies (ii) shape, size, wall thickness, needle or needle end geometry, material selection of the needle or its coating, (iii) hardware or software configuration of mechanical displacement generating means or (iv) hardware or software configuration of the pressure controller.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A device for delivery of acoustic or mechanical energy to perform an action at a target site of an object, the device comprising:
   a conduit having an outer surface, a proximal end and a distal end with a tip;
   a displacement signal source for generating acoustic or mechanical waves having at least one frequency, wherein the acoustic or mechanical waves are converted to a mechanical displacement signal along the conduit;
   a coupling assembly having a first end coupled to the displacement signal source and a second end coupled at a coupling location on the conduit between the proximal end and the distal end of the conduit, the coupling assembly including a waveguide having a length and a width with the length being greater than the width and the waveguide being configured to guide the acoustic or mechanical waves in a longitudinal direction of the waveguide from the displacement signal source to the conduit during use;
   a pressure controller coupled to the proximal end of the conduit and being configured to vary an amount of pressure in the conduit during use; and
   a control unit coupled to the displacement signal source for controlling the displacement signal source to select the at least one frequency of the generated acoustic or mechanical waves based on the coupling location and a coupling angle between the second end of the coupling assembly and the conduit to provide a desired acoustic or mechanical wave mode at a portion of the conduit,
   wherein the desired acoustic or mechanical wave mode provides controlled movement for at least one of an end region of the conduit and the tip of the conduit.

2. The device of claim 1, wherein the coupling location on the conduit is near the proximal end of the conduit or a central part of the conduit.

3. The device of claim 1, wherein the displacement signal source has a longitudinal axis that is offset or at an angle with respect to the conduit and the coupling assembly has a transition region where a longitudinal central axis of the waveguide is different than a longitudinal central axis of the displacement signal source.

4. The device of claim 3, wherein the waveguide is operated as a resonator having an eigenmode that is selected to achieve a preferred resonant frequency of the conduit for improved action at the tip of the conduit.

5. The device of claim 3, wherein a portion of the waveguide has an S shape or a J-shape.

6. The device of claim 5, wherein the second end of the coupling assembly comprises a converging structure to provide a first stage of amplification for the mechanical displacement signal as the mechanical displacement signal is coupled to the conduit.

7. The device of claim 6, wherein the converging structure comprises an upper portion with a first channel on a lower surface thereof, and a lower portion with a second channel on an upper surface thereof, the first and second channels being sized to receive a portion of the conduit therebetween to transfer the mechanical displacement signal thereto during use.

8. The device of claim 3, wherein a length and shape of the waveguide are selected to allow the desired acoustic or mechanical wave mode within the waveguide.

9. The device of claim 3, wherein the coupling assembly includes an acoustic/mechanical coupler to couple a first end of the waveguide to the displacement signal source and an additional acoustic/mechanical coupler to couple a second end of the waveguide to the conduit.

10. The device of claim 1, wherein the second end of the coupling assembly contacts the outer surface of the conduit tangentially to create acoustic or mechanical waves on an inner surface of the conduit and the outer surface of the conduit.

11. The device of claim 1, wherein the device further comprises at least one additional displacement signal source and a corresponding at least one additional coupling assembly that is coupled to the conduit from a different direction than the coupling assembly so that mechanical displacement signals from the at least one additional displacement signal source are coupled to the conduit from at least two of an X-direction, a Y-direction, a Z-direction, or an angle with respect to a longitudinal axis of the conduit and a desired acoustic or mechanical wave mode is generated during use to provide the controlled movement for at least one of an end region of the conduit and the tip of the conduit.

12. The device of claim 1, wherein operational parameters are selected to achieve the controlled movement comprising a linear or non-linear motion in at least one of the Y-direction, the X-direction, and the Z-direction direction with respect to a longitudinal axis of the conduit, a rotational movement, a torsional movement, a flexural movement or a pitch movement, a yaw movement or a tilting movement.

13. The device of claim 1, wherein the desired acoustic or mechanical wave mode is selected to achieve a controlled cavitation at a desired location along the outside or the inside of the conduit, to generate a standing wave within or inside the conduit to arrange entities obtained from the target site according to a certain characteristic of the entities including an order of increasing size of the entities, to increase action at the tip of the conduit and decrease action at other portions of the conduit, and/or to increase activity at a portion or tip of the conduit based on material and structural properties of the coupling assembly and the conduit and frequency of the mechanical displacement signal.

14. The device of claim 1, wherein the control unit is configured to select at least one of a shape, a frequency, a repetition rate, a delay, an amplitude and a linearity or non-linearity of the displacement signal based on the coupling location and the coupling angle to obtain a desired path of movement at a selected location on the conduit or at the tip of the conduit.

15. The device of claim 14, wherein the control unit is configured to select the shape of the mechanical displacement signal based on selecting at least one of a pulse, a burst, an impulse, a whiplash, a chirp, a pre-defined noise, a random noise, a shock wave, a sine wave, a sawtooth wave, and a square wave.

16. The device of claim 1, wherein the conduit provides an additional waveguide for delivering the mechanical displacement signal to the target site.

17. The device of claim 1, wherein the displacement signal source comprises at least one of a Langevin transducer, a flextensional piezo actuator, a piezo transducer, an electric spark gap, a pyrotechnic spark, an optically-induced plasma spark, a PMUT, a CMUT, an IDT, an RF source and a motor.

18. The device of claim 1, wherein the mechanical displacement signal is generated to have a main frequency component or multiple frequency components in the range of about 0.1 Hz to 100 MHz, and more preferably in the range of about 10 kHz to 200 kHz and a momentary or time-averaged intensity of the mechanical displacement signal is in the range of about 1 mW/cm$^2$ to 10 kW/cm$^2$, and more preferably in the range of about 0.1 to 100 W/cm$^2$.

19. The device of claim 1, wherein the mechanical displacement signal is generated to have a main frequency component or multiple frequency components in the range of about 200 kHz to 20 MHz, with continuous waves or a duty cycle of at least 1% and/or the device is used to aid in cauterization or reduction in bleeding at the target site.

20. The device of claim 1, wherein at least one of the outer surface and an inner surface of the conduit is coated or patterned to provide at least one of: (i) an antiseptic surface, (ii) enhancement of extraction of a given entity, (iii) cavitation nucleation sites or (iv) modified interaction between the conduit and the target site and between the conduit and the extracted given entity in order to provide at least one of better preservation of cells or to detach more cells when obtaining the given entity by generating propagating mechanical solitons or spatially controlled cavitation.

21. The device of claim 1, wherein the outer surface of the conduit and certain parameters of the displacement signal source are adapted to generate surface waves on the outer surface of the conduit or to actuate the tip of the conduit to reduce friction during insertion or extraction of the conduit at the target site.

22. The device of claim 1, wherein the distal end of the conduit comprises an end portion having the tip and the tip includes a bevel that provides an additional stage of amplification for the mechanical displacement signal to achieve an action at the tip compared to another portion of the conduit.

23. The device of claim 22, wherein the bevel has a shape selected to achieve a desired acoustic or mechanical wave mode at the end portion of the conduit, the conduit has a tubular wall with a sawtooth pattern on its outer surface or its inner surface and a flat bevel end portion, the conduit has a tubular wall that is tapered and end portions of the tubular wall are curved to provide a wavy profile for the bevel, and/or the bevel has an average opening angle in the range of about 0.1-180° and more preferably in the range of about 5-45°.

24. The device of claim 1, wherein the conduit comprises two concentric cylinders that each have beveled ends and separately receive the mechanical displacement signal so that a beveled end of the outer cylinder moves momentarily in a different direction than a beveled end of the inner cylinder for enhanced interaction between the conduit tip and the target site and movement of the beveled end comprises a horizontal direction parallel to a longitudinal axis of the conduit, a vertical direction with respect to the longitudinal axis of the conduit, and/or a radial direction with respect to the longitudinal axis of the conduit.

25. The device of claim 1, wherein the conduit is split vertically into two halves to allow for different motion in the different halves.

26. The device of claim 1, wherein an inner surface or the outer surface of the conduit comprises at least one of grooves, holes, dents, and patterns to provide cavitation nucleation sites during use.

27. The device of claim 1, wherein the conduit or the pressure controller comprises at least one of an optical sensor, an electronic sensor, a pressure sensor or a chemical sensor to obtain measurements of at least one condition at the target site during use.

28. The device of claim 1, wherein the device is operable to atomize or nebulize a given object and spray the atomized or nebulized given object onto a material surface or into a cavity.

29. The device of claim 1, wherein the action comprises obtaining a first entity from the target site, the distal end of the conduit has an aperture that is disposed at the target site during use for obtaining the first entity therefrom, the pressure controller is configured to vary an amount of suction pressure in the conduit when obtaining the first entity, and the control unit is configured to implement the desired acoustic or mechanical wave mode at a portion of the conduit when obtaining the first entity from the target site and optionally the conduit acts as a common channel for receiving the first entity from the target site.

30. The device of claim 29, wherein the outer surface of the conduit and certain parameters of the displacement signal source are adapted to generate surface waves on the outer surface of the conduit or to actuate the tip of the conduit to maintain aspirated entities intact when obtaining the entities.

31. The device of claim 29, wherein the distal end of the conduit has a puncturing structure for penetrating and actuating the target site when obtaining the first entity and the tip includes a bevel having a shape selected to achieve a desired entity extraction mechanism at the end portion of the conduit.

32. The device of claim 29, wherein the pressure controller comprises a reservoir that is adapted to receive the first entity and optionally the pressure controller comprises a conventional syringe coupled to a needle that provides the conduit and the reservoir and the syringe has a piston with a handle at one end for actuation of the syringe and a plunger at another end that is disposed in the reservoir of the syringe.

33. The device of claim 1, wherein the action comprises delivering a second entity to the target site, the distal end of the conduit has an aperture that is disposed at the target site during use for delivering the second entity therefrom, the pressure controller is configured to vary an amount of delivery pressure in the conduit when delivering the second entity, and the control unit is configured to implement the desired acoustic or mechanical wave mode at a portion of the conduit when delivering the second entity to the target site, and optionally the conduit acts as a common channel for delivering the second entity to the target site.

34. The device of claim 33, wherein the distal end of the conduit has a puncturing structure for penetrating and actuating the target site when delivering the second entity and the tip includes a bevel having a shape selected to achieve a desired entity delivery mechanism at the end portion of the conduit.

35. The device of claim 33, wherein the pressure controller comprises a reservoir that is adapted to store the second entity to be delivered to the target site and optionally the pressure controller comprises a conventional syringe coupled to a needle that provides the conduit and the reservoir and the syringe has a piston with a handle at one end for actuation of the syringe and a plunger at another end that is disposed in the reservoir of the syringe.

36. The device of claim 33, wherein the second entity that is delivered to the target site comprises one of a drug, a cell, a fixative, and a nanoparticle and/or the object comprises one of alive or dead flora, and alive or dead fauna.

37. The device of claim 1, wherein the action comprises obtaining a first entity from the target site or delivering a second entity to the target site, the distal end of the conduit has an aperture that is disposed at the target site during use for obtaining the first entity therefrom or delivering the second entity to the target site, the pressure controller is configured to vary an amount of suction pressure in the conduit when obtaining the first entity or vary an amount of delivery pressure in the conduit when delivering the second entity, and the control unit is configured to implement the desired acoustic or mechanical wave mode at a portion of the conduit when obtaining the first entity from the target site or delivering the second entity to the target site.

38. The device of claim 37, wherein the conduit also acts a common channel for receiving the first entity from the target site or delivering the second entity to the target site.

39. The device of claim 37, wherein the distal end of the conduit has a puncturing structure for penetrating and actuating the target site when obtaining the first entity or delivering the second entity and the tip includes a bevel having a shape selected to achieve a desired entity extraction mechanism at the end portion of the conduit when sampling the first entity from the target site or to achieve a desired entity delivery mechanism when delivering the second entity to the target site.

40. The device of claim 37, wherein the pressure controller comprises a reservoir that is adapted to receive the first entity during sampling or to hold the second entity prior to delivery.

41. The device of claim 37, wherein the first entity is sampled from the target site before the second entity is delivered to the target site or the second entity is delivered to the target site before the first entity is sampled from the target site.

42. The device of claim 1, wherein the device comprises an inner member disposed within the conduit and separated from an inner surface of the conduit by a gap, the inner member comprising a reservoir, the conduit and inner member being sized to perform core needle biopsies and the mechanical displacement signal is coupled to at least one of the conduit and the inner member to cause relative motion between the conduit and the inner member.

43. The device of claim 42, wherein the reservoir of the inner member comprises a sharp corner and the inner member receives the mechanical displacement signal to cause an end portion of the inner member to extend past the conduit and allow the reservoir with the sharp corner to aid in performing a cutting motion at the target site.

44. A method of obtaining a first entity from a target site of an object or delivering a second entity to the target site of the object, the method comprising:
   placing a device at the target site, the device comprising:
      a conduit having an outer surface, a proximal end and a distal end, the distal end having an aperture that is disposed at the target site of the object for obtaining the first entity therefrom or delivering the second entity thereto during use;
      a displacement signal source disposed near the proximal end of the conduit, the displacement signal source being configured to generate acoustic or mechanical waves having at least one frequency, wherein the acoustic or mechanical waves are converted to a mechanical displacement signal along the conduit;
      a coupling assembly for coupling the displacement signal source to the conduit at a coupling location and a coupling angle at a portion of the conduit, the coupling assembly including a waveguide having a length and a width with the length being greater than the width and the waveguide being configured to guide the acoustic or mechanical waves in a longitudinal direction of the waveguide from the displacement signal source to the conduit during use;
      a pressure controller coupled to the proximal end of the conduit for varying an amount of pressure therein for delivery of the second entity or acquiring of the first entity; and
      a control unit coupled to the displacement signal source for controlling the displacement signal source;
   selecting the at least one frequency of the generated acoustic of mechanical waves based on the coupling location and the coupling angle between the coupling assembly and the conduit to provide a desired acoustic or mechanical wave mode at a portion of the conduit to provide controlled movement for at least one of an end region of the conduit and a tip of the conduit when obtaining the first entity from the target site or delivering the second entity to the target site; and generating the mechanical displacement signal using the displacement signal source to obtain the first entity from the target site or deliver the second entity to the target site.

45. The method of claim 44, wherein before generating the mechanical displacement signal, the method comprises:
actuating the pressure controller to a first volume setting for a reservoir of the pressure controller;
inserting the conduit into the target site; and
actuating the pressure controller to a second volume setting for the reservoir of the pressure controller, the second volume being larger than the first volume.

46. The method of claim 45, wherein the mechanical displacement signal is generated for a first time period after which the pressure controller is actuated to relieve decompression to obtain the first entity from the target site, and the conduit is withdrawn from the target site.

47. The method of claim 46, wherein after withdrawing the conduit from the target site, the pressure controller is actuated to eject the obtained first entity onto a glass slide or in a container.

48. The method of claim 44, wherein while generating the mechanical displacement signal, the method comprises obtaining the first entity from the target site or delivering the second entity to the target site.

49. The method of claim 44, wherein while generating the mechanical displacement signal, the method comprises inserting the conduit into the target site or removing the conduit from the target site by hand or with robotics in order to achieve translation, tilting and/or rotation of the conduit or conduit tip within or outside of the target site.

50. The method of claim 44, wherein the desired acoustic or mechanical wave mode is selected to actuate a proximal portion of the conduit, a distal end portion of the conduit or both the proximal and distal end portions of the conduit.

51. The method of claim 50, wherein the wave mode is selected to cause different portions of the conduit to experience different wave modes or to perform different actions.

52. The method of claim 44, wherein before generating the mechanical displacement signal, the method comprises:
inserting the second entity into a reservoir of the device;
actuating the pressure controller to a first volume setting for the reservoir of the pressure controller;
inserting the conduit into the target site; and
actuating the pressure controller to a second volume setting for the reservoir of the pressure controller, the second volume being smaller than the first volume to deliver the second entity to the target site.

53. The method of claim 44, wherein the method comprises using different shapes and bevels for the distal end of the conduit to detach cells selectively by one or more of cell size, cell shape, cell orientation, cell pathology, cell count, and cell type.

54. The method of claim 44, wherein the method comprises configuring the displacement signal source to generate the acoustic or mechanical waves and using a shape for the distal end of the conduit to apply sufficient force and/or stress at the target site to detach cells, groups of cells, clusters of cells, extracellular tissue matrix including fibers, tissue fragments including or more of pathologies, soft tissue or hard tissue.

55. The method of claim 44, wherein the second entity that is delivered to the target site comprises molecules, drugs, vehicles carrying the second entity, imaging contrast agent, minerals, fixation chemicals, nanofibers, a cell, a fixative, a nanoparticle, genes, or enzymes.

56. The method of claim 44, wherein the method comprises using the device to trigger an action of the second entity.

57. The method of claim 56, wherein the second entity includes pressure sensitive drugs or thermosensitive drugs.

58. The method of claim 44, wherein the method comprises using the wave mode to activate a content which is delivered as cells, or particles in a motion/fluid/cell/tissue translation.

\* \* \* \* \*